(12) United States Patent
Toyofuku et al.

(10) Patent No.: US 12,358,879 B2
(45) Date of Patent: Jul. 15, 2025

(54) HETEROCYCLIC COMPOUND

(71) Applicant: Takeda Pharmaceutical Company Limited, Osaka (JP)

(72) Inventors: Masashi Toyofuku, Kanagawa (JP); Yoshiteru Ito, Kanagawa (JP); Marilena Pira, Kanagawa (JP); Takahiro Sugimoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 749 days.

(21) Appl. No.: 17/766,400

(22) PCT Filed: Oct. 15, 2020

(86) PCT No.: PCT/JP2020/038850
§ 371 (c)(1),
(2) Date: Apr. 4, 2022

(87) PCT Pub. No.: WO2021/075476
PCT Pub. Date: Apr. 22, 2021

(65) Prior Publication Data
US 2023/0322683 A1    Oct. 12, 2023

(30) Foreign Application Priority Data

Oct. 18, 2019 (JP) ................ 2019-191533

(51) Int. Cl.
| | |
|---|---|
| C07D 231/56 | (2006.01) |
| A61P 25/28 | (2006.01) |
| C07D 405/12 | (2006.01) |
| C07D 471/04 | (2006.01) |
| C07D 498/04 | (2006.01) |

(52) U.S. Cl.
CPC ............ *C07D 231/56* (2013.01); *A61P 25/28* (2018.01); *C07D 405/12* (2013.01); *C07D 471/04* (2013.01); *C07D 498/04* (2013.01)

(58) Field of Classification Search
CPC ................ C07D 231/56; A61P 25/28
See application file for complete search history.

(56) References Cited

U.S. PATENT DOCUMENTS

| | | |
|---|---|---|
| 2010/0197673 A1 | 8/2010 | Kim et al. |
| 2010/0210647 A1 | 8/2010 | Kim et al. |
| 2012/0252798 A1 | 10/2012 | Kim et al. |
| 2013/0225642 A1 | 8/2013 | Inoue et al. |
| 2013/0237532 A1 | 9/2013 | Kim et al. |
| 2014/0024618 A1 | 1/2014 | Kim et al. |
| 2017/0015655 A1 | 1/2017 | Kaieda et al. |
| 2018/0000771 A1 | 1/2018 | Inoue et al. |
| 2018/0354908 A1 | 12/2018 | Cowley et al. |
| 2019/0008836 A1 | 1/2019 | Kaieda et al. |
| 2020/0172492 A1 | 6/2020 | Cowley et al. |

FOREIGN PATENT DOCUMENTS

| | | |
|---|---|---|
| EP | 2 489 663 A1 | 8/2012 |
| JP | 2010-536846 A | 12/2010 |
| JP | 2017-533957 A | 11/2017 |
| JP | 2018-524378 A | 8/2018 |
| WO | WO-2004/113303 A1 | 12/2004 |
| WO | WO-2012/029994 A1 | 3/2012 |
| WO | WO-2016/114322 A1 | 7/2016 |
| WO | WO-2017/014170 A1 | 1/2017 |

OTHER PUBLICATIONS

Ashton et al., "Increased plasma neurofilament light chain concentration correlated with severity of post-mortem neurofibrillary tangle pathology and neurodegeneration," Acta Neuropathologica Communications, Jan. 9, 2019, 7:5, 1-11.
Cotticelli et al., "Ferroptosis as a Novel Therapeutic Target for Friedreich's Ataxia," The Journal of Pharmacology and Experimental Therapeutics, Apr. 2019, 369:47-54.
Egawa et al., "Drug Screening for ALS Using Patient-Specific Induced Pluripotent Stem Cells," Science Translational Medicine, Aug. 1, 2012, 4:145ra104, 1-10.
Fischer et al., "Old age-associated phenotypic screening for Alzheimer's disease drug candidates identifies sterubin as a potent neuroprotective compound from Yerba santa," Redox Biology, 2019 (online Dec. 21, 2018), 21:101089, 1-12.
Fujimori et al., "Modeling sporadic ALS in iPSC-derived motor neurons identifies a potential therapeutic agent," Nature Medicine, Oct. 2018, 24:1579-1589.
Imamura et al., "The Src/c-Abl pathway is a potential therapeutic target in amyotrophic lateral sclerosis," Science Translational Medicine, May 24, 2017, 9:eaaf3962, 1-11.
Li et al., "Protective effects of tetramethylpyrazine analogue Z-11 on cerebral ischemia reperfusion injury," European Journal of Pharmacology, 2019 (online Nov. 29, 2018), 844:156-164.

(Continued)

*Primary Examiner* — John S Kenyon
*Assistant Examiner* — John D McAnany
(74) *Attorney, Agent, or Firm* — Foley & Lardner LLP

(57) ABSTRACT

The present invention provides a compound having a cell degeneration inhibitory action, particularly a motor neuron degeneration inhibitory action, which is useful as an agent for the prophylaxis or treatment of motor neuron diseases (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like. The present invention relates to a compound represented by the formula (I):

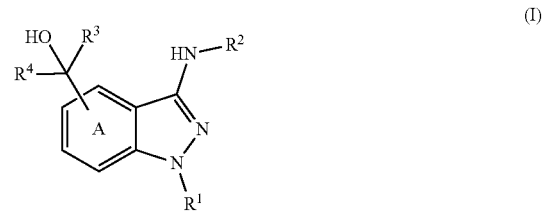

wherein each symbol is as described in the specification, or a salt thereof.

15 Claims, No Drawings

(56) References Cited

OTHER PUBLICATIONS

Li et al., "Proteomics of neurodegenerative diseases: analysis of human post-mortem brain," Journal of Neurochemistry, 2018, 10.111/jnc.14603, 1-11.
Shi et al., "Induced pluripotent stem cell technology: a decade of progress," Nature Reviews Drug Discovery, Feb. 2017, 16:115-130.
Smith et al., "Small-Molecule Anticonvulsant Agents with Potent In Vitro Neuroprotection and Favorable Drug-Like Properties," J. Mol. Neurosci., 2014 (online Nov. 26, 2013), 52:446-458.
Van Es et al., "Amyotrophic lateral sclerosis," Lancet, May 25, 2017, 390:2084-2098.
Vanden Berghe et al., "Regulated necrosis: the expanding network of non-apoptotic cell death pathways," Nature Reviews Molecular Cell biology, Feb. 2014, 15:135-147.
Zhang et al., "Necroptosis in neurodegenerative diseases: a potential therapeutic target," Cell Death and Disease, Jun. 29, 2017, 8:e2905, 9 pages.

HETEROCYCLIC COMPOUND

CROSS-REFERENCE TO RELATED APPLICATIONS

This application is the U.S. National Stage of PCT/JP2020/038850, filed Oct. 15, 2020, which claims priority to JP 2019-191533, filed Oct. 18, 2019.

TECHNICAL FIELD

The present invention relates to a heterocyclic compound having a cell degeneration inhibitory action, particularly a motor neuron degeneration inhibitory action, which is useful for the treatment of motor neuron diseases (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like, and a medicament comprising the compound, and the like.

BACKGROUND OF THE INVENTION

Abnormal cell degeneration caused by a disease is a widely observed pathological change as the condition progresses. If the normal function of cell tissue can be maintained and restored by suppressing abnormal cell degeneration due to therapeutic intervention, it can directly lead to suppression of pathological progression, improvement of symptoms, and treatment of diseases (Non-Patent Documents 1, 2 and 3). In many neurodegenerative diseases, degeneration/loss of nerve tissue presumed to be based on pathologically-induced cell degeneration has been observed by analysis of pathological samples obtained after the death of a patient (Non-Patent Documents 4 and 5). Based on this fact, a research strategy for searching for compounds that suppress neuronal degeneration as therapeutic drug candidate substances has been proposed, and compound screening using a cell-based assay that mimics neuronal degeneration in vitro has been carried out (Non-Patent Documents 6 and 7). In particular, drug discovery research for inducing differentiation of disease model cells from induced pluripotent stem cells (hereinafter, iPS cells) obtained by reprogramming somatic cells collected from patients and using them for compound screening is becoming active (Non-Patent Document 8). In motor neuron diseases represented by amyotrophic lateral sclerosis (hereinafter sometimes referred to as "ALS"), selective degeneration/loss of motor neurons have also been observed in many cases (non-Patent Document 9). Therefore, if a compound that suppresses spontaneous cell degeneration observed in motor neurons differentiation-induced from patient-derived iPS cells can be found, it will be expected to create new drugs that suppress pathological progression and improve symptoms and the like (Non-Patent Documents 10, 11 and 12 and Patent Documents 1 and 2).

From the above, it is suggested that motor neuron degeneration inhibitors may be an agent for the prophylaxis or treatment of motor neuron diseases (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like.

Friedreich's ataxia (hereinafter, FA) is an autosomal recessively inheritable disease caused by mutation in the Frataxin (FXN) gene. Since FXN is a protein having an iron-regulating function in mitochondria, it has been suggested that iron-dependent cell death is involved in the disease, and it has been reported that skin fibroblasts derived from FA patients are highly sensitive to Erastin and RSL3, which are known as iron-dependent cell death inducers (Non-Patent Document 13).

As heterocyclic compounds, the following compound is known.

Patent Document 3 describes that a compound represented by the following formula:

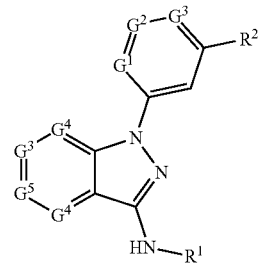

wherein each symbol is as defined in Patent Document 3, is useful for the treatment of asthma and chronic obstructive pulmonary diseases (COPD).

DOCUMENT LIST

Patent Document

Patent Document 1: WO 2016/114322
Patent Document 2: WO 2012/029994
Patent Document 3: EP 2489663

Non-Patent Document

Non-Patent Document 1: S. Zhang et al, Cell Death and Disease 2017, 8, e2905
Non-Patent Document 2: T. V. Berghe et al, Nature Reviews Molecular Cell Biology 2014, 15, 135-147.
Non-Patent Document 3: Z. Lia et al, European Journal of Pharmacology 2019, 844, 156-164.
Non-Patent Document 4: K. W. Li et al, Journal of Neurochemistry 2018, 10.1111/jnc.14603
Non-Patent Document 5: N. J. Ashton et al, Acta Neuropathologica Communications 2019, 7:5
Non-Patent Document 6: G. R. Smith et al, Journal of Molecular Neuroscience 2014, 52, 446-458.
Non-Patent Document 7: W. Fischer et al, Redox Biology 2019, 21, 101089
Non-Patent Document 8: Y. Shi et al, Nature Reviews Drug Discovery 2017, 16, 115-130.
Non-Patent Document 9: A. E. Michael et al, Lancet 2017, 390, 2085-2098.
Non-Patent Document 10: N. Egawa et al, Science Translational Medicine 2012, 4, 145ra104
Non-Patent Document 11: K. Imamura et al, Science Translational Medicine 2017, 9, eaaf3962
Non-Patent Document 12: K. Fujimori et al, Nature Medicine 2018, 24, 1579-1589.

Non-Patent Document 13: M. G. Cotticelli et al, J Pharmacol Exp Ther 2019, 369, 47-54.

SUMMARY OF THE INVENTION

Problems to be Solved by the Invention

An object of the present invention is to provide a compound having a cell degeneration inhibitory action, particularly a motor neuron degeneration inhibitory action, which is useful as an agent for the prophylaxis or treatment of motor neuron diseases (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like.

Means of Solving the Problems

The present inventors have conducted intensive studies in an attempt to solve the above-mentioned problems and found that a compound represented by the following formula (I) has a cell degeneration inhibitory action, particularly a motor neuron degeneration inhibitory action, and therefore, the compound is useful as an agent for the prophylaxis or treatment of motor neuron diseases (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like, which resulted in the completion of the present invention.

Accordingly, the present invention provides the following.

[1] A compound represented by the formula

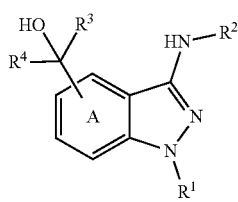

(I)

wherein
$R^1$ is a hydrogen atom, an optionally substituted $C_{1-6}$ alkyl group, or an optionally substituted $C_{3-6}$ cycloalkyl group;
$R^2$ is an optionally substituted $C_{1-6}$ alkyl group, or an optionally substituted cyclic group;
$R^3$ is an optionally substituted $C_{1-6}$ alkyl group;
$R^4$ is an optionally substituted $C_{1-6}$ alkyl group; and
Ring A is an optionally further substituted benzene ring, or a salt thereof (hereinafter sometimes to be referred to as "compound (I)");

[2] The compound or salt of the above-mentioned [1], wherein
$R^1$ is
(1) a hydrogen atom,
(2) a $C_{1-6}$ alkyl group optionally substituted by 1 to 3 of optionally halogenated $C_{3-6}$ cycloalkyl groups, or
(3) a $C_{3-6}$ cycloalkyl group;
$R^2$ is
(1) a $C_{3-6}$ cycloalkyl group,
(2) a $C_{6-10}$ aryl group optionally substituted by 1 to 3 substituents selected from
    (a) a halogen atom,
    (b) an optionally halogenated $C_{1-6}$ alkyl group,
    (c) a $C_{1-6}$ alkoxy group, and
    (d) a 5- or 6-membered monocyclic aromatic heterocyclic group optionally substituted by 1 to 3 $C_{1-6}$ alkyl groups,
(3) a 5- or 6-membered monocyclic aromatic heterocyclic group optionally substituted by 1 to 3 substituents selected from
    (a) a halogen atom,
    (b) a $C_{1-6}$ alkyl group optionally substituted by 1 to 3 substituents selected from
        (i) a halogen atom, and
        (ii) a $C_{1-6}$ alkoxy group,
    (c) a $C_{3-6}$ cycloalkyl group, and
    (d) a $C_{1-6}$ alkoxy group, or
(4) a 9- to 14-membered fused polycyclic non-aromatic heterocyclic group optionally substituted by 1 to 3 substituents selected from
    (a) a halogen atom, and
    (b) a $C_{1-6}$ alkyl group;
$R^3$ is an unsubstituted $C_{1-6}$ alkyl group;
$R^4$ is an unsubstituted $C_{1-6}$ alkyl group; and
Ring A is a benzene ring optionally further substituted by halogen atom(s);

[3] The compound or salt of the above-mentioned [1], wherein
$R^1$ is
(1) a hydrogen atom,
(2) a $C_{1-6}$ alkyl group optionally substituted by 1 to 3 $C_{3-6}$ cycloalkyl groups, or
(3) a $C_{3-6}$ cycloalkyl group;
$R^2$ is
(1) a $C_{6-10}$ aryl group optionally substituted by 1 to 3 substituents selected from
    (a) a $C_{1-6}$ alkoxy group, and
    (b) a 5- or 6-membered monocyclic aromatic heterocyclic group optionally substituted by 1 to 3 $C_{1-6}$ alkyl groups, or
(2) a 5- or 6-membered monocyclic aromatic heterocyclic group optionally substituted by 1 to 3 substituents selected from
    (a) a $C_{1-6}$ alkyl group optionally substituted by 1 to 3 $C_{1-6}$ alkoxy groups, and
    (b) a $C_{1-6}$ alkoxy group;
$R^3$ is an unsubstituted $C_{1-6}$ alkyl group;
$R^4$ is an unsubstituted $C_{1-6}$ alkyl group; and
Ring A is a benzene ring having no additional substituent other than formula: $-C(OH)R^3R^4$ wherein $R^3$ and $R^4$ are as defined above;

[4] 2-{3-[(3-Methoxy-1-methyl-1H-pyrazol-4-yl)amino]-1-methyl-1H-indazol-5-yl}propan-2-ol or a salt thereof;

[5] 2-{1-(Cyclopropylmethyl)-3-[(3-methoxy-1-methyl-1H-pyrazol-4-yl)amino]-1H-indazol-6-yl}propan-2-ol or a salt thereof;

[6] 2-{3-[2-Methoxy-4-(1-methyl-1H-pyrazol-4-yl)anilino]-1H-indazol-6-yl}propan-2-ol or a salt thereof;

[7] A medicament comprising the compound or salt of the above-mentioned [1];

[8] The medicament of the above-mentioned [7], which is a motor neuron degeneration inhibitor;

[9] The medicament of the above-mentioned [7], which is an agent for the prophylaxis or treatment of motor neuron disease;

[10] The medicament of the above-mentioned [9], wherein the motor neuron disease is amyotrophic lateral sclerosis or Friedreich's ataxia;

[11] The compound or salt of the above-mentioned [1] for use in the prophylaxis or treatment of motor neuron disease;

[12] The compound or salt of the above-mentioned [11], wherein the motor neuron disease is amyotrophic lateral sclerosis or Friedreich's ataxia;

[13] A method for inhibiting motor neuron degeneration in a mammal, which comprises administering an effective amount of the compound or salt of the above-mentioned [1] to the mammal;

[14] A method for preventing or treating a motor neuron disease in a mammal, which comprises administering an effective amount of the compound or salt of the above-mentioned [1] to the mammal;

[15] The method of the above-mentioned [14], wherein the motor neuron disease is amyotrophic lateral sclerosis or Friedreich's ataxia;

[16] Use of the compound or salt of the above-mentioned [1] for the manufacture of an agent for the prophylaxis or treatment of motor neuron disease;

[17] The use of the above-mentioned [16], wherein the motor neuron disease is amyotrophic lateral sclerosis or Friedreich's ataxia.

Effect of the Invention

According to the present invention, a compound having an excellent cell degeneration inhibitory action, particularly a motor neuron degeneration inhibitory action, which is useful as an agent for the prophylaxis or treatment of motor neuron diseases (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like, can be provided.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),

(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-p-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-6}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-11}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, a $C_{3-10}$ cycloalkane and a $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-p-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "cyclic group" include a "$C_{3-10}$ cycloalkyl group", a "$C_{3-10}$ cycloalkenyl group", a "$C_{6-14}$ aryl group" and a "heterocyclic group".

The definition of each symbol in the formula (I) is explained in detail.

$R^1$ is a hydrogen atom, an optionally substituted $C_{1-6}$ alkyl group, or an optionally substituted $C_{3-6}$ cycloalkyl group.

Examples of the substituent of the "optionally substituted $C_{1-6}$ alkyl group" and the "optionally substituted $C_{3-6}$ cycloalkyl group" represented by $R^1$ include those similar to Substituent Group A. The groups may have 1 to 3 substituents at substitutable positions.

$R^1$ is preferably
(1) a hydrogen atom,
(2) a $C_{1-6}$ alkyl group (e.g., methyl, ethyl, isopropyl) optionally substituted by 1 to 3 of optionally halogenated $C_{3-6}$ cycloalkyl groups (e.g., cyclopropyl, 2,2-difluorocyclopropyl), or
(3) a $C_{3-6}$ cycloalkyl group (e.g., cyclobutyl).

$R^1$ is more preferably
(1) a hydrogen atom,
(2) a $C_{1-6}$ alkyl group (e.g., methyl, isopropyl) optionally substituted by 1 to 3 $C_{3-6}$ cycloalkyl groups (e.g., cyclopropyl), or
(3) a $C_{3-6}$ cycloalkyl group (e.g., cyclobutyl).

$R^2$ is an optionally substituted $C_{1-6}$ alkyl group, or an optionally substituted cyclic group.

Examples of the substituent of the "optionally substituted $C_{1-6}$ alkyl group" and the "optionally substituted cyclic group" represented by $R^2$ include those similar to Substituent Group A. The groups may have 1 to 3 substituents at substitutable positions.

$R^2$ is preferably an optionally substituted cyclic group. $R^2$ is more preferably
(1) a $C_{3-6}$ cycloalkyl group (e.g., cyclohexyl),
(2) a $C_{6-10}$ aryl group (e.g., phenyl) optionally substituted by 1 to 3 substituents selected from
  (a) a halogen atom (e.g., a fluorine atom),
  (b) an optionally halogenated $C_{1-6}$ alkyl group (e.g., trifluoromethyl),
  (c) a $C_{1-6}$ alkoxy group (e.g., methoxy), and
  (d) a 5- or 6-membered monocyclic aromatic heterocyclic group (e.g., pyrazolyl (4-pyrazolyl)) optionally substituted by 1 to 3 $C_{1-6}$ alkyl groups (e.g., methyl),
(3) a 5- or 6-membered monocyclic aromatic heterocyclic group (e.g., pyrazolyl (3-pyrazolyl, 4-pyrazolyl, 5-pyrazolyl)) optionally substituted by 1 to 3 substituents selected from
  (a) a halogen atom (e.g., a chlorine atom),
  (b) a $C_{1-6}$ alkyl group (e.g., methyl, ethyl, isopropyl, isobutyl) optionally substituted by 1 to 3 substituents selected from
    (i) a halogen atom (e.g., a fluorine atom), and
    (ii) a $C_{1-6}$ alkoxy group (e.g., methoxy),
  (c) a $C_{3-6}$ cycloalkyl group (e.g., cyclobutyl), and
  (d) a $C_{1-6}$ alkoxy group (e.g., methoxy, ethoxy, isopropyloxy), or
(4) a 9- to 14-membered fused polycyclic non-aromatic heterocyclic group (e.g., dihydrobenzofuryl (2,3-dihydro-7-benzofuryl), tetrahydropyrazolopyridyl (4,5,6,7-tetrahydropyrazolo[1,5-a]-3-pyridyl), dihydropyrazolooxadinyl (6,7-dihydropyrazolo[5,1-b][1,3]-3-oxadinyl)) optionally substituted by 1 to 3 substituents selected from
  (a) a halogen atom (e.g., a fluorine atom), and
  (b) a $C_{1-6}$ alkyl group (e.g., methyl).

$R^2$ is particularly preferably,
(1) a $C_{6-10}$ aryl group (e.g., phenyl) optionally substituted by 1 to 3 substituents selected from
  (a) a $C_{1-6}$ alkoxy group (e.g., methoxy), and
  (b) a 5- or 6-membered monocyclic aromatic heterocyclic group (e.g., pyrazolyl (4-pyrazolyl)) optionally substituted by 1 to 3 $C_{1-6}$ alkyl groups (e.g., methyl), or
(2) a 5- or 6-membered monocyclic aromatic heterocyclic group (e.g., pyrazolyl (4-pyrazolyl)) optionally substituted by 1 to 3 substituents selected from
  (a) a $C_{1-6}$ alkyl group (e.g., methyl) optionally substituted by 1 to 3 $C_{1-6}$ alkoxy groups (e.g., methoxy), and
  (b) a $C_{1-6}$ alkoxy group (e.g., methoxy).

$R^3$ is an optionally substituted $C_{1-6}$ alkyl group.

Examples of the substituent of the "optionally substituted $C_{1-6}$ alkyl group" represented by $R^3$ include those similar to Substituent Group A. The group may have 1 to 3 substituents at substitutable positions.

$R^3$ is preferably an unsubstituted $C_{1-6}$ alkyl group.

$R^3$ is more preferably methyl.

$R^4$ is an optionally substituted $C_{1-6}$ alkyl group.

Examples of the substituent of the "optionally substituted $C_{1-6}$ alkyl group" represented by $R^4$ include those similar to Substituent Group A. The group may have 1 to 3 substituents at substitutable positions.

$R^4$ is preferably an unsubstituted $C_{1-6}$ alkyl group.

$R^4$ is more preferably methyl.

The position of the group represented by the formula: —C(OH)$R^3R^4$ wherein $R^3$ and $R^4$ are as defined above may be any of the 4- to 7-positoins on the benzene ring (Ring A) of the 1H-indazole ring. It is preferably the 5- or 6-position on the 1H-indazole ring.

Ring A is an optionally further substituted benzene ring.

The "benzene ring" of the "optionally further substituted benzene ring" represented by Ring A is optionally further substituted, in addition to a group represented by —C(OH)$R^3R^4$ wherein $R^3$ and $R^4$ are as defined above. Examples of the substituent include those similar to Substituent Group A. The ring may have 1 to 3 substituents at substitutable positions.

The substituent for Ring A other than the formula: —C(OH)$R^3R^4$ wherein $R^3$ and $R^4$ are as defined above is preferably a halogen atom (e.g., a fluorine atom).

The position of the substituent for Ring A other than the formula: —C(OH)$R^3R^4$ wherein $R^3$ and $R^4$ are as defined above is preferably the 4-, 5- or 7-position on the 1H-indazole ring.

Ring A preferably has no additional substituent other than formula: —C(OH)$R^3R^4$ wherein $R^3$ and $R^4$ are as defined above.

Compound (I) is preferably a compound wherein
$R^1$ is a hydrogen atom, an optionally substituted $C_{1-6}$ alkyl group, or an optionally substituted $C_{3-6}$ cycloalkyl group;
$R^2$ is an optionally substituted cyclic group;
$R^3$ is an optionally substituted $C_{1-6}$ alkyl group;
$R^4$ is an optionally substituted $C_{1-6}$ alkyl group; and
Ring A is an optionally further substituted benzene ring.

Compound (I) is more preferably a compound wherein
$R^1$ is
(1) a hydrogen atom,
(2) a $C_{1-6}$ alkyl group (e.g., methyl, ethyl, isopropyl) optionally substituted by 1 to 3 of optionally halogenated $C_{3-6}$ cycloalkyl groups (e.g., cyclopropyl, 2,2-difluorocyclopropyl), or
(3) a $C_{3-6}$ cycloalkyl group (e.g., cyclobutyl);
$R^2$ is
(1) a $C_{3-6}$ cycloalkyl group (e.g., cyclohexyl),
(2) a $C_{6-10}$ aryl group (e.g., phenyl) optionally substituted by 1 to 3 substituents selected from
(a) a halogen atom (e.g., a fluorine atom),
(b) an optionally halogenated $C_{1-6}$ alkyl group (e.g., trifluoromethyl),
(c) a $C_{1-6}$ alkoxy group (e.g., methoxy), and
(d) a 5- or 6-membered monocyclic aromatic heterocyclic group (e.g., pyrazolyl (4-pyrazolyl)) optionally substituted by 1 to 3 $C_{1-6}$ alkyl groups (e.g., methyl), (3) a 5- or 6-membered monocyclic aromatic heterocyclic group (e.g., pyrazolyl (3-pyrazolyl, 4-pyrazolyl, 5-pyrazolyl)) optionally substituted by 1 to 3 substituents selected from
(a) a halogen atom (e.g., a chlorine atom),
(b) a $C_{1-6}$ alkyl group (e.g., methyl, ethyl, isopropyl, isobutyl) optionally substituted by 1 to 3 substituents selected from
(i) a halogen atom (e.g., a fluorine atom), and
(ii) a $C_{1-6}$ alkoxy group (e.g., methoxy),
(c) a $C_{3-6}$ cycloalkyl group (e.g., cyclobutyl), and
(d) a $C_{1-6}$ alkoxy group (e.g., methoxy, ethoxy, isopropyloxy), or
(4) a 9- to 14-membered fused polycyclic non-aromatic heterocyclic group (e.g., dihydrobenzofuryl (2,3-dihydro-7-benzofuryl), tetrahydropyrazolopyridyl (4,5,6,7-tetrahydropyrazolo[1,5-a]-3-pyridyl), dihydropyrazolooxadinyl (6,7-dihydropyrazolo[5,1-b][1,3]-3-oxadinyl)) optionally substituted by 1 to 3 substituents selected from
(a) a halogen atom (e.g., a fluorine atom), and
(b) a $C_{1-6}$ alkyl group (e.g., methyl);
$R^3$ is an unsubstituted $C_{1-6}$ alkyl group (e.g., methyl);
$R^4$ is an unsubstituted $C_{1-6}$ alkyl group (e.g., methyl); and
Ring A is a benzene ring optionally further substituted by halogen atom(s) (e.g., a fluorine atom).

Compound (I) is particularly preferably a compound wherein
$R^1$ is
(1) a hydrogen atom,
(2) a $C_{1-6}$ alkyl group (e.g., methyl, isopropyl) optionally substituted by 1 to 3 $C_{3-6}$ cycloalkyl groups (e.g., cyclopropyl), or
(3) a $C_{3-6}$ cycloalkyl group (e.g., cyclobutyl);
$R^2$ is
(1) a $C_{6-10}$ aryl group (e.g., phenyl) optionally substituted by 1 to 3 substituents selected from
(a) a $C_{1-6}$ alkoxy group (e.g., methoxy), and
(b) a 5- or 6-membered monocyclic aromatic heterocyclic group (e.g., pyrazolyl (4-pyrazolyl)) optionally substituted by 1 to 3 $C_{1-6}$ alkyl groups (e.g., methyl), or
(2) a 5- or 6-membered monocyclic aromatic heterocyclic group (e.g., pyrazolyl (4-pyrazolyl)) optionally substituted by 1 to 3 substituents selected from
(a) a $C_{1-6}$ alkyl group (e.g., methyl) optionally substituted by 1 to 3 $C_{1-6}$ alkoxy groups (e.g., methoxy), and
(b) a $C_{1-6}$ alkoxy group (e.g., methoxy);
$R^3$ is an unsubstituted $C_{1-6}$ alkyl group (e.g., methyl);
$R^4$ is an unsubstituted $C_{1-6}$ alkyl group (e.g., methyl); and
Ring A is a benzene ring having no additional substituent other than formula: —C(OH)$R^3R^4$ wherein $R^3$ and $R^4$ are as defined above.

As another embodiment, compound (I) is preferably compound (Ia) represented by the formula

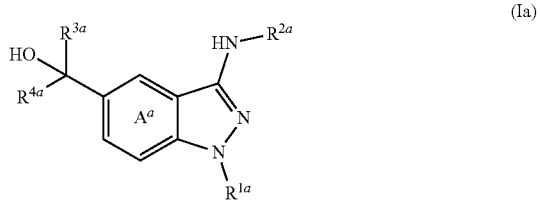

wherein
R^1a is
(1) a $C_{1-6}$ alkyl group (e.g., methyl, isopropyl) optionally substituted by 1 to 3 of optionally halogenated $C_{3-6}$ cycloalkyl groups (e.g., cyclopropyl, 2,2-difluorocyclopropyl), or
(2) a $C_{3-6}$ cycloalkyl group (e.g., cyclobutyl);
R^2a is
(1) a $C_{3-6}$ cycloalkyl group (e.g., cyclohexyl),
(2) a 5- or 6-membered monocyclic aromatic heterocyclic group (e.g., pyrazolyl (4-pyrazolyl)) optionally substituted by 1 to 3 substituents selected from
  (a) a halogen atom (e.g., a chlorine atom),
  (b) a $C_{1-6}$ alkyl group (e.g., methyl, isopropyl, isobutyl) optionally substituted by 1 to 3 $C_{1-6}$ alkoxy groups (e.g., methoxy),
  (c) a $C_{3-6}$ cycloalkyl group (e.g., cyclobutyl), and
  (d) a $C_{1-6}$ alkoxy group (e.g., methoxy), or
(3) a 9- to 14-membered fused polycyclic non-aromatic heterocyclic group (e.g., dihydropyrazolooxadinyl (6,7-dihydropyrazolo[5,1-b][1,3]-3-oxadinyl)) optionally substituted by 1 to 3 halogen atoms (e.g., a fluorine atom);
R^3a is an unsubstituted $C_{1-6}$ alkyl group (e.g., methyl);
R^4a is an unsubstituted $C_{1-6}$ alkyl group (e.g., methyl); and
Ring A^a is a benzene ring having no additional substituent, or compound (Ib) represented by the formula

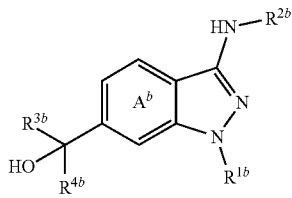

(Ib)

wherein
R^1b is
(1) a hydrogen atom,
(2) a $C_{1-6}$ alkyl group (e.g., methyl, ethyl, isopropyl) optionally substituted by 1 to 3 of optionally halogenated $C_{3-6}$ cycloalkyl groups (e.g., cyclopropyl, 2,2-difluorocyclopropyl), or
(3) a $C_{3-6}$ cycloalkyl group (e.g., cyclobutyl);
R^2b is
(1) a $C_{6-10}$ aryl group (e.g., phenyl) optionally substituted by 1 to 3 substituents selected from
  (a) a halogen atom (e.g., a fluorine atom),
  (b) an optionally halogenated $C_{1-6}$ alkyl group (e.g., trifluoromethyl),
  (c) a $C_{1-6}$ alkoxy group (e.g., methoxy), and
  (d) a 5- or 6-membered monocyclic aromatic heterocyclic group (e.g., pyrazolyl (4-pyrazolyl)) optionally substituted by 1 to 3 $C_{1-6}$ alkyl groups (e.g., methyl),
(2) a 5- or 6-membered monocyclic aromatic heterocyclic group (e.g., pyrazolyl (3-pyrazolyl, 4-pyrazolyl, 5-pyrazolyl)) optionally substituted by 1 to 3 substituents selected from
  (a) a halogen atom (e.g., a chlorine atom),
  (b) a $C_{1-6}$ alkyl group (e.g., methyl, ethyl, isopropyl, isobutyl) optionally substituted by 1 to 3 substituents selected from
    (i) a halogen atom (e.g., a fluorine atom), and
    (ii) a $C_{1-6}$ alkoxy group (e.g., methoxy), and (c) a $C_{1-6}$ alkoxy group (e.g., methoxy, ethoxy, isopropyloxy), or
(3) a 9- to 14-membered fused polycyclic non-aromatic heterocyclic group (e.g., dihydrobenzofuryl (2,3-dihydro-7-benzofuryl), tetrahydropyrazolopyridyl (4,5,6,7-tetrahydropyrazolo[1,5-a]-3-pyridyl), dihydropyrazolooxadinyl (6,7-dihydropyrazolo[5,1-b][1,3]-3-oxadinyl)) optionally substituted by 1 to 3 $C_{1-6}$ alkyl groups (e.g., methyl);
R^3b is an unsubstituted $C_{1-6}$ alkyl group (e.g., methyl);
R^4b is an unsubstituted $C_{1-6}$ alkyl group (e.g., methyl); and
Ring A^b is a benzene ring optionally further substituted by halogen atom(s) (e.g., a fluorine atom) at the 4-, 5- or 7-position on the 1H-indazole ring.

As another embodiment, compound (I) is more preferably compound (Ia) represented by

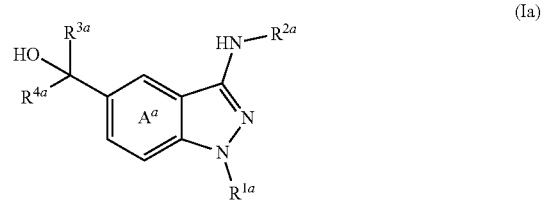

(Ia)

wherein
R^1a is a $C_{1-6}$ alkyl group (e.g., methyl);
R^2a is a 5- or 6-membered monocyclic aromatic heterocyclic group (e.g., pyrazolyl (4-pyrazolyl)) optionally substituted by 1 to 3 substituents selected from a $C_{1-6}$ alkyl group (e.g., methyl) and a $C_{1-6}$ alkoxy group (e.g., methoxy);
R^3a is an unsubstituted $C_{1-6}$ alkyl group (e.g., methyl);
R^4a is an unsubstituted $C_{1-6}$ alkyl group (e.g., methyl); and
Ring A^a is a benzene ring having no additional substituent, or compound (Ib) represented by the formula

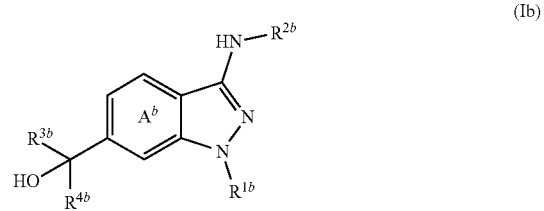

(Ib)

wherein
R^1b is
(1) a hydrogen atom,
(2) a $C_{1-6}$ alkyl group (e.g., methyl, isopropyl) optionally substituted by 1 to 3 $C_{3-6}$ cycloalkyl groups (e.g., cyclopropyl), or
(3) a $C_{3-6}$ cycloalkyl group (e.g., cyclobutyl);
R^2b is
(1) a $C_{6-10}$ aryl group (e.g., phenyl) optionally substituted by 1 to 3 substituents selected from
  (a) a $C_{1-6}$ alkoxy group (e.g., methoxy), and
  (b) a 5- or 6-membered monocyclic aromatic heterocyclic group (e.g., pyrazolyl (4-pyrazolyl)) optionally substituted by 1 to 3 $C_{1-6}$ alkyl groups (e.g., methyl), or (2) a 5- or 6-membered monocyclic aromatic heterocyclic group (e.g., pyrazolyl (4-pyrazolyl)) optionally substituted by 1 to 3 substituents selected from
  (a) a $C_{1-6}$ alkyl group (e.g., methyl) optionally substituted by 1 to 3 $C_{1-6}$ alkoxy groups (e.g., methoxy), and
  (b) a $C_{1-6}$ alkoxy group (e.g., methoxy);
$R^{3b}$ is an unsubstituted $C_{1-6}$ alkyl group (e.g., methyl);
$R^{4b}$ is an unsubstituted $C_{1-6}$ alkyl group (e.g., methyl); and
Ring $A^b$ is a benzene ring having no additional substituent.

Specific examples of compound (I) include the compounds of Examples 1 to 89.

Among them, compound (I) is preferably
2-{3-[2-methoxy-4-(1-methyl-1H-pyrazol-4-yl)anilino]-1H-indazol-6-yl}propan-2-ol (Example 12) or a salt thereof,
2-{3-[(3-methoxy-1-methyl-1H-pyrazol-4-yl)amino]-1-methyl-1H-indazol-5-yl}propan-2-ol (Example 41) or a salt thereof,
2-{1-(cyclopropylmethyl)-3-[(3-methoxy-1-methyl-1H-pyrazol-4-yl)amino]-1H-indazol-6-yl}propan-2-ol (Example 49) or a salt thereof,
2-(1-cyclobutyl-3-{[3-(methoxymethyl)-1-methyl-1H-pyrazol-4-yl]amino}-1H-indazol-6-yl)propan-2-ol (Example 82) or a salt thereof,
2-[1-(cyclopropylmethyl)-3-{[3-(methoxymethyl)-1-methyl-1H-pyrazol-4-yl]amino}-1H-indazol-6-yl]propan-2-ol (Example 84) or a salt thereof, or
2-[3-{[3-(methoxymethyl)-1-methyl-1H-pyrazol-4-yl]amino}-1-(propan-2-yl)-1H-indazol-6-yl]propan-2-ol (Example 85) or a salt thereof.

Compound (I) is particularly preferably
2-{3-[2-methoxy-4-(1-methyl-1H-pyrazol-4-yl)anilino]-1H-indazol-6-yl}propan-2-ol (Example 12) or a salt thereof,
2-{3-[(3-methoxy-1-methyl-1H-pyrazol-4-yl)amino]-1-methyl-1H-indazol-5-yl}propan-2-ol (Example 41) or a salt thereof, or
2-{1-(cyclopropylmethyl)-3-[(3-methoxy-1-methyl-1H-pyrazol-4-yl)amino]-1H-indazol-6-yl}propan-2-ol (Example 49) or a salt thereof.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt, barium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^{2}H$, $^{3}H$, $^{11}C$, $^{14}C$, $^{18}F$, $^{35}S$, $^{125}I$, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like; amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like; esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of a functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When alkylation reaction is carried out in each step, a combination of an electrophile (e.g., an alkyl halide etc.) and a base (e.g., an organic base, an inorganic base, a metal alkoxide, a metal amide etc.) is used as a reagent.

Compound (I) can be synthesized according to the following Production Methods A to L or a method analogous thereto. Each symbol in the formulas of the schemes is as defined above, unless otherwise specified. HAL is a halogen atom (e.g., a chlorine atom, a bromine atom, an iodine atom). $R^9$ is an optionally substituted $C_{1-6}$ alkyl group (e.g., methyl, ethyl). $R^{10}$ is a hydrogen atom or a substituent.

Moreover, when desired, compound (I) can be synthesized by performing deprotection reaction, amidation reaction, urea formation, alkylation reaction, Mitsunobu reaction, oxidation reaction, reduction reaction, halogenation reaction, coupling reaction, nucleophilic addition reaction by a carbo anion, Grignard reaction, dehydration reaction and the like singly or two or more thereof in combination.

Compound (I) can be produced from compound (1) and each starting material derived from compound (1) according to the methods shown in the following Scheme 1 to 4. In the formulas, HAL is a halogen atom (e.g., a chlorine atom, a bromine atom, an iodine atom), $R^9$ is an optionally substituted $C_{1-6}$ alkyl group (e.g., methyl, ethyl), $P^1$ is a protecting group, and the other symbols are as defined above.

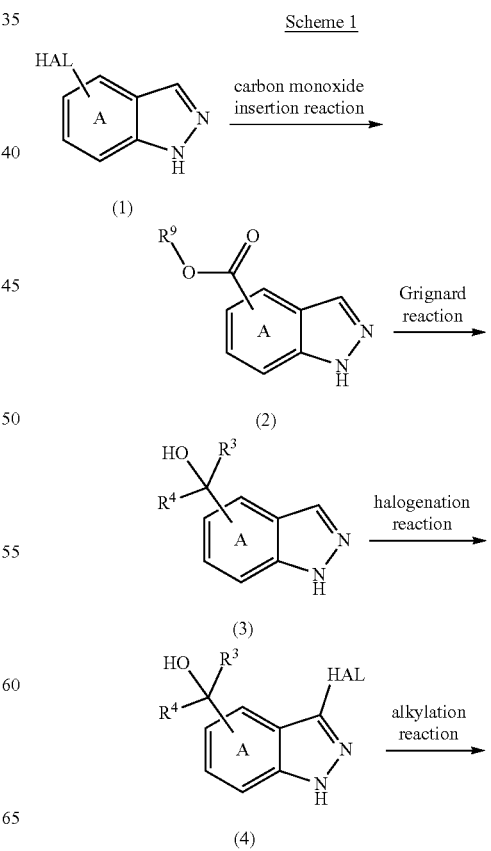

Scheme 1

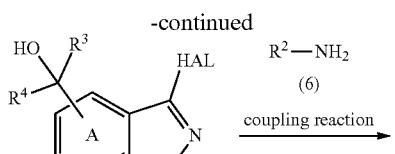

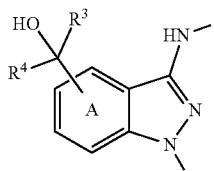

Compound (1) may be commercially easily available or can be produced according to a method known per se.

Compound (2) can be produced by subjecting compound (1) to a carbon monoxide insertion reaction in the presence of a metal catalyst. Examples of the metal catalyst to be used include palladium compounds such as palladium(II) acetate, tetrakis(triphenylphosphine)palladium(0), dichlorobis (triphenylphosphine)palladium(II), dichlorobis(triethylphosphine)palladium(II), tris(dibenzylideneacetone)dipalladium (0), 1,1'-bis (diphenylphosphino) ferrocenepalladium(II) chloride and the like, and the like. In addition, a base may be added to the reaction system. Examples of such base include organic bases such as triethylamine, diisopropylethylamine and the like, and the like. An alcohol ($R^9$—OH) such as methanol, ethanol and the like is used as a reaction solvent, and the substituent $R^9$ of the alcohol is introduced as a substituent on the ester group of compound (2).

Compound (3) can be produced by subjecting compound (2) to Grignard reaction. Examples of the Grignard reagent include alkylmagnesium halides such as methylmagnesium bromide and the like. The Grignard reagent can be prepared according to a method known per se, for example, by reacting the alkyl halide corresponding to $R^3$ and/or $R^4$ with a metal magnesium in a solvent of ether or tetrahydrofuran, or commercially available Grignard reagent solution can be used directly.

Compound (4) can be produced by subjecting compound (3) to a halogenation reaction. Examples of the halogenating agent to be used include N-iodosuccinimide, N-bromosuccinimide (NBS), N-chlorosuccinimide (NCS), bromine, sulfuryl chloride, iodine and the like. In addition, the reaction can be accelerated by adding an inorganic base such as sodium hydroxide, potassium hydroxide and the like to the reaction system.

Compound (5) can be produced by subjecting compound (4) to an alkylation reaction. As the reaction reagent, a combination of an electrophile (e.g., an alkyl halide, a cycloalkyl halide etc.) corresponding to $R^1$ and a base (e.g., organic bases, inorganic bases, metal alkoxides, metal amides etc.) can be used. The electrophile may be commercially easily available or can be produced according to a method known per se.

Compound (I) can be produced by subjecting compound (5) to a coupling reaction with compound (6). Examples of the metal catalyst to be used in the coupling reaction include palladium compounds such as palladium(II) acetate, tetrakis (triphenylphosphine)palladium(0), dichlorobis(triphenylphosphine)palladium(II), dichlorobis(triethylphosphine)palladium(II), tris(dibenzylideneacetone)dipalladium (0), 1,1'-bis(diphenylphosphino)ferrocenepalladium(II) chloride and the like; nickel compounds such as tetrakis (triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base may be added to the reaction system. Examples of such base include inorganic bases and the like. Compound (6) may be commercially easily available or can be produced according to a method known per se.

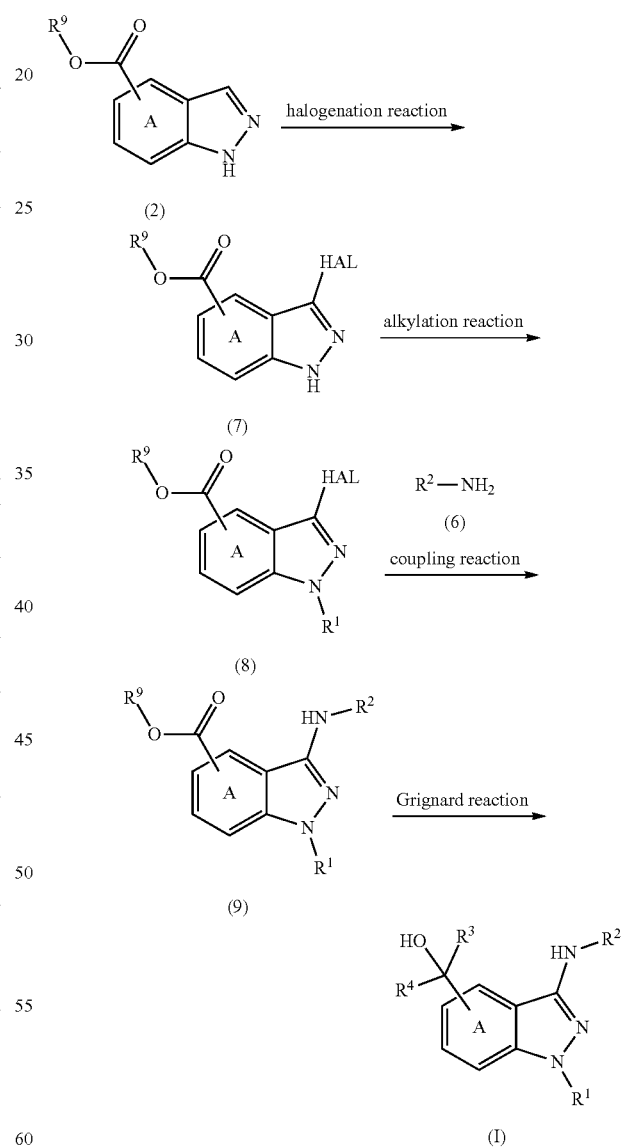

Compound (7) can be produced by subjecting compound (2) to a halogenation reaction. Examples of the halogenating agent to be used include N-iodosuccinimide, N-bromosuccinimide (NBS), N-chlorosuccinimide (NCS), bromine, sulfuryl chloride, iodine and the like. In addition, the reaction can be accelerated by adding an inorganic base such as sodium hydroxide, potassium hydroxide and the like to the reaction system.

Compound (8) can be produced by subjecting compound (7) to an alkylation reaction. As the reaction reagent, a combination of an electrophile (e.g., an alkyl halide, a cycloalkyl halide etc.) corresponding to $R^1$ and a base (e.g., organic bases, inorganic bases, metal alkoxides, metal amides etc.) can be used. The electrophile may be commercially easily available or can be produced according to a method known per se.

Compound (9) can be produced by subjecting compound (8) to a coupling reaction with compound (6). Examples of the metal catalyst to be used in the coupling reaction include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base may be added to the reaction system. Examples of such base include inorganic bases and the like. Compound (6) may be commercially easily available or can be produced according to a method known per se.

Compound (I) can be produced by subjecting compound (9) to Grignard reaction. Examples of the Grignard reagent include alkylmagnesium halides such as methylmagnesium bromide and the like. The Grignard reagent can be prepared according to a method known per se, for example, by reacting the alkyl halide corresponding to $R^3$ and/or $R^4$ with a metal magnesium in a solvent of ether or tetrahydrofuran, or commercially available Grignard reagent solution can be used directly.

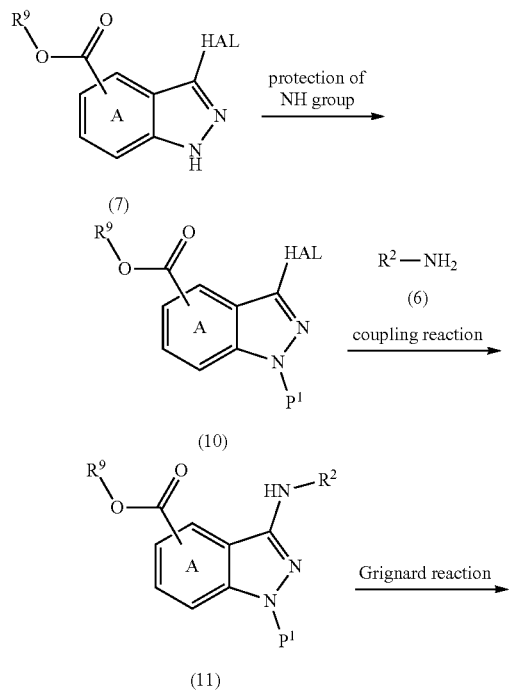

Scheme 3

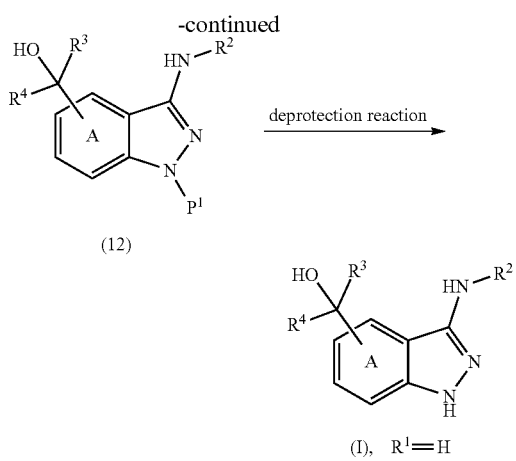

Compound (10) can be produced by subjecting compound (7) to a protection reaction of an NH group. Examples of the protecting group include a methoxymethyl group, a benzyl group, a tert-butyldimethylsilyl group, a tetrahydropyranyl group and the like. These protecting group can be introduced into the NH group of compound (7) according to a method known per se or a method analogous thereto.

Compound (11) can be produced by subjecting compound (10) to a coupling reaction with compound (6). Examples of the metal catalyst to be used in the coupling reaction include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis (diphenylphosphino) ferrocenepalladium(II) chloride and the like; nickel compounds such as tetrakis(triphenylphosphine)nickel(0) and the like; rhodium compounds such as tris (triphenylphosphine) rhodium(III) chloride and the like; cobalt compounds; copper compounds such as copper oxide, copper(I) iodide and the like; platinum compounds and the like. In addition, a base may be added to the reaction system. Examples of such base include inorganic bases and the like. Compound (6) may be commercially easily available or can be produced according to a method known per se.

Compound (12) can be produced by subjecting compound (11) to Grignard reaction. Examples of the Grignard reagent include alkylmagnesium halides such as methylmagnesium bromide and the like. The Grignard reagent can be prepared according to a method known per se, for example, by reacting the alkyl halide corresponding to $R^3$ and/or $R^4$ with a metal magnesium in a solvent of ether or tetrahydrofuran, or commercially available Grignard reagent solution can be used directly.

Compound (I) wherein $R^1$ is hydrogen can be produced by subjecting compound (12) to a deprotection reaction.

Scheme 4

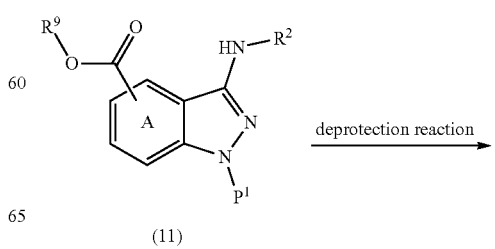

-continued

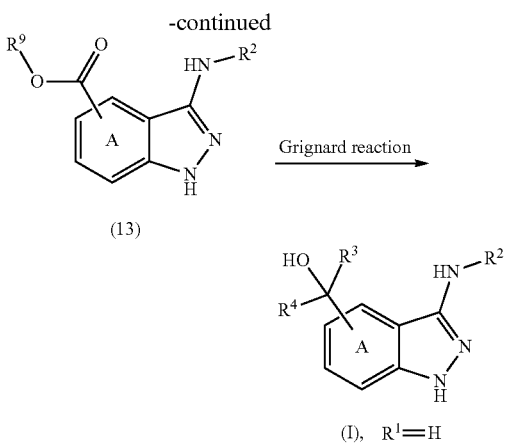

(13)

(I), R¹=H

Compound (13) can be produced by subjecting compound (11) to a deprotection reaction.

Compound (I) wherein $R^1$ is hydrogen can be produced by subjecting compound (13) to Grignard reaction. Examples of the Grignard reagent include alkylmagnesium halides such as methylmagnesium bromide and the like. The Grignard reagent can be prepared according to a method known per se, for example, by reacting the alkyl halide corresponding to $R^3$ and/or $R^4$ with a metal magnesium in a solvent of ether or tetrahydrofuran, or commercially available Grignard reagent solution can be used directly.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form or S-form and R-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

The compound of the present invention is expected to be useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, epilepsy, anxiety disorder, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, depressive disorder, catalepsy, hebephrenic schizophrenia, paranoid schizophrenia], (2) neurodegenerative diseases [e.g., progressive bulbar paralysis, progressive muscular atrophy, primary lateral sclerosis, progressive pseudobulbar paralysis, spinal muscular atrophy, Alzheimer's disease, Alzheimer-type senile dementia, Parkinson's disease, Huntington's disease, multi-infarct dementia, frontotemporal dementia, dementia Parkinson's type, progressive supranuclear palsy, Pick's syndrome, corticobasal degeneration, Down's disease, vascular dementia, postencephalitic parkinsonism, Lewy body dementia, multiple-system atrophy, Friedreich's ataxia, HIV dementia, amyotrophic lateral sclerosis (ALS), motor neurogenesis disease (MND), Creutzfeldt-Jakob disease or prion disease, cerebral palsy, progressive supranuclear palsy, traumatic brain injury, glaucoma, multiple sclerosis, neuromyelitis optica (NMO), postoperative cognitive dysfunction (POCD), postoperative delirium (POD), delirium], (3) age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome],
(5) respiratory depression caused by anesthetics, traumatic disease, or neurodegenerative disease and the like,
(6) traumatic brain injury, cerebral apoplexy, cerebral edema, cerebral ischemia, ischemia, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, neoplasms (e.g., cancer, liver neoplasms, colonic neoplasms, breast neoplasms, prostatic neoplasms, neuroblastoma, bone neoplasms, mouth neoplasms, mastocytoma, cholangiocarcinoma, Lewis lung carcinoma etc.), immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, diarrhea, constipation, postoperative ileus, rheumatoid arthritis, osteoarthritis, functional dyspepsia, hyperalgesia, insulin resistance, dementia pugilistica, nausea, vomiting, neoplasm metastasis, brain injuries, seizure, body weight changes, weight gain, weight loss, colitis, alcoholism, hypothermia, fatty liver, nonalcoholic steatohepatitis (NASH), liver cirrhosis, atherosclerosis, infection, muscle spasticity, hypertension, stroke, malignant migrating partial seizures of infancy, diabetes mellitus, type 2 diabetes mellitus, dyslipidaemia, visceral obesity, ocular hypotension, anorexia, fibrosis, myocardial infarction, cachexia, induced psychotic disorder, ataxia, AIDS wasting syndrome, cirrhotic cardiomyopathy, uremic pruritus, neurobehavioral manifestations, Tubulointerstitial nephritis and uveitis syndrome, interstitial cystitis, retinitis pigmentosa, autoimmune diseases, coronary artery disease, aspirin-induced asthma, platelet storage pool deficiency, diabetic embryopathy, Arthus type urticaria, asthma, toxic oil syndrome, otitis and the like,
(7) pain (e.g., inflammatory pain, cancerous pain, neuropathic pain, acute pain, pain associated with peripheral neuropathy, central pain, fibromyalgia, vassooclussive painful crises in sickle cell disease, multiple sclerosis-mediated spasticity or pain, functional chest pain, complex regional pain syndrome etc.),
(8) lysosome diseases [e.g., Gaucher's disease, Krabbe's disease, Niemann-Pick syndrome]
and the like.

Since the compound of the present invention has an excellent cell degeneration inhibitory action, a superior prophylactic or therapeutic effect for the above-mentioned diseases may be expected.

Since the compound of the present invention also has an excellent motor neuron degeneration inhibitory action, a superior prophylactic or therapeutic effect for motor neuron diseases (motor neuron neurodegenerative diseases) (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like may be expected.

Compound (I) can be used as a prodrug.

A prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity etc.). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with amyotrophic lateral sclerosis (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonicity agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrochloride etc.), 5-$HT_3$ antagonist (Cyamemazine etc.), heart non-selective β inhibitor (propranolol hydrochloride, oxprenolol hydrochloride etc.), histamine Hi antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin Via antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, zonisamide, entacapone, amantadine, talipexole, pramipexole, apomorphine, cabergoline, bromocriptine, istradefylline, trihexyphenidyl, promethazine, pergolide, etc.), therapeutic drug for Huntington's disease (chlorpromazine hydrochloride, haloperidol, reserpine etc.), therapeutic drug for Gaucher's disease (imiglucerase, taliglucerase alfa, velaglucerase alfa, eliglustat, miglustat, etc.), therapeutic drug for ALS (riluzole etc., neurotrophic factor etc.), therapeutic drug for multiple sclerosis (molecular target drug such as fingolimod, interferon beta 1b, natalizumab and the like, etc.), antiepilepsy drug (phenytoin, carbamazepine, phenobarbital, primidone, zonisamide, sodium valproate, ethosuximide, diazepam, nitrazepam, clonazepam, clobazam, gabapentin, topiramate, lamotrigine, levetiracetam, stiripentol, rufinamide, etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as
  (1) the dose can be reduced as compared to single administration of the compound of the present invention or a concomitant drug,
  (2) the drug to be combined with the compound of the present invention can be selected according to the condition of patients (mild case, severe case and the like),
  (3) the period of treatment can be set longer by selecting a concomitant drug having different action and mechanism from the compound of the present invention,
  (4) a sustained treatment effect can be designed by selecting a concomitant drug having different action and mechanism from the compound of the present invention,
  (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of the combination agent of the present invention include those similar to the above-mentioned carriers.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution in column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as a developing solvent, and UV detector was used for the detection. In silica gel column chromatography, the indication of NH means use of aminopropylsilane-bonded silica gel.

In preparative HPLC (high performance liquid chromatography) in Example, any of the following solvents was employed as an elution solvent system used for purification of the compound unless otherwise specified.

- a mixed solvent system of acetonitrile/water containing 0.1% trifluoroacetic acid
- a mixed solvent system of acetonitrile/water containing 10 mM ammonium bicarbonate
- a mixed solvent system of acetonitrile/water containing 0.05% ammonia For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method or APCI method was used. The data indicates actual measured value (found). While molecular ion peak is generally observed, a fragment ion is sometimes observed. In the case of a salt, a molecular ion peak or fragment ion peak of free form is generally observed.

In the following Examples, the following abbreviations are used.

MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
$Pd_2(dba)_3$: tris(dibenzylideneacetone)dipalladium(0)
$Pd(OAc)_2$: palladium(II) acetate
$PdCl_2$(dppf): [1,1'-bis(diphenylphosphino)ferrocene]palladium(II) dichloride
BrettPhos Pd G3: [(2-dicyclohexylphosphino-3,6-dimethoxy-2',4',6'-triisopropyl-1,1'-biphenyl)-2-(2'-amino-1,1'-biphenyl)]palladium(II) methanesulfonate
BrettPhos: 2-(dicyclohexylphosphino)-3,6-dimethoxy-2',4',6'-triisopropyl-1,1'-biphenyl
NaO$^t$Bu: sodium tert-butoxide
XPhos Pd G3: (2-dicyclohexylphosphino-2',4',6'-triisopropyl-1,1'-biphenyl) [2-(2'-amino-1,1'-biphenyl)]palladium(II) methanesulfonate
CuI: copper(I) iodide
XANTPHOS: (9,9-dimethyl-9H-xanthene-4,5-diyl)bis(diphenylphosphine)
TFA: trifluoroacetic acid
IPE: diisopropyl ether
DMF: N,N-dimethylformamide
THF: tetrahydrofuran
DME: 1,2-dimethoxyethane
MeOH: methanol
EtOH: ethanol
DMSO: dimethyl sulfoxide
$Et_2O$: diethyl ether
SFC: supercritical fluid chromatography

Example 1

2-{3-[2-methoxy-5-(trifluoromethyl)anilino]-1H-indazol-6-yl}propan-2-ol

A) methyl 3-[2-methoxy-5-(trifluoromethyl)anilino]-1-(oxan-2-yl)-1H-indazole-6-carboxylate A mixture of methyl 3-iodo-1-(oxan-2-yl)-1H-indazole-6-carboxylate (300 mg), 2-methoxy-5-(trifluoromethyl)aniline (180 mg), $Pd_2(dba)_3$ (36.7 mg), XANTPHOS (45.0 mg), cesium carbonate (770 mg) and DME (6.0 ml) was heated overnight at 90° C. The insoluble substance was removed by filtration through Celite, and the filtrate was concentrated under reduced pressure. The residue was purified by silica gel column chromatography (hexane/ethyl acetate) to give the title compound (273 mg).

MS: [M+H]$^+$ 450.1.

B) 2-{3-[2-methoxy-5-(trifluoromethyl)anilino]-1-(oxan-2-yl)-1H-indazol-6-yl}propan-2-ol To a mixture of methylmagnesium bromide (1 mol/l, THF solution) (2.0 ml) and THF (2.0 ml) was added methyl 3-[2-methoxy-5-(trifluoromethyl)anilino]-1-(oxan-2-yl)-1H-indazole-6-carboxylate (100 mg) at 0° C., and the mixture was stirred under nitrogen atmosphere at 40° C. for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure to give the title compound (98 mg).

MS: [M+H]$^+$ 450.1.

C) 2-{3-[2-methoxy-5-(trifluoromethyl)anilino]-1H-indazol-6-yl}propan-2-ol

To a mixture of 2-{3-[2-methoxy-5-(trifluoromethyl)anilino]-1-(oxan-2-yl)-1H-indazol-6-yl}propan-2-ol and EtOH (2.0 ml) was added 6 mol/l hydrochloric acid (0.30 ml) at room temperature, and the mixture was stirred at 50° C. for 2 hr. To the reaction mixture was added saturated aqueous sodium hydrogencarbonate solution, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate), and the fraction was concentrated under reduced pressure. The obtained residue was crystallized from ethyl acetate/hexane to give the title compound (30.1 mg).

$^1$H NMR (300 MHz, DMSO-$d_6$) δ 1.48 (6H, s), 4.00 (3H, s), 5.10 (1H, s), 7.11-7.20 (3H, m), 7.48 (1H, s), 7.86 (1H, d, J=8.7 Hz), 8.01 (1H, s), 8.54 (1H, s), 12.17 (1H, s).

Example 2

2-{3-[(2,3-dihydro-1-benzofuran-7-yl)amino]-1-methyl-1H-indazol-6-yl}propan-2-ol A) methyl 3-iodo-1-methyl-1H-indazole-6-carboxylate To a mixture of methyl 3-iodo-1H-indazole-6-carboxylate (11.5 g) and DMF (69 ml) was added cesium carbonate (17.37 g), and the mixture was stirred at room temperature for 30 min. To the reaction mixture was added dropwise a mixture of iodomethane (7.14 ml) and DMF (23 ml), and the mixture was stirred overnight at room temperature. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (8.63 g).

MS: [M+H]$^+$ 316.8.

B) methyl 3-[(2,3-dihydro-1-benzofuran-7-yl)amino]-1-methyl-1H-indazole-6-carboxylate A mixture of methyl 3-iodo-1-methyl-1H-indazole-6-carboxylate (3 g), 2,3-dihydro-1-benzofuran-7-amine (1.54 g), cesium carbonate (6.18 g), XANTPHOS (1.10 g), Pd(OAc)$_2$ (0.21 g) and toluene (40 ml) was stirred overnight under nitrogen atmosphere at 80° C. The insoluble substance was removed by filtration through Celite, and the filtrate was concentrated under reduced pressure. The residue was purified by silica gel column chromatography (hexane/ethyl acetate) to give the title compound (2.02 g).

MS: [M+H]$^+$ 324.0.

C) 2-{3-[(2,3-dihydro-1-benzofuran-7-yl)amino]-1-methyl-1H-indazol-6-yl}propan-2-ol To a mixture of methylmagnesium bromide (1 mol/l THF solution) (2.0 ml) and THF (2.0 ml) was added methyl 3-[(2,3-dihydro-1-benzofuran-7-yl)amino]-1-methyl-1H-indazole-6-carboxylate (100 mg) at 0° C., and the mixture was stirred under nitrogen atmosphere at 40° C. for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (67 mg).

$^1$H NMR (400 MHz, DMSO-$d_6$) δ 1.49 (6H, s), 3.23 (2H, t, J=8.8 Hz), 3.87 (3H, s), 4.60 (2H, t, J=8.7 Hz), 5.07 (1H, s), 6.72-6.79 (2H, m), 7.10 (1H, d, J=8.6 Hz), 7.48 (1H, s), 7.78-7.87 (3H, m).

Example 3

2-(3-{[1-(difluoromethyl)-5-methyl-1H-pyrazol-4-yl]amino}-1-methyl-1H-indazol-6-yl)propan-2-ol A) 1-(difluoromethyl)-5-methyl-4-nitro-1H-pyrazole A mixture of 3-methyl-4-nitro-1H-pyrazole (5 g), cesium carbonate (12.82 g) and DMF (50 ml) was stirred at 120° C. for 20 min. Sodium 2-chloro-2,2-difluoroacetate (12 g) was added thereto at 120° C., and the mixture was stirred for 10 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (1.55 g).

$^1$H NMR (400 MHz, DMSO-$d_6$) δ 2.77 (3H, s), 8.00 (1H, t, J=56.7 Hz), 8.50 (1H, s).

B) 1-(difluoromethyl)-5-methyl-1H-pyrazol-4-amine

To a mixture of 1-(difluoromethyl)-5-methyl-4-nitro-1H-pyrazole (50 mg) and THF (1 ml) were added zinc powder (185 mg) and saturated aqueous ammonium chloride solution (1 ml) at 0° C., and the mixture was stirred at room temperature for 30 min, and then stirred at 75° C. for 30 min. The insoluble substance was removed by filtration, and to the filtrate were added water and ethyl acetate. The organic layer was washed with water, dried over anhydrous sodium sulfate, and concentrated under reduced pressure to give the title compound (21.25 mg).

MS: [M+H]$^+$ 147.9.

C) 2-(3-{[1-(difluoromethyl)-5-methyl-1H-pyrazol-4-yl]amino}-1-methyl-1H-indazol-6-yl)propan-2-ol A mixture of 2-(3-iodo-1-methyl-1H-indazol-6-yl)propan-2-ol (45 mg), 1-(difluoromethyl)-5-methyl-1H-pyrazol-4-amine (25.1 mg), NaO$^t$Bu (41 mg), BrettPhos Pd G3 (10.3 mg), BrettPhos (6.1 mg) and THF (1 ml) was stirred under microwave irradiation at 100° C. for 2 hr. The reaction mixture was purified by basic silica gel column chromatography (hexane/ethyl acetate), and purified by HPLC to give the title compound (10 mg).

$^1$H NMR (300 MHz, CD$_3$OD) δ 0.08 (6H, s), 0.90 (3H, s), 2.29 (3H, s), 5.62 (1H, dd, J=8.6, 1.3 Hz), 5.73-6.05 (2H, m), 6.10 (1H, d, J=8.6 Hz), 6.33 (1H, s)

Example 4

2-{3-[(1,4-dimethyl-1H-pyrazol-3-yl)amino]-1-methyl-1H-indazol-6-yl}propan-2-ol

A mixture of 2-(3-iodo-1-methyl-1H-indazol-6-yl)propan-2-ol (80.5 mg), 1,4-dimethyl-1H-pyrazol-3-amine (32 mg), NaO$^t$Bu (53 mg), BrettPhos Pd G3 (6.9 mg), BrettPhos (4.8 mg) and THF (2 ml) was stirred under microwave irradiation at 120° C. for 1 hr. The reaction mixture was purified by basic silica gel column chromatography (hexane/ethyl acetate and ethyl acetate/MeOH), and the fraction was concentrated under reduced pressure. The obtained residue was crystallized from ethyl acetate/hexane to give the title compound (17.6 mg).

$^1$H NMR (300 MHz, DMSO-$d_6$) δ 1.47 (6H, s), 1.84 (3H, s), 3.66 (3H, s), 3.75 (3H, s), 5.04 (1H, s), 7.02 (1H, dd, J=8.7, 1.5 Hz), 7.32 (1H, s), 7.41 (1H, s), 7.48 (1H, d, J=8.0 Hz), 7.94 (1H, s).

Example 5

2-(1-methyl-3-{[1-methyl-3-(trifluoromethyl)-1H-pyrazol-4-yl]amino}-1H-indazol-6-yl)propan-2-ol A mixture of 2-(3-iodo-1-methyl-1H-indazol-6-yl)propan-2-ol (81.5 mg), 1-methyl-3-(trifluoromethyl)-1H-pyrazol-4-amine (48 mg), NaO$^t$Bu (54.3 mg), BrettPhos Pd G3 (7.8 mg), BrettPhos (4.5 mg) and THF (2 ml) was stirred under microwave irradiation at 120° C. for 1 hr. The reaction mixture was purified by basic silica gel column chromatography (hexane/ethyl acetate), and the fraction was concentrated under reduced pressure. The obtained residue was crystallized from ethyl acetate/hexane to give the title compound (42.5 mg).

$^1$H NMR (300 MHz, DMSO-$d_6$) δ 1.48 (6H, s), 3.83 (3H, s), 3.91 (3H, s), 5.08 (1H, s), 7.07-7.14 (1H, m), 7.45 (1H, s), 7.79 (1H, d, J=8.0 Hz), 8.01 (1H, s), 8.24 (1H, s).

Example 6

2-{3-[(5-chloro-1-methyl-1H-pyrazol-4-yl)amino]-1-methyl-1H-indazol-6-yl}propan-2-ol A mixture of 2-(3-iodo-1-methyl-1H-indazol-6-yl)propan-2-ol (80.3 mg), 5-chloro-1-methyl-1H-pyrazol-4-amine dihydrochloride (60.7 mg), NaO$^t$Bu (80.3 mg), BrettPhos Pd G3 (21 mg), BrettPhos (10.8 mg) and THF (1 ml) was stirred under microwave irradiation at 100° C. for 1 hr. The reaction mixture was purified by basic silica gel column chromatography (hexane/ethyl acetate) to give the title compound (13.3 mg).

$^1$H NMR (300 MHz, DMSO-$d_6$) δ 1.48 (6H, s), 3.72-3.83 (6H, m), 5.07 (1H, s), 7.08 (1H, dd, J=8.5, 1.3 Hz), 7.42 (1H, s), 7.73 (1H, d, J=9.1 Hz), 7.86 (1H, s), 7.98 (1H, s).

Example 7

2-{3-[(3-chloro-1-methyl-1H-pyrazol-4-yl)amino]-1-methyl-1H-indazol-6-yl}propan-2-ol A mixture of 2-(3-iodo-1-methyl-1H-indazol-6-yl)propan-2-(80.3 mg), 3-chloro-1-methyl-1H-pyrazol-4-amine (38.7 mg), NaO$^t$Bu (50.2 mg), BrettPhos Pd G3 (10.3 mg), BrettPhos (6.8 mg) and THF (2 ml) was stirred under microwave irradiation at 120° C. for 1 hr. The reaction mixture was purified by basic silica gel column chromatography (hexane/ethyl acetate), and the fraction was concentrated under reduced pressure. The obtained residue was crystallized from EtOH-ethyl acetate/hexane to give the title compound (43.4 mg).

$^1$H NMR (300 MHz, DMSO-$d_6$) δ 1.48 (6H, s), 3.79-3.83 (6H, m), 5.07 (1H, s), 7.04-7.14 (1H, m), 7.44 (1H, s), 7.84 (1H, d, J=8.0 Hz), 8.04-8.11 (2H, m).

Example 8

2-{3-[(1,5-dimethyl-1H-pyrazol-4-yl)amino]-1-methyl-1H-indazol-6-yl}propan-2-ol

A mixture of 2-(3-iodo-1-methyl-1H-indazol-6-yl)propan-2-ol (81 mg), 1,5-dimethyl-1H-pyrazol-4-amine (33.7 mg), NaO$^t$Bu (52.3 mg), BrettPhos Pd G3 (10.4 mg), BrettPhos (6.6 mg) and THF (2 ml) was stirred under microwave irradiation at 120° C. for 1 hr. The reaction mixture was purified by basic silica gel column chromatography (hexane/ethyl acetate), and the fraction was concentrated under reduced pressure. To the obtained residue were added ethyl acetate and water, and the organic layer was washed with water and saturated brine, dried over anhydrous sodium sulfate, and concentrated under reduced pressure. The obtained residue was crystallized from EtOH-ethyl acetate/hexane to give the title compound (48.6 mg).

$^1$H NMR (300 MHz, DMSO-$d_6$) δ 1.47 (6H, s), 2.20 (3H, s), 3.71 (3H, s), 3.74 (3H, s), 5.04 (1H, s), 7.04 (1H, dd, J=8.5, 1.3 Hz), 7.39 (1H, s), 7.54-7.60 (2H, m), 7.64 (1H, d, J=8.3 Hz).

Example 9

2-(1-methyl-3-{[1-methyl-5-(trifluoromethyl)-1H-pyrazol-4-yl]amino}-1H-indazol-6-yl)propan-2-ol A mixture of 2-(3-iodo-1-methyl-1H-indazol-6-yl)propan-2-(80.3 mg), 1-methyl-5-(trifluoromethyl)-1H-pyrazol-4-amine hydrochloride (55.6 mg), NaO$^t$Bu (75.2 mg), BrettPhos Pd G3 (10.3 mg), BrettPhos (6.8 mg) and THF (2 ml) was stirred under microwave irradiation at 100° C. for 2 hr. The reaction mixture was purified by basic silica gel column chromatography (hexane/ethyl acetate), and purified by HPLC to give the title compound (13 mg).

$^1$H NMR (300 MHz, DMSO-$d_6$) δ 1.48 (6H, s), 3.81 (3H, s), 3.90-3.96 (3H, m), 5.08 (1H, s), 7.08-7.15 (1H, m), 7.46 (1H, s), 7.70 (1H, d, J=8.0 Hz), 7.93 (1H, s), 8.01 (1H, s).

Example 10

2-{3-[(3-methoxy-1-methyl-1H-pyrazol-4-yl)amino]-1-methyl-1H-indazol-6-yl}propan-2-ol A mixture of 2-(3-iodo-1-methyl-1H-indazol-6-yl)propan-2-ol (80.3 mg), 3-methoxy-1-methyl-1H-pyrazol-4-amine hydrochloride (47.6 mg), NaO$^t$Bu (75.2 mg), BrettPhos Pd G3 (10.3 mg), BrettPhos (6.8 mg) and THF (2 ml) was stirred under microwave irradiation at 100° C. for 1 hr. The reaction mixture was purified by basic silica gel column chromatography (hexane/ethyl acetate) to give the title compound (45.8 mg).

$^1$H NMR (300 MHz, DMSO-$d_6$) δ 1.47 (6H, s), 3.67 (3H, s), 3.78 (3H, s), 3.84 (3H, s), 5.04 (1H, s), 6.99-7.07 (1H, m), 7.39 (1H, s), 7.78-7.90 (3H, m).

Example 11

2-{3-[(1,3-dimethyl-1H-pyrazol-5-yl)amino]-1-methyl-1H-indazol-6-yl}propan-2-ol

A mixture of 2-(3-iodo-1-methyl-1H-indazol-6-yl)propan-2-ol (80.3 mg), 1,3-dimethyl-1H-pyrazol-5-amine (32.6 mg), NaO$^t$Bu (53.2 mg), BrettPhos Pd G3 (11.3 mg), BrettPhos (7.2 mg) and THF (2 ml) was stirred under microwave irradiation at 100° C. for 1 hr. The reaction mixture was purified by basic silica gel column chromatography (ethyl acetate/MeOH), and purified by HPLC to give the title compound (29.8 mg).

$^1$H NMR (300 MHz, DMSO-$d_6$) δ 1.48 (6H, s), 2.08 (3H, s), 3.64 (3H, s), 3.83 (3H, s), 5.09 (1H, s), 5.99 (1H, s), 7.13 (1H, dd, J=8.5, 1.3 Hz), 7.48 (1H, s), 7.65 (1H, d, J=9.1 Hz), 8.47 (1H, s).

Example 12

2-{3-[2-methoxy-4-(1-methyl-1H-pyrazol-4-yl)anilino]-1H-indazol-6-yl}propan-2-ol

A) methyl 3-iodo-1-(oxan-2-yl)-1H-indazole-6-carboxylate

To a mixture of methyl 3-iodo-1H-indazole-6-carboxylate (30 g), 3,4-dihydro-2H-pyran (13.6 ml) and THF (150 ml) was added p-toluenesulfonic acid monohydrate (1.89 g) at room temperature, and the mixture was stirred overnight under nitrogen atmosphere at 50° C. To the reaction mixture was added silica gel (135 g), and the mixture was concentrated under reduced pressure. The obtained residue was purified by silica gel column chromatography (ethyl acetate), and the fraction was concentrated under reduced pressure. The obtained residue was crystallized from ethyl acetate/hexane to give the title compound (27.7 g).

MS: [M+H]$^+$ 387.2.

B) 2-methoxy-4-(1-methyl-1H-pyrazol-4-yl)aniline

To a mixture of 4-bromo-2-methoxyaniline (2 g), 1-methyl-4-(4,4,5,5-tetramethyl-1,3,2-dioxaborolan-2-yl)-1H-pyrazole (2.47 g), cesium carbonate (5.48 g), DME (40 ml) and water (12 ml) was added XPhos Pd G3 (0.251 g), and the mixture was stirred under nitrogen atmosphere at 100° C. for 2 hr. To the reaction mixture was added water, and the mixture was extracted with ethyl acetate. The organic layer was washed with water and saturated brine, dried over anhydrous sodium sulfate, and concentrated under reduced pressure. The residue was washed with a mixture of ethyl acetate and hexane to give the title compound (1.91 g).

MS: [M+H]$^+$ 204.0.

C) methyl 3-[2-methoxy-4-(1-methyl-1H-pyrazol-4-yl)anilino]-1-(oxan-2-yl)-1H-indazole-6-carboxylate A mixture of methyl 3-iodo-1-(oxan-2-yl)-1H-indazole-6-carboxylate (150 mg), 2-methoxy-4-(1-methyl-1H-pyrazol-4-yl)aniline (87 mg), cesium carbonate (253 mg), Pd(OAc)$_2$ (8.7 mg), XANTPHOS (44.9 mg) and toluene (2 ml) was stirred overnight under nitrogen atmosphere at 80° C. The insoluble substance was removed by filtration through Celite, and the filtrate was concentrated under reduced pressure. The residue was purified by silica gel column chromatography (ethyl acetate/MeOH) to give the title compound (120 mg).

MS: [M+H]$^+$ 462.1.

D) methyl 3-[2-methoxy-4-(1-methyl-1H-pyrazol-4-yl)anilino]-1H-indazole-6-carboxylate To a mixture of methyl 3-[2-methoxy-4-(1-methyl-1H-pyrazol-4-yl)anilino]-1-(oxan-2-yl)-1H-indazole-6-carboxylate (133 mg), EtOH (0.45 ml) and THF (1.35 ml) was added 6 mol/l hydrochloric acid (0.24 ml) at room temperature, and the mixture was stirred at 50° C. for 30 min. To the reaction mixture was added a mixture of saturated aqueous sodium hydrogencarbonate solution, ethyl acetate and THF, and the organic layer was washed with water and saturated brine, dried over anhydrous sodium sulfate, and concentrated under reduced pressure. The obtained residue was purified by HPLC to give the title compound (107 mg).

MS: [M+H]$^+$ 378.0.

E) 2-{3-[2-methoxy-4-(1-methyl-1H-pyrazol-4-yl)anilino]-1H-indazol-6-yl}propan-2-ol To a mixture of methylmagnesium bromide (1 mol/l THF solution) (1.7 ml) and THF (2.0 ml) was added methyl 3-[2-methoxy-4-(1-methyl-1H-pyrazol-4-yl)anilino]-1H-indazole-6-carboxylate (107 mg) at 0° C., and the mixture was stirred under nitrogen atmosphere at 40° C. for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by basic silica gel column chromatography (ethyl acetate/MeOH) to give the title compound (67 mg).

$^1$H NMR (400 MHz, DMSO-d$_6$) δ 1.48 (6H, s), 3.85 (3H, s), 3.96 (3H, s), 5.07 (1H, s), 7.05-7.14 (2H, m), 7.17 (1H, d, J=1.7 Hz), 7.46 (1H, s), 7.51 (1H, s), 7.76 (1H, d, J=8.6 Hz), 7.79 (1H, s), 8.01 (1H, d, J=8.3 Hz), 8.04 (1H, s), 11.95 (1H, s).

Example 13

2-(3-{[5-chloro-1-(difluoromethyl)-1H-pyrazol-4-yl]amino}-1-methyl-1H-indazol-6-yl)propan-2-ol

A) 1-(difluoromethyl)-4-nitro-1H-pyrazole

A mixture of 4-nitro-1H-pyrazole (5 g), cesium carbonate (14.5 g) and DMF (40 ml) was stirred at 120° C. for 5 min. Sodium 2-chloro-2,2-difluoroacetate (13.5 g) was added thereto at 120° C., and the mixture was stirred for 10 min. To the reaction mixture was added water, and the mixture was extracted with Et$_2$O. The organic layer was washed with water and saturated brine, dried over anhydrous sodium sulfate, and concentrated under reduced pressure. The residue was purified by silica gel column chromatography (hexane/ethyl acetate) to give the title compound (6.48 g).

$^1$H NMR (300 MHz, DMSO-d$_6$) δ 7.64-8.11 (1H, m), 8.59 (1H, s), 9.43 (1H, s).

B) 5-chloro-1-(difluoromethyl)-4-nitro-1H-pyrazole

To a mixture of 1-(difluoromethyl)-4-nitro-1H-pyrazole (5.96 g) and THF (150 ml) was added a solution of lithium (bistrimethylsilyl)amide in THF (1.3 mol/l, 57 ml) while keeping the internal temperature within −75° C. to −70° C., and the mixture was stirred for 30 min. To the reaction mixture was added a mixture of hexachloroethane (10.3 g) and THF (50 ml) while keeping the internal temperature within −75° C. to −70° C., and the mixture was stirred under nitrogen atmosphere at −78° C. for 30 min, and then stirred at room temperature for 2 hr. To the reaction mixture was added saturated aqueous ammonium chloride solution at 0° C., and the mixture was extracted with a mixture of ethyl acetate and Et$_2$O. The organic layer was washed with water and saturated brine, dried over anhydrous sodium sulfate, and concentrated under reduced pressure. The residue was purified by silica gel column chromatography (hexane/ethyl acetate) to give the title compound (1.23 g).

$^1$H NMR (300 MHz, DMSO-d$_6$) δ 7.84-8.32 (1H, m), 8.74 (1H, s).

C) 5-chloro-1-(difluoromethyl)-1H-pyrazol-4-amine

To a mixture of 5-chloro-1-(difluoromethyl)-4-nitro-1H-pyrazole (1.23 g), ammonium chloride (1.7 g), MeOH (15 ml) and THF (15 ml) was added zinc powder (2.0 g) at 50° C., and the mixture was stirred at 50° C. for 30 min. The insoluble substance was removed by filtration, and the filtrate was concentrated under reduced pressure. The obtained residue was purified by silica gel column chromatography (hexane/ethyl acetate) to give the title compound (0.52 g).

MS: [M+H]$^+$ 167.9.

D) 2-(3-{[5-chloro-1-(difluoromethyl)-1H-pyrazol-4-yl]amino}-1-methyl-1H-indazol-6-yl)propan-2-ol A mixture of 2-(3-iodo-1-methyl-1H-indazol-6-yl)propan-2-ol (80.3 mg), 5-chloro-1-(difluoromethyl)-1H-pyrazol-4-amine (53.2 mg), NaO$^t$Bu (40.2 mg), BrettPhos Pd G3 (19.8 mg), BrettPhos (12.8 mg) and THF (2 ml) was stirred under microwave irradiation at 100° C. for 1 hr. The reaction mixture was purified by basic silica gel column chromatography (hexane/ethyl acetate), and the fraction was concentrated under reduced pressure. The obtained residue was crystallized from ethyl acetate/hexane to give the title compound (9.8 mg).

$^1$H NMR (300 MHz, DMSO-d$_6$) δ 1.49 (6H, s), 3.83 (3H, s), 5.09 (1H, s), 7.13 (1H, dd, J=8.7, 1.5 Hz), 7.47 (1H, s), 7.64-8.06 (2H, m), 8.34 (1H, s), 8.43 (1H, s).

Example 14

2-{3-[(1,5-dimethyl-1H-pyrazol-3-yl)amino]-1-methyl-1H-indazol-6-yl}propan-2-ol

A mixture of 2-(3-iodo-1-methyl-1H-indazol-6-yl)propan-2-ol (80.1 mg), 1,5-dimethyl-1H-pyrazol-3-amine (33 mg), NaO$^t$Bu (37 mg), BrettPhos Pd G3 (20.3 mg), BrettPhos (12.4 mg) and THF (1 ml) was stirred under microwave irradiation at 100° C. for 1 hr. The reaction mixture was purified by basic silica gel column chromatography (hexane/ethyl acetate), and the fraction was concentrated under reduced pressure. The obtained residue was crystallized from EtOH-ethyl acetate/heptane to give the title compound (46.8 mg).

$^1$H NMR (400 MHz, DMSO-d$_6$) δ 1.47 (6H, s), 2.23 (3H, s), 3.60 (3H, s), 3.81 (3H, s), 5.04 (1H, s), 6.34 (1H, s), 7.05 (1H, dd, J=8.5, 1.3 Hz), 7.42 (1H, s), 7.85 (1H, d, J=8.6 Hz), 8.98 (1H, s).

Example 15

2-{3-[(5-methoxy-1-methyl-1H-pyrazol-4-yl)amino]-1-methyl-1H-indazol-6-yl}propan-2-ol A mixture of 2-(3-iodo-1-methyl-1H-indazol-6-yl)propan-2-ol (81.1 mg), 5-methoxy-1-methyl-1H-pyrazol-4-amine (37 mg), NaO$^t$Bu (38.1 mg), BrettPhos Pd G3 (19.8 mg), BrettPhos (12.4 mg) and THF (1 ml) was stirred under microwave irradiation at 100° C. for 1 hr. The reaction mixture was purified by basic silica gel column chromatography (hexane/ethyl acetate and ethyl acetate/MeOH), and the fraction was concentrated under reduced pressure. The obtained residue was crystallized from MeOH/water to give the title compound (22.4 mg).

$^1$H NMR (400 MHz, DMSO-d$_6$) δ 1.47 (6H, s), 3.59 (3H, s), 3.73 (3H, s), 3.91 (3H, s), 5.03 (1H, br s), 7.02 (1H, dd, J=8.5, 1.3 Hz), 7.36 (1H, s), 7.39 (1H, s), 7.48 (1H, s), 7.56 (1H, d, J=8.6 Hz).

Example 16

2-{3-[(1,3-dimethyl-1H-pyrazol-4-yl)amino]-1-methyl-1H-indazol-6-yl}propan-2-ol

A mixture of 2-(3-iodo-1-methyl-1H-indazol-6-yl)propan-2-ol (80.1 mg), 1,3-dimethyl-1H-pyrazol-4-amine (33 mg), NaO$^t$Bu (37 mg), BrettPhos Pd G3 (20.3 mg), BrettPhos (12.4 mg) and THF (1 ml) was stirred under microwave irradiation at 100° C. for 1 hr. The reaction mixture was purified by basic silica gel column chromatography (hexane/ethyl acetate), and the fraction was concentrated under reduced pressure. The obtained residue was crystallized from EtOH-ethyl acetate/heptane to give the title compound (49.7 mg).

$^1$H NMR (300 MHz, DMSO-d$_6$) δ 1.48 (6H, s), 2.18 (3H, s), 3.73 (3H, s), 3.79 (3H, s), 5.05 (1H, s), 7.04-7.11 (1H, m), 7.41 (1H, s), 7.75-7.83 (2H, m), 7.89 (1H, s).

Example 17

2-{3-[(4-chloro-1-methyl-1H-pyrazol-3-yl)amino]-1-methyl-1H-indazol-6-yl}propan-2-ol A mixture of 2-(3-iodo-1-methyl-1H-indazol-6-yl)propan-2-ol (82.3 mg), 4-chloro-1-methyl-1H-pyrazol-3-amine (37.8 mg), NaO$^t$Bu (38.1 mg), BrettPhos Pd G3 (18.8 mg), BrettPhos (12 mg) and THF (1 ml) was stirred under microwave irradiation at 100° C. for 1 hr. The reaction mixture was purified by basic silica gel column chromatography (hexane/ethyl acetate and ethyl acetate/MeOH), and the fraction was concentrated under reduced pressure. The obtained residue was crystallized from ethyl acetate/heptane to give the title compound (39.6 mg).

$^1$H NMR (300 MHz, DMSO-d$_6$) δ 1.47 (6H, s), 3.71 (3H, s), 3.78 (3H, s), 5.06 (1H, s), 7.05 (1H, dd, J=8.5, 1.3 Hz), 7.41-7.48 (2H, m), 7.81 (1H, s), 8.11 (1H, s).

Example 18

2-{3-[(4-chloro-1,5-dimethyl-1H-pyrazol-3-yl)amino]-1-methyl-1H-indazol-6-yl}propan-2-ol A mixture of 2-(3-iodo-1-methyl-1H-indazol-6-yl)propan-2-ol (82.3 mg), 4-chloro-1,5-dimethyl-1H-pyrazol-3-amine (42.4 mg), NaO$^t$Bu (38.1 mg), BrettPhos Pd G3 (18.8 mg), BrettPhos (12 mg) and THF (1 ml) was stirred under microwave irradiation at 100° C. for 1 hr. The reaction mixture was purified by basic silica gel column chromatography (hexane/ethyl acetate and ethyl acetate/MeOH), and the fraction was concentrated under reduced pressure. The obtained residue was crystallized from ethyl acetate/heptane to give the title compound (45 mg).

$^1$H NMR (300 MHz, DMSO-d$_6$) δ 1.47 (6H, s), 2.22 (3H, s), 3.64 (3H, s), 3.78 (3H, s), 5.06 (1H, s), 7.05 (1H, dd, J=8.5, 1.3 Hz), 7.42-7.50 (2H, m), 8.05 (1H, s).

Example 19

2-{1-methyl-3-[(4,5,6,7-tetrahydropyrazolo[1,5-a]pyridin-3-yl)amino]-1H-indazol-6-yl}propan-2-ol A mixture of 2-(3-iodo-1-methyl-1H-indazol-6-yl)propan-2-ol (60.9 mg), 4,5,6,7-tetrahydropyrazolo[1,5-a]pyridin-3-amine hydrochloride (36 mg), NaO$^t$Bu (46.1 mg), BrettPhos Pd G3 (19.8 mg), BrettPhos (10.1 mg) and THF (1 ml) was stirred under microwave irradiation at 100° C. for 1 hr. The reaction mixture was purified by basic silica gel column chromatography (hexane/ethyl acetate and ethyl acetate/MeOH), and the fraction was concentrated under reduced pressure. The obtained residue was crystallized from EtOH/ethyl acetate/heptane to give the title compound (35.3 mg).

$^1$H NMR (300 MHz, DMSO-d$_6$) δ 1.47 (6H, s), 1.72-1.84 (2H, m), 1.89-2.00 (2H, m), 2.69 (2H, t, J=6.2 Hz), 3.75 (3H, s), 4.02 (2H, t, J=6.1 Hz), 5.05 (1H, s), 7.05 (1H, dd, J=8.5, 1.3 Hz), 7.39 (1H, s), 7.60-7.69 (3H, m).

Example 20

2-{3-[(6,7-dihydro-5H-pyrazolo[5,1-b][1,3]oxazin-3-yl)amino]-1-methyl-1H-indazol-6-yl}propan-2-ol A mixture of 2-(3-iodo-1-methyl-1H-indazol-6-yl)propan-2-ol (60.9 mg), 6,7-dihydro-5H-pyrazolo[5,1-b][1,3]oxazin-3-amine hydrochloride (37 mg), NaO$^t$Bu (46.1 mg), BrettPhos Pd G3 (17.8 mg), BrettPhos (10.1 mg) and THF (1 ml) was stirred under microwave irradiation at 100° C. for 1 hr. The reaction mixture was purified by basic silica gel column chromatography (ethyl acetate/MeOH), and the fraction was concentrated under reduced pressure. The obtained residue was crystallized from ethyl acetate/heptane to give the title compound (18.1 mg).

$^1$H NMR (300 MHz, DMSO-d$_6$) δ 1.46 (6H, s), 2.10-2.24 (2H, m), 3.72 (3H, s), 4.09 (2H, t, J=6.1 Hz), 4.22-4.30 (2H, m), 5.03 (1H, s), 7.00 (1H, dd, J=8.5, 1.3 Hz), 7.34-7.40 (2H, m), 7.46 (1H, s), 7.57 (1H, d, J=8.7 Hz).

Example 21

2-{3-[(1-ethyl-5-methyl-1H-pyrazol-3-yl)amino]-1-methyl-1H-indazol-6-yl}propan-2-ol A mixture of 2-(3-iodo-1-methyl-1H-indazol-6-yl)propan-2-ol (100 mg), 1-ethyl-5-methyl-1H-pyrazol-3-amine (47.5 mg), NaO$^t$Bu (91 mg), BrettPhos Pd G3 (22.9 mg), BrettPhos (13.6 mg) and THF (2 ml) was stirred under microwave irradiation at 100° C. for 1 hr. The reaction mixture was purified by basic silica gel column chromatography (hexane/ethyl acetate) to give the title compound (73 mg).

$^1$H NMR (400 MHz, DMSO-d$_6$) δ 1.29 (3H, t, J=7.2 Hz), 1.48 (6H, s), 2.24 (3H, s), 3.81 (3H, s), 3.92 (2H, q, J=7.2 Hz), 5.04 (1H, s), 6.34 (1H, s), 7.05 (1H, dd, J=8.6, 1.3 Hz), 7.42 (1H, s), 7.86 (1H, d, J=8.4 Hz), 9.02 (1H, s).

Example 22

2-(1-methyl-3-{[5-methyl-1-(2-methylpropyl)-1H-pyrazol-3-yl]amino}-1H-indazol-6-yl)propan-2-ol A mixture of 2-(3-iodo-1-methyl-1H-indazol-6-yl)propan-2-ol (60.9 mg), 5-methyl-1-(2-methylpropyl)-1H-pyrazol-3-amine (33 mg), NaO$^t$Bu (28.1 mg), BrettPhos Pd G3 (17.8 mg), BrettPhos (10.1 mg) and THF (1 ml) was stirred under microwave irradiation at 100° C. for 1 hr. The reaction mixture was purified by basic silica gel column chromatography (hexane/ethyl acetate), and the fraction was concentrated under reduced pressure. The obtained residue was crystallized from ethyl acetate/heptane to give the title compound (31.4 mg).

$^1$H NMR (300 MHz, DMSO-d$_6$) δ 0.87 (6H, d, J=6.8 Hz), 1.47 (6H, s), 2.04-2.19 (1H, m), 2.23 (3H, s), 3.68 (2H, d, J=7.2 Hz), 3.81 (3H, s), 5.05 (1H, s), 6.36 (1H, d, J=0.8 Hz), 7.04 (1H, dd, J=8.5, 1.3 Hz), 7.42 (1H, s), 7.87 (1H, d, J=8.7 Hz), 9.06 (1H, s).

Example 23

2-{3-[(5-ethyl-1-methyl-1H-pyrazol-3-yl)amino]-1-methyl-1H-indazol-6-yl}propan-2-ol A mixture of 2-(3-iodo-1-methyl-1H-indazol-6-yl)propan-2-ol (60.9 mg), 5-ethyl-1-methyl-1H-pyrazol-3-amine (27 mg), NaO$^t$Bu (26.1 mg), BrettPhos Pd G3 (17.8 mg), BrettPhos (10.1 mg) and THF (1 ml) was stirred under microwave irradiation at 100° C. for 1 hr. The reaction mixture was purified by basic silica gel column chromatography (hexane/ethyl acetate), and the fraction was concentrated under reduced pressure. The obtained residue was crystallized from EtOH/ethyl acetate/heptane to give the title compound (29.6 mg).

$^1$H NMR (300 MHz, DMSO-d$_6$) δ 1.20 (3H, t, J=7.6 Hz), 1.47 (6H, s), 2.53-2.66 (2H, m), 3.61 (3H, s), 3.81 (3H, s), 5.05 (1H, s), 6.35 (1H, s), 6.99-7.11 (1H, m), 7.42 (1H, s), 7.86 (1H, d, J=8.3 Hz), 9.00 (1H, s).

Example 24

2-(1-methyl-3-{[5-methyl-1-(2,2,2-trifluoroethyl)-1H-pyrazol-3-yl]amino}-1H-indazol-6-yl)propan-2-ol A mixture of 2-(3-iodo-1-methyl-1H-indazol-6-yl)propan-2-ol (60.9 mg), 5-methyl-1-(2,2,2-trifluoroethyl)-1H-pyrazol-3-amine (37 mg), NaO$^t$Bu (28.1 mg), BrettPhos Pd G3 (17.8 mg), BrettPhos (10.1 mg) and THF (1 ml) was stirred under microwave irradiation at 100° C. for 3 hr. The reaction mixture was purified by basic silica gel column chromatography (hexane/ethyl acetate), and the fraction was concentrated under reduced pressure. The obtained residue was crystallized from EtOH/ethyl acetate/heptane, and the obtained solid was purified by HPLC to give the title compound (8.3 mg).

$^1$H NMR (300 MHz, CD$_3$OD) δ 1.60 (6H, s), 2.32 (3H, s), 3.89 (3H, s), 4.72 (2H, q, J=9.0 Hz), 6.28 (1H, s), 7.15 (1H, dd, J=8.5, 1.3 Hz), 7.44-7.49 (1H, m), 7.69 (1H, dd, J=8.7, 0.8 Hz), (NH and OH peaks were not observed).

Example 25

2-{3-[(6,6-dimethyl-6,7-dihydro-5H-pyrazolo[5,1-b][1,3]oxazin-3-yl)amino]-1-methyl-1H-indazol-6-yl}propan-2-ol A mixture of 2-(3-iodo-1-methyl-1H-indazol-6-yl)propan-2-ol (60.9 mg), 6,6-dimethyl-6,7-dihydro-5H-pyrazolo[5,1-b][1,3]oxazin-3-amine hydrochloride (42 mg), NaO$^t$Bu (46.1 mg), BrettPhos Pd G3 (17.8 mg), BrettPhos (10.1 mg) and THF (1 ml) was stirred under microwave irradiation at 100° C. for 1 hr. The reaction mixture was purified by basic silica gel column chromatography (ethyl acetate/MeOH), and the fraction was concentrated under reduced pressure. The obtained residue was crystallized from ethyl acetate/heptane, and the obtained solid was purified by HPLC to give the title compound (19.1 mg).

$^1$H NMR (300 MHz, DMSO-d$_6$) δ 1.06 (6H, s), 1.46 (6H, s), 3.72 (3H, s), 3.83 (2H, s), 3.94 (2H, s), 5.03 (1H, s), 6.99 (1H, dd, J=8.5, 1.3 Hz), 7.37 (1H, s), 7.44 (1H, s), 7.50 (1H, s), 7.55 (1H, d, J=8.3 Hz).

Example 26

2-{3-[2-fluoro-4-(1-methyl-1H-pyrazol-4-yl)anilino]-1H-indazol-6-yl}propan-2-ol

A) 2-fluoro-4-(1-methyl-1H-pyrazol-4-yl)aniline

To a mixture of 4-bromo-2-fluoroaniline (8.02 g), 1-methyl-4-(4,4,5,5-tetramethyl-1,3,2-dioxaborolan-2-yl)-1H-pyrazole (9.55 g), cesium carbonate (20.7 g), DME (120 ml) and water (40 ml) was added XPhos Pd G3 (0.37 g), and the mixture was stirred under nitrogen atmosphere at 100° C. for 2 hr. To the reaction mixture was added water, and the mixture was extracted with ethyl acetate. The organic layer was washed with water and saturated brine, dried over anhydrous sodium sulfate, and filtered through Celite, and the filtrate was concentrated under reduced pressure. The residue was crystallized from ethyl acetate/hexane to give the title compound (6.47 g).

MS: $[M+H]^+$ 191.9.

B) methyl 3-[2-fluoro-4-(1-methyl-1H-pyrazol-4-yl)anilino]-1-(oxan-2-yl)-1H-indazole-6-carboxylate A mixture of methyl 3-iodo-1-(oxan-2-yl)-1H-indazole-6-carboxylate (250 mg), 2-fluoro-4-(1-methyl-1H-pyrazol-4-yl)aniline (124 mg), cesium carbonate (422 mg), Pd(OAc)$_2$ (14.5 mg), XANTPHOS (74.9 mg) and toluene (5 ml) was stirred overnight under nitrogen atmosphere at 80° C. The insoluble substance was removed by filtration through Celite, and the filtrate was concentrated under reduced pressure. The residue was purified by silica gel column chromatography (ethyl acetate/hexane) to give the title compound (165 mg).

MS: $[M+H]^+$ 450.1.

C) 2-{3-[2-fluoro-4-(1-methyl-1H-pyrazol-4-yl)anilino]-1-(oxan-2-yl)-1H-indazol-6-yl}propan-2-ol To methylmagnesium bromide (1 mol/l THF solution) (2.2 ml) was added a mixture of methyl 3-[2-fluoro-4-(1-methyl-1H-pyrazol-4-yl)anilino]-1-(oxan-2-yl)-1H-indazole-6-carboxylate (165 mg) and THF (3.5 ml) at 0° C., and the mixture was stirred under nitrogen atmosphere at 40° C. for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by basic silica gel column chromatography (hexane/ethyl acetate) to give the title compound (81 mg).

MS: $[M+H]^+$ 450.1.

D) 2-{3-[2-fluoro-4-(1-methyl-1H-pyrazol-4-yl)anilino]-1H-indazol-6-yl}propan-2-ol To a mixture of 2-{3-[2-fluoro-4-(1-methyl-1H-pyrazol-4-yl)anilino]-1-(oxan-2-yl)-1H-indazol-6-yl}propan-2-ol (81 mg), EtOH (0.27 ml) and THF (0.8 ml) was added 6 mol/l hydrochloric acid (0.15 ml) at room temperature, and the mixture was stirred for 1 hr. To the reaction mixture was added a mixture of saturated aqueous sodium hydrogencarbonate solution, ethyl acetate and THF, and the organic layer was washed with water and saturated brine, dried over anhydrous sodium sulfate, and concentrated under reduced pressure. The obtained residue was purified by HPLC, and the fraction was concentrated under reduced pressure. The obtained residue was crystallized from ethyl acetate/hexane to give the title compound (23 mg).

$^1$H NMR (400 MHz, DMSO-d$_6$) δ 1.48 (6H, s), 3.85 (3H, s), 5.06 (1H, s), 7.11 (1H, dd, J=8.6, 1.3 Hz), 7.28 (1H, dd, J=8.5, 1.7 Hz), 7.41 (1H, dd, J=13.1, 1.9 Hz), 7.45-7.48 (1H, m), 7.80 (1H, s), 7.85 (1H, d, J=8.6 Hz), 7.99-8.07 (2H, m), 8.30 (1H, d, J=1.5 Hz), 12.01 (1H, s).

Example 27

2-{4-fluoro-3-[(5-methoxy-1-methyl-1H-pyrazol-4-yl)amino]-1-methyl-1H-indazol-6-yl}propan-2-ol

A) 5-chloro-1-methyl-4-nitro-1H-pyrazole

To a mixture of 1-methyl-4-nitro-1H-pyrazole (6.02 g) and THF (60 ml) was added a solution of lithium (bistrimethylsilyl)amide in THF (1.3 mol/l, 40 ml) while keeping the internal temperature within −75° C. to −70° C., and the mixture was stirred for 30 min. To the reaction mixture was added hexachloroethane (13.5 g) at −78° C., and the mixture was stirred under nitrogen atmosphere at −78° C. for 1 hr, and then stirred overnight at room temperature. To the reaction mixture was added saturated aqueous ammonium chloride solution at 0° C., and the mixture was extracted with a mixture of ethyl acetate and hexane. The organic layer was washed with water and saturated brine, dried over anhydrous sodium sulfate, and concentrated under reduced pressure. The residue was purified by silica gel column chromatography (hexane/ethyl acetate) to give the title compound (6.23 g).

$^1$H NMR (300 MHz, DMSO-d$_6$) δ 3.89 (3H, s), 8.43 (1H, s).

B) 5-methoxy-1-methyl-4-nitro-1H-pyrazole

To a mixture of 60% sodium hydride (361 mg) and DMF (25 ml) was added MeOH (0.31 ml) at 0° C., and the mixture was stirred for 5 min. To the reaction mixture was added 5-chloro-1-methyl-4-nitro-1H-pyrazole (1010 mg) at 0° C., and the mixture was stirred under nitrogen atmosphere for 1 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (890 mg).

MS: $[M+H]^+$ 157.9.

C) 5-methoxy-1-methyl-1H-pyrazol-4-amine

A mixture of 5-methoxy-1-methyl-4-nitro-1H-pyrazole (330 mg), 10% palladium on carbon (36 mg) and MeOH (7 ml) was stirred under hydrogen atmosphere at room temperature for 3 hr. The insoluble substance was removed by filtration, to the filtrate was added aqueous potassium carbonate solution, and the mixture was extracted with ethyl acetate. The organic layer was dried over anhydrous sodium sulfate, and concentrated under reduced pressure to give the title compound (99 mg).

MS: $[M+H]^+$ 127.9.

D) 2-{4-fluoro-3-[(5-methoxy-1-methyl-1H-pyrazol-4-yl)amino]-1-methyl-1H-indazol-6-yl}propan-2-ol A mixture of 2-(4-fluoro-3-iodo-1-methyl-1H-indazol-6-yl)propan-2-ol (100 mg), 5-methoxy-1-methyl-1H-pyrazol- 4-amine (49.4 mg), NaO$^t$Bu (43.2 mg), BrettPhos Pd G3 (20.5 mg), BrettPhos (12.3 mg) and THF (1.5 ml) was stirred under microwave irradiation at 100° C. for 1 hr. The reaction mixture was purified by basic silica gel column chromatography (hexane/ethyl acetate), and the fraction was concentrated under reduced pressure. The obtained residue was crystallized from EtOH/ethyl acetate/heptane to give the title compound (24.8 mg).

$^1$H NMR (300 MHz, DMSO-d$_6$) δ 1.46 (6H, s), 3.57 (3H, s), 3.73 (3H, s), 3.92 (3H, s), 5.16 (1H, s), 6.78 (1H, dd, J=12.7, 0.9 Hz), 7.00 (1H, s), 7.20 (1H, s), 7.24 (1H, s).

Example 28

2-{7-fluoro-3-[(5-methoxy-1-methyl-1H-pyrazol-4-yl)amino]-1-methyl-1H-indazol-6-yl}propan-2-ol A) 6-bromo-7-fluoro-1H-indazole A mixture of 4-bromo-2,3-difluorobenzaldehyde (4 g), O-methylhydroxylamine hydrochloride (1.97 g), potassium carbonate (3.00 g) and DME (48 ml) was stirred at 40° C. for 3 hr. The reaction mixture was filtered, and the filtrate was concentrated under reduced pressure. To the obtained residue were added DME (40 ml) and hydrazine monohydrate (12 ml), and the mixture was stirred at 90° C. for 22 hr. The reaction mixture was cooled to room temperature, and water (30 ml) was added thereto. The resulting solid was collected by filtration, washed with water, and dried under reduced pressure to give the title compound (3.18 g).
MS: [M+H]$^+$ 216.8.

B) methyl 7-fluoro-1H-indazole-6-carboxylate

A mixture of 6-bromo-7-fluoro-1H-indazole (3.18 g), PdCl$_2$(dppf) (0.54 g), triethylamine (6.17 ml) and MeOH (50 ml) was stirred under carbon monoxide pressure (50 psi) at 90° C. for 4 hr. To the reaction mixture was added water (450 ml), and the resulting solid was collected by filtration, washed with water, and dried under reduced pressure to give the title compound (2.62 g).
MS: [M+H]$^+$ 194.9.

C) 2-(7-fluoro-1H-indazol-6-yl)propan-2-ol

To methylmagnesium bromide (1 mol/l THE solution) (44.8 ml) was added a mixture of methyl 7-fluoro-1H-indazole-6-carboxylate (1.45 g) and THF (60 ml) at 0° C., and the mixture was stirred under nitrogen atmosphere at 40° C. for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure to give the title compound (1.61 g).
MS: [M+H]$^+$ 194.9.

D) 2-(7-fluoro-3-iodo-1H-indazol-6-yl)propan-2-ol

To a mixture of 2-(7-fluoro-1H-indazol-6-yl)propan-2-ol (1.45 g), potassium carbonate (2.06 g) and DMF (23 ml) was added iodine (3.79 g) at 0° C., and the mixture was stirred at room temperature until the starting material disappeared. To the reaction mixture was added a mixture of sodium hydrogen sulfite (2.33 g) and water (8 ml). Water was added again thereto, and the mixture was extracted with ethyl acetate. The organic layer was dried over anhydrous magnesium sulfate, and concentrated under reduced pressure to give the title compound (3.54 g).
MS: [M+H]$^+$ 320.8.

E) 2-(7-fluoro-3-iodo-1-methyl-1H-indazol-6-yl)propan-2-ol

To a mixture of 2-(7-fluoro-3-iodo-1H-indazol-6-yl)propan-2-ol (2.39 g) and DMF (14 ml) was added cesium carbonate (3.41 g), and the mixture was stirred at room temperature for 30 min. To the reaction mixture was added dropwise a mixture of methyl iodide (1.4 ml) and DMF (4.8 ml), and the mixture was stirred overnight at room temperature. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (hexane/ethyl acetate) to give the title compound (1.26 g).
MS: [M+H]$^+$ 334.9.

F) 2-{7-fluoro-3-[(5-methoxy-1-methyl-1H-pyrazol-4-yl)amino]-1-methyl-1H-indazol-6-yl}propan-2-ol A mixture of 2-(7-fluoro-3-iodo-1-methyl-1H-indazol-6-yl)propan-2-ol (100 mg), 5-methoxy-1-methyl-1H-pyrazol-4-amine (45.7 mg), NaO$^t$Bu (101 mg), BrettPhos Pd G3 (27.1 mg), BrettPhos (16.1 mg) and THF (1.5 ml) was stirred under microwave irradiation at 100° C. for 1 hr. The reaction mixture was purified by basic silica gel column chromatography (ethyl acetate/MeOH), and the fraction was concentrated under reduced pressure. The obtained residue was purified by HPLC, and the fraction was concentrated under reduced pressure. The obtained residue was crystallized from EtOH-ethyl acetate/hexane to give the title compound (17 mg).

$^1$H NMR (400 MHz, DMSO-d$_6$) δ 1.54 (6H, s), 3.59 (3H, s), 3.85 (3H, s), 3.90 (3H, s), 5.27 (1H, s), 7.19 (1H, dd, J=8.6, 6.6 Hz), 7.36 (1H, s), 7.42 (1H, d, J=8.6 Hz), 7.61 (1H, s).

Example 29

2-(3-{[5-(methoxymethyl)-1-methyl-1H-pyrazol-4-yl]amino}-1-methyl-1H-indazol-6-yl)propan-2-ol A) 2-(3-iodo-1-methyl-1H-indazol-6-yl)propan-2-ol To a mixture of 2-(3-iodo-1H-indazol-6-yl)propan-2-ol (4.95 g), cesium carbonate (8.01 g) and DMF (40 ml) was added methyl iodide (1.55 ml), and the mixture was stirred at room temperature for 2 days. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (3.87 g).
MS: [M+H]$^+$ 316.9.

B) (1-methyl-1H-pyrazol-5-yl)methanol

To a mixture of 1-methyl-1H-pyrazole-5-carboxylic acid (2.04 g), 4-methylmorpholine (2.1 ml) and THF (40 ml) was added isobutyl chloroformate (2.5 ml) at 0° C., and the mixture was stirred for 30 min. The insoluble substance was removed by filtration, the filtrate was added to a mixture of sodium borohydride (1.34 g) and water (8 ml) at 0° C., and the mixture was stirred at room temperature for 1 hr. To the reaction mixture was added 6 mol/l hydrochloric acid (6 ml) at 0° C., and the mixture was stirred at room temperature for 10 min. To the reaction mixture was added anhydrous sodium sulfate, the insoluble substance was removed by filtration, and the filtrate was concentrated under reduced pressure. The residue was purified by silica gel column chromatography (hexane/ethyl acetate) to give the title compound (0.78 g).

MS: [M+H]$^+$ 112.9.

C) 5-(methoxymethyl)-1-methyl-1H-pyrazole

To a mixture of (1-methyl-1H-pyrazol-5-yl)methanol (926 mg) and DMF (25 ml) was added 60% sodium hydride (370 mg) at 0° C., and the mixture was stirred at room temperature for 3 min. To the reaction mixture was added methyl iodide (0.58 ml) at 0° C., and the mixture was stirred overnight at room temperature. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (786 mg).

MS: [M+H]$^+$ 126.9.

D) 5-(methoxymethyl)-1-methyl-4-nitro-1H-pyrazole

To a mixture of 5-(methoxymethyl)-1-methyl-1H-pyrazole (124 mg) and conc. sulfuric acid (1 ml) was added potassium nitrate (120 mg) at 0° C., and the mixture was stirred under nitrogen atmosphere at room temperature for 30 min, and then stirred overnight at 50° C. To the reaction mixture was added saturated aqueous sodium hydrogencarbonate solution at 0° C., and the mixture was extracted with ethyl acetate. The organic layer was washed with water and saturated brine, dried over anhydrous sodium sulfate, and concentrated under reduced pressure to give the title compound.

MS: [M+H]$^+$ 171.9.

E) 5-(methoxymethyl)-1-methyl-1H-pyrazol-4-amine

To a mixture of 5-(methoxymethyl)-1-methyl-4-nitro-1H-pyrazole (70.3 mg), THF (1 ml) and water (1 ml) was added sodium dithionite (358 mg) at room temperature, and the mixture was stirred at 60° C. for 1 hr. To the reaction mixture was added heptane, and the mixture was concentrated under reduced pressure. The residue was purified by silica gel column chromatography (ethyl acetate/MeOH) to give the title compound (20.2 mg).

MS: [M+H]$^+$ 141.9.

F) 2-(3-{[5-(methoxymethyl)-1-methyl-1H-pyrazol-4-yl]amino}-1-methyl-1H-indazol-6-yl)propan-2-ol A mixture of 2-(3-iodo-1-methyl-1H-indazol-6-yl)propan-2-ol (40.9 mg), 5-(methoxymethyl)-1-methyl-1H-pyrazol-4-amine (20.2 mg), NaO$^t$Bu (18.1 mg), BrettPhos Pd G3 (10.8 mg), BrettPhos (6.5 mg) and THF (0.6 ml) was stirred under microwave irradiation at 100° C. for 1 hr. The reaction mixture was purified by basic silica gel column chromatography (hexane/ethyl acetate), and the fraction was concentrated under reduced pressure. The obtained residue was crystallized from EtOH/ethyl acetate/hexane, and purified by HPLC, and the fraction was concentrated under reduced pressure. The obtained residue was crystallized from EtOH/ethyl acetate/hexane to give the title compound (13.2 mg).

$^1$H NMR (300 MHz, DMSO-d$_6$) δ 1.48 (6H, s), 3.26 (3H, s), 3.75-3.80 (6H, m), 4.55 (2H, s), 5.06 (1H, s), 7.07 (1H, dd, J=8.5, 1.3 Hz), 7.42 (1H, s), 7.69-7.76 (2H, m), 7.84 (1H, s).

Example 30

2-{3-[(5-ethoxy-1-methyl-1H-pyrazol-4-yl)amino]-1-methyl-1H-indazol-6-yl}propan-2-ol A) 5-ethoxy-1-methyl-4-nitro-1H-pyrazole To a mixture of 60% sodium hydride (360 mg) and DMF (25 ml) was added EtOH (0.47 ml) at 0° C., and the mixture was stirred for 5 min. To the reaction mixture was added 5-chloro-1-methyl-4-nitro-1H-pyrazole (1000 mg) at 0° C., and the mixture was stirred under nitrogen atmosphere for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (1050 mg).

MS: [M+H]$^+$ 171.9.

B) 5-ethoxy-1-methyl-1H-pyrazol-4-amine

A mixture of 5-ethoxy-1-methyl-4-nitro-1H-pyrazole (1040 mg), 10% palladium on carbon (100 mg) and MeOH (20 ml) was stirred under hydrogen atmosphere at room temperature for 3 hr. The insoluble substance was removed by filtration, and the filtrate was concentrated under reduced pressure to give the title compound (790 mg).

MS: [M+H]$^+$ 142.0.

C) 2-{3-[(5-ethoxy-1-methyl-1H-pyrazol-4-yl)amino]-1-methyl-1H-indazol-6-yl}propan-2-ol A mixture of 2-(3-iodo-1-methyl-1H-indazol-6-yl)propan-2-ol (80.9 mg), 5-ethoxy-1-methyl-1H-pyrazol-4-amine (42 mg), NaO$^t$Bu (36.1 mg), BrettPhos Pd G3 (17.8 mg), BrettPhos (10.1 mg) and THF (1 ml) was stirred under microwave irradiation at 100° C. for 1 hr. The reaction mixture was purified by basic silica gel column chromatography (hexane/ethyl acetate) and silica gel column chromatography (ethyl acetate/MeOH), and the fraction was concentrated under reduced pressure. The obtained residue was purified by HPLC, and the fraction was concentrated under reduced pressure to give the title compound (31.5 mg).

$^1$H NMR (300 MHz, DMSO-d$_6$) δ 1.23 (3H, t, J=7.2 Hz), 1.46 (6H, s), 3.59 (3H, s), 3.72 (3H, s), 4.21 (2H, q, J=7.2 Hz), 5.04 (1H, s), 7.02 (1H, dd, J=8.5, 1.3 Hz), 7.35-7.40 (2H, m), 7.45 (1H, s), 7.55 (1H, d, J=8.3 Hz).

Example 31

2-{5-fluoro-3-[(5-methoxy-1-methyl-1H-pyrazol-4-yl)amino]-1-methyl-1H-indazol-6-yl}propan-2-ol A) methyl 5-fluoro-1H-indazole-6-carboxylate A mixture of 6-bromo-5-fluoro-1H-indazole (700 mg), PdCl$_2$(dppf) (119 mg), triethylamine (1.36 ml) and MeOH (5.6 ml) was stirred under carbon monoxide pressure (50 psi) at 90° C. for 4 hr. To the reaction mixture was added water, and the mixture was extracted with ethyl acetate. The organic layer was washed with water and saturated brine, dried over anhydrous magnesium sulfate, and concentrated under reduced pressure to give the title compound (504 mg).
MS: [M+H]$^+$ 194.9.

B) 2-(5-fluoro-1H-indazol-6-yl)propan-2-ol

To methylmagnesium bromide (1 mol/l THF solution) (15.6 ml) was added a mixture of methyl 5-fluoro-1H-indazole-6-carboxylate (504 mg) and THF (21 ml) at 0° C., and the mixture was stirred under nitrogen atmosphere at 40° C. for 1 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure to give the title compound (503 mg).
MS: [M+H]$^+$ 194.9.

C) 2-(5-fluoro-3-iodo-1H-indazol-6-yl)propan-2-ol

To a mixture of 2-(5-fluoro-1H-indazol-6-yl)propan-2-ol (502 mg), potassium carbonate (714 mg) and DMF (8 ml) was added iodine (1312 mg) at 0° C., and the mixture was stirred at room temperature until the starting material disappeared. To the reaction mixture was added a mixture of sodium hydrogen sulfite (807 mg) and water (3 ml). Water was added again thereto, and the mixture was extracted with ethyl acetate. The organic layer was washed with water and saturated brine, dried over anhydrous magnesium sulfate, and concentrated under reduced pressure to give the title compound (896 mg).
MS: [M+H]$^+$ 320.8.

D) 2-(5-fluoro-3-iodo-1-methyl-1H-indazol-6-yl)propan-2-ol

To a mixture of 2-(5-fluoro-3-iodo-1H-indazol-6-yl)propan-2-ol (827 mg) and DMF (5 ml) was added cesium carbonate (1178 mg), and the mixture was stirred at room temperature for 30 min. To the reaction mixture was added dropwise a mixture of methyl iodide (0.49 ml) and DMF (1.7 ml), and the mixture was stirred overnight at room temperature. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (hexane/ethyl acetate) to give the title compound (343 mg).
MS: [M+H]$^+$ 334.8.

E) 2-{5-fluoro-3-[(5-methoxy-1-methyl-1H-pyrazol-4-yl)amino]-1-methyl-1H-indazol-6-yl}propan-2-ol A mixture of 2-(5-fluoro-3-iodo-1-methyl-1H-indazol-6-yl)propan-2-ol (100 mg), 5-methoxy-1-methyl-1H-pyrazol-4-amine (45.7 mg), NaO$^t$Bu (101 mg), BrettPhos Pd G3 (27.1 mg), BrettPhos (16.1 mg) and THF (1.5 ml) was stirred under microwave irradiation at 100° C. for 1 hr. The reaction mixture was purified by basic silica gel column chromatography (ethyl acetate/MeOH), and the fraction was concentrated under reduced pressure. The obtained residue was purified by HPLC, and the fraction was concentrated under reduced pressure to give the title compound (39 mg).
$^1$H NMR (400 MHz, DMSO-d$_6$) δ 1.51 (6H, s), 3.57-3.62 (3H, m), 3.71-3.77 (3H, m), 3.87-3.93 (3H, m), 7.34-7.40 (2H, m), 7.52 (2H, d, J=6.5 Hz).

Example 32

2-{3-[(1-ethyl-5-methoxy-1H-pyrazol-4-yl)amino]-1-methyl-1H-indazol-6-yl}propan-2-ol A) 1-ethyl-4-nitro-1H-pyrazole To a mixture of 4-nitro-1H-pyrazole (10 g), potassium carbonate (13.6 g) and DMSO (90 ml) was added ethyl iodide (7.8 ml), and the mixture was stirred at room temperature for 1 hr. To the reaction mixture was added water, and the mixture was extracted with a mixture of ethyl acetate and hexane. The organic layer was washed with water and saturated brine, dried over anhydrous sodium sulfate, and concentrated under reduced pressure. The residue was purified by silica gel column chromatography (hexane/ethyl acetate) to give the title compound (12.4 g).
$^1$H NMR (300 MHz, DMSO-d$_6$) δ 1.40 (3H, t, J=7.2 Hz), 4.20 (2H, q, J=7.4 Hz), 8.25 (1H, s), 8.90 (1H, s).

B) 5-chloro-1-ethyl-4-nitro-1H-pyrazole

To a mixture of 1-ethyl-4-nitro-1H-pyrazole (10 g) and THF (100 ml) was added a solution of lithium (bistrimethylsilyl)amide in THF (1.3 mol/l, 60 ml) while keeping the internal temperature within −75° C. to −70° C., and the mixture was stirred for 30 min. To the reaction mixture was added hexachloroethane (20 g) at −78° C., and the mixture was stirred under nitrogen atmosphere at −78° C. for 1 hr, and then stirred overnight at room temperature. To the reaction mixture was added saturated aqueous ammonium chloride solution at 0° C., and the mixture was extracted with a mixture of ethyl acetate and hexane. The organic layer was washed with water and saturated brine, dried over anhydrous sodium sulfate, and concentrated under reduced pressure. The residue was purified by silica gel column chromatography (hexane/ethyl acetate) to give the title compound (5.67 g).
$^1$H NMR (300 MHz, DMSO-d$_6$) δ 1.37 (3H, t, J=7.2 Hz), 4.24 (2H, q, J=7.2 Hz), 8.46 (1H, s).

C) 1-ethyl-5-methoxy-4-nitro-1H-pyrazole

To a mixture of 60% sodium hydride (322 mg) and DMF (18 ml) was added MeOH (0.3 ml) at 0° C., and the mixture was stirred for 5 min. To the reaction mixture was added 5-chloro-1-ethyl-4-nitro-1H-pyrazole (1000 mg) at 0° C., and the mixture was stirred under nitrogen atmosphere for 1 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (860 mg).
MS: [M+H]$^+$ 171.9.

D) 1-ethyl-5-methoxy-1H-pyrazol-4-amine

A mixture of 1-ethyl-5-methoxy-4-nitro-1H-pyrazole (860 mg), 10% palladium on carbon (85.3 mg) and MeOH (20 ml) was stirred under hydrogen atmosphere at room temperature for 3 hr. The insoluble substance was removed by filtration, and the filtrate was concentrated under reduced pressure to give the title compound (620 mg).
MS: [M+H]$^+$ 142.0.

E) 2-{3-[(1-ethyl-5-methoxy-1H-pyrazol-4-yl)amino]-1-methyl-1H-indazol-6-yl}propan-2-ol A mixture of 2-(3-iodo-1-methyl-1H-indazol-6-yl)propan-2-ol (80.9 mg), 1-ethyl-5-methoxy-1H-pyrazol-4-amine (40 mg), NaO$^t$Bu (36.1 mg), BrettPhos Pd G3 (17.8 mg), BrettPhos (10.1 mg) and THF (1 ml) was stirred under microwave irradiation at 100° C. for 1 hr. The reaction mixture was purified by silica gel column chromatography (ethyl acetate/MeOH) and basic silica gel column chromatography (hexane/ethyl acetate) to give the title compound (47.4 mg).
$^1$H NMR (300 MHz, DMSO-d$_6$) δ 1.29 (3H, t, J=7.2 Hz), 1.46 (6H, s), 3.73 (3H, s), 3.86-3.98 (5H, m), 5.04 (1H, s), 7.02 (1H, dd, J=8.5, 1.3 Hz), 7.34-7.41 (2H, m), 7.45-7.56 (2H, m).

Example 33

2-[1-methyl-3-({1-methyl-5-[(propan-2-yl)oxy]-1H-pyrazol-4-yl}amino)-1H-indazol-6-yl]propan-2-ol A) 1-methyl-4-nitro-5-[(propan-2-yl)oxy]-1H-pyrazole To a mixture of 60% sodium hydride (360 mg) and DMF (25 ml) was added 2-propanol (0.66 ml) at 0° C., and the mixture was stirred for 5 min. To the reaction mixture was added 5-chloro-1-methyl-4-nitro-1H-pyrazole (1000 mg) at 0° C., and the mixture was stirred under nitrogen atmosphere at room temperature for 4 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (784 mg).
$^1$H NMR (300 MHz, DMSO-d$_6$) δ 1.36 (6H, d, J=6.1 Hz), 3.67 (3H, s), 4.80-4.95 (1H, m), 8.16 (1H, s).

B) 1-methyl-5-[(propan-2-yl)oxy]-1H-pyrazol-4-amine

A mixture of 1-methyl-4-nitro-5-[(propan-2-yl)oxy]-1H-pyrazole (784 mg), 10% palladium on carbon (78.3 mg) and MeOH (20 ml) was stirred under hydrogen atmosphere at room temperature for 2 hr. The insoluble substance was removed by filtration, and the filtrate was concentrated under reduced pressure. The residue was purified by basic silica gel column chromatography (hexane/ethyl acetate) to give the title compound (531 mg).
$^1$H NMR (300 MHz, DMSO-d$_6$) δ 1.24 (6H, d, J=6.1 Hz), 3.28-3.40 (2H, m), 3.47 (3H, s), 4.40-4.55 (1H, m), 6.86 (1H, s).

C) 2-[1-methyl-3-({1-methyl-5-[(propan-2-yl)oxy]-1H-pyrazol-4-yl}amino)-1H-indazol-6-yl]propan-2-ol A mixture of 2-(3-iodo-1-methyl-1H-indazol-6-yl)propan-2-ol (80.9 mg), 1-methyl-5-[(propan-2-yl)oxy]-1H-pyrazol-4-amine (44 mg), NaO$^t$Bu (36.1 mg), BrettPhos Pd G3 (17.8 mg), BrettPhos (10.1 mg) and THF (1 ml) was stirred under microwave irradiation at 100° C. for 1 hr. The reaction mixture was purified by silica gel column chromatography (ethyl acetate/MeOH) and basic silica gel column chromatography (hexane/ethyl acetate) to give the title compound (50.2 mg).
$^1$H NMR (300 MHz, DMSO-d$_6$) δ 1.21 (6H, d, J=6.1 Hz), 1.46 (6H, s), 3.58 (3H, s), 3.72 (3H, s), 4.56-4.70 (1H, m), 5.04 (1H, s), 7.01 (1H, dd, J=8.5, 1.3 Hz), 7.36-7.45 (3H, m), 7.55 (1H, d, J=8.3 Hz).

Example 34

2-{1-ethyl-3-[(5-methoxy-1-methyl-1H-pyrazol-4-yl)amino]-1H-indazol-6-yl}propan-2-ol A) 2-(1-ethyl-3-iodo-1H-indazol-6-yl)propan-2-ol To a mixture of 2-(3-iodo-1H-indazol-6-yl)propan-2-ol (1.15 g) and DMF (7 ml) was added potassium carbonate (0.68 g), and the mixture was stirred at room temperature for 30 min. To the reaction mixture was added dropwise a mixture of ethyl iodide (0.92 ml) and DMF (2.3 ml), and the mixture was stirred overnight at room temperature. The reaction mixture was poured into water, and extracted with ethyl acetate. The organic layer was washed with water and saturated brine, dried over anhydrous magnesium sulfate, and concentrated under reduced pressure. The residue was purified by silica gel column chromatography (hexane/ethyl acetate) to give the title compound (0.88 g).
MS: [M+H]$^+$ 330.9.

B) 2-{1-ethyl-3-[(5-methoxy-1-methyl-1H-pyrazol-4-yl)amino]-1H-indazol-6-yl}propan-2-ol A mixture of 2-(1-ethyl-3-iodo-1H-indazol-6-yl)propan-2-ol (100 mg), 5-methoxy-1-methyl-1H-pyrazol-4-amine (46.2 mg), NaO$^t$Bu (102 mg), BrettPhos Pd G3 (27.5 mg), BrettPhos (16.3 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was crystallized from EtOH/hexane to give the title compound (28 mg).
$^1$H NMR (400 MHz, DMSO-d$_6$) δ 1.26 (3H, t, J=7.1 Hz), 1.46 (6H, s), 3.59 (3H, s), 3.90 (3H, s), 4.13 (2H, q, J=7.1 Hz), 5.02 (1H, s), 7.01 (1H, dd, J=8.5, 1.2 Hz), 7.38 (1H, s), 7.41 (1H, s), 7.49 (1H, s), 7.54 (1H, d, J=8.4 Hz).

Example 35

2-(3-{[5-methoxy-1-(propan-2-yl)-1H-pyrazol-4-yl]amino}-1-methyl-1H-indazol-6-yl)propan-2-ol A) 4-nitro-1-(propan-2-yl)-1H-pyrazole To a mixture of 4-nitro-1H-pyrazole (10 g), potassium carbonate (13.6 g) and DMSO (90 ml) was added 2-iodopropane (9.8 ml), and the mixture was stirred at 40° C. for 3 hr. To the reaction mixture was added water, and the mixture was extracted with a mixture of ethyl acetate and hexane. The organic layer was washed with water and saturated brine, dried over anhydrous sodium sulfate, and concentrated under reduced pressure. The residue was purified by silica gel column chromatography (hexane/ethyl acetate) to give the title compound (12.5 g).
¹H NMR (300 MHz, DMSO-d₆) δ 1.45 (6H, d, J=6.4 Hz), 4.50-4.67 (1H, m), 8.25 (1H, s), 8.92 (1H, s).

B) 5-chloro-4-nitro-1-(propan-2-yl)-1H-pyrazole

To a mixture of 4-nitro-1-(propan-2-yl)-1H-pyrazole (10 g) and THF (100 ml) was added a solution of lithium (bistrimethylsilyl)amide in THF (1.3 mol/l, 55 ml) while keeping the internal temperature within −75° C. to −70° C., and the mixture was stirred for 30 min. To the reaction mixture was added hexachloroethane (18.5 g) at −78° C., and the mixture was stirred under nitrogen atmosphere at −78° C. for 1 hr, and then stirred overnight at room temperature. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (8.96 g).
¹H NMR (300 MHz, DMSO-d₆) δ 1.42 (6H, d, J=6.8 Hz), 4.70-4.86 (1H, m), 8.48 (1H, s).

C) 5-methoxy-4-nitro-1-(propan-2-yl)-1H-pyrazole

To a mixture of 60% sodium hydride (292 mg) and DMF (20 ml) was added MeOH (0.28 ml) at 0° C., and the mixture was stirred for 5 min. To the reaction mixture was added 5-chloro-4-nitro-1-(propan-2-yl)-1H-pyrazole (1000 mg) at 0° C., and the mixture was stirred under nitrogen atmosphere for 1 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (926 mg).
MS: [M+H]⁺ 185.9.

D) 5-methoxy-1-(propan-2-yl)-1H-pyrazol-4-amine

A mixture of 5-methoxy-4-nitro-1-(propan-2-yl)-1H-pyrazole (926 mg), 10% palladium on carbon (93.3 mg) and MeOH (20 ml) was stirred under hydrogen atmosphere at room temperature overnight. The insoluble substance was removed by filtration, and the filtrate was concentrated under reduced pressure. The residue was purified by basic silica gel column chromatography (hexane/ethyl acetate) to give the title compound (622 mg).
MS: [M+H]⁺ 155.9.

E) 2-(3-{[5-methoxy-1-(propan-2-yl)-1H-pyrazol-4-yl]amino}-1-methyl-1H-indazol-6-yl)propan-2-ol A mixture of 2-(3-iodo-1-methyl-1H-indazol-6-yl)propan-2-ol (80.8 mg), 5-methoxy-1-(propan-2-yl)-1H-pyrazol-4-amine (43 mg), NaO^tBu (38.1 mg), BrettPhos Pd G3 (18.3 mg), BrettPhos (11.1 mg) and THF (1.0 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was purified by HPLC to give the title compound (42.1 mg).
¹H NMR (300 MHz, DMSO-d₆) δ 1.35 (6H, d, J=6.8 Hz), 1.46 (6H, s), 3.73 (3H, s), 3.90 (3H, s), 4.38-4.50 (1H, m), 5.04 (1H, s), 7.01 (1H, dd, J=8.5, 1.3 Hz), 7.37-7.41 (2H, m), 7.44-7.53 (2H, m).

Example 36

2-{1-ethyl-3-[(3-methoxy-1-methyl-1H-pyrazol-4-yl)amino]-1H-indazol-6-yl}propan-2-ol A mixture of 2-(1-ethyl-3-iodo-1H-indazol-6-yl)propan-2-ol (100 mg), 3-methoxy-1-methyl-1H-pyrazol-4-amine hydrochloride (49.6 mg), NaO^tBu (102 mg), BrettPhos Pd G3 (27.5 mg), BrettPhos (16.3 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was crystallized from EtOH/hexane to give the title compound (20 mg).
¹H NMR (400 MHz, DMSO-d₆) δ 1.32 (3H, t, J=7.1 Hz), 1.47 (6H, s), 3.68 (3H, s), 3.85 (3H, s), 4.17 (2H, q, J=7.1 Hz), 5.02 (1H, s), 7.02 (1H, dd, J=8.6, 1.2 Hz), 7.41 (1H, s), 7.79-7.88 (3H, m).

Example 37

2-{3-[(5-methoxy-1-methyl-1H-pyrazol-4-yl)amino]-1-(propan-2-yl)-1H-indazol-6-yl}propan-2-ol A mixture of 2-[3-iodo-1-(propan-2-yl)-1H-indazol-6-yl]propan-2-ol (100 mg), 5-methoxy-1-methyl-1H-pyrazol-4-amine (44.3 mg), NaO^tBu (98 mg), BrettPhos Pd G3 (26.3 mg), BrettPhos (15.6 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was purified by HPLC to give the title compound (19.4 mg).
¹H NMR (300 MHz, DMSO-d₆) δ 1.36 (6H, d, J=6.8 Hz), 1.46 (6H, s), 3.60 (3H, s), 3.91 (3H, s), 4.63-4.76 (1H, m), 5.02 (1H, s), 6.99 (1H, dd, J=8.5, 1.3 Hz), 7.44 (2H, s), 7.50 (1H, d, J=8.7 Hz), 7.55 (1H, s).

Example 38

2-{1-(cyclopropylmethyl)-3-[(5-methoxy-1-methyl-1H-pyrazol-4-yl)amino]-1H-indazol-6-yl}propan-2-ol A mixture of 2-[1-(cyclopropylmethyl)-3-iodo-1H-indazol-6-yl]propan-2-ol (100 mg), 5-methoxy-1-methyl-1H-pyrazol-4-amine (42.8 mg), NaO^tBu (94 mg), BrettPhos Pd G3 (25.4 mg), BrettPhos (15.1 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was purified by HPLC to give the title compound (22.9 mg).

¹H NMR (300 MHz, DMSO-d₆) δ 0.27-0.48 (4H, m), 1.09-1.22 (1H, m), 1.46 (6H, s), 3.60 (3H, s), 3.91 (3H, s), 4.00 (2H, d, J=6.8 Hz), 5.02 (1H, s), 7.01 (1H, dd, J=8.5, 1.3 Hz), 7.40 (1H, s), 7.43 (1H, s), 7.49-7.57 (2H, m).

Example 39

2-{3-[(3-methoxy-1-methyl-1H-pyrazol-4-yl)amino]-1-(propan-2-yl)-1H-indazol-6-yl}propan-2-ol A mixture of 2-[3-iodo-1-(propan-2-yl)-1H-indazol-6-yl]propan-2-ol (80.3 mg), 3-methoxy-1-methyl-1H-pyrazol-4-amine hydrochloride (40.6 mg), NaO$^t$Bu (65.2 mg), BrettPhos Pd G3 (11.5 mg), BrettPhos (6.9 mg) and THF (1.3 ml) was stirred under microwave irradiation at 100° C. for 1 hr. The reaction mixture was purified by basic silica gel column chromatography (ethyl acetate/MeOH) and silica gel column chromatography (hexane/ethyl acetate) to give the title compound (49.4 mg).
¹H NMR (300 MHz, DMSO-d₆) δ 1.41 (6H, d, J=6.8 Hz), 1.47 (6H, s), 3.68 (3H, s), 3.85 (3H, s), 4.65-4.80 (1H, m), 5.03 (1H, s), 7.00 (1H, dd, J=8.5, 1.3 Hz), 7.44 (1H, s), 7.77-7.93 (3H, m).

Example 40

2-(3-{[5-methoxy-1-(2-methylpropyl)-1H-pyrazol-4-yl]amino}-1-methyl-1H-indazol-6-yl)propan-2-ol A mixture of 2-(3-iodo-1-methyl-1H-indazol-6-yl)propan-2-ol (80.5 mg), 5-methoxy-1-(2-methylpropyl)-1H-pyrazol-4-amine (48.5 mg), NaO$^t$Bu (38.7 mg), BrettPhos Pd G3 (15.3 mg), BrettPhos (9.1 mg) and THF (1 ml) was stirred under microwave irradiation at 100° C. for 1 hr. The reaction mixture was purified by basic silica gel column chromatography (hexane/ethyl acetate) and silica gel column chromatography (hexane/ethyl acetate) to give the title compound (56.7 mg).
¹H NMR (300 MHz, DMSO-d₆) δ 0.86 (6H, d, J=6.8 Hz), 1.46 (6H, s), 2.01-2.15 (1H, m), 3.66-3.76 (5H, m), 3.90 (3H, s), 5.04 (1H, s), 7.00 (1H, dd, J=8.7, 1.5 Hz), 7.39 (2H, s), 7.46-7.53 (2H, m).

Example 41

2-{3-[(3-methoxy-1-methyl-1H-pyrazol-4-yl)amino]-1-methyl-1H-indazol-5-yl}propan-2-ol A) 2-(1H-indazol-5-yl)propan-2-ol To a mixture of methyl 1H-indazole-5-carboxylate (3 g) and THF (60 ml) was added methylmagnesium bromide (3 mol/l, Et₂O solution) (34.1 ml) at 0° C., and the mixture was stirred under nitrogen atmosphere at 40° C. for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure to give the title compound (2.91 g).
MS: [M+H]⁺ 176.9.

B) 2-(3-iodo-1H-indazol-5-yl)propan-2-ol

To a mixture of 2-(1H-indazol-5-yl)propan-2-ol (2.91 g), potassium carbonate (4.56 g) and DMF (46 ml) was added iodine (8.38 g) at 0° C., and the mixture was stirred at room temperature until the starting material disappeared. To the reaction mixture was added a mixture of sodium hydrogen sulfite (5.16 g) and water (15 ml). Water was added again thereto, and the mixture was extracted with ethyl acetate. The organic layer was dried over anhydrous magnesium sulfate, and concentrated under reduced pressure to give the title compound (4.37 g).
MS: [M+H]⁺ 302.8.

C) 2-(3-iodo-1-methyl-1H-indazol-5-yl)propan-2-ol

To a mixture of 2-(3-iodo-1H-indazol-5-yl)propan-2-ol (4.37 g) and DMF (26.2 ml) was added cesium carbonate (6.6 g), and the mixture was stirred at room temperature for 30 min. To the reaction mixture was added dropwise a mixture of methyl iodide (2.7 ml) and DMF (8.7 ml), and the mixture was stirred overnight at room temperature. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (hexane/ethyl acetate) to give the title compound (3.77 g).
MS: [M+H]⁺ 316.9.

D) 2-{3-[(3-methoxy-1-methyl-1H-pyrazol-4-yl)amino]-1-methyl-1H-indazol-5-yl}propan-2-ol A mixture of 2-(3-iodo-1-methyl-1H-indazol-5-yl)propan-2-ol (100 mg), 3-methoxy-1-methyl-1H-pyrazol-4-amine hydrochloride (51.8 mg), NaO$^t$Bu (106 mg), BrettPhos Pd G3 (28.7 mg), BrettPhos (17 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was crystallized from EtOH/hexane to give the title compound (24.6 mg).
¹H NMR (400 MHz, DMSO-d₆) δ 1.47 (6H, s), 3.67 (3H, s), 3.73-3.79 (3H, m), 3.85 (3H, s), 4.89 (1H, s), 7.26 (1H, d, J=8.8 Hz), 7.50 (1H, dd, J=8.8, 1.6 Hz), 7.83 (1H, s), 7.92 (1H, s), 8.05 (1H, d, J=0.9 Hz).

Example 42

2-{3-[(5-methoxy-1-methyl-1H-pyrazol-4-yl)amino]-1-methyl-1H-indazol-5-yl}propan-2-ol A mixture of 2-(3-iodo-1-methyl-1H-indazol-5-yl)propan-2-ol (120 mg), 5-methoxy-1-methyl-1H-pyrazol-4-amine (48.3 mg), NaO$^t$Bu (128 mg), BrettPhos Pd G3 (34.4 mg), BrettPhos (20.4 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was purified by HPLC, and the fraction was concentrated under reduced pressure. The obtained residue was crystallized from EtOH/hexane to give the title compound (12 mg).
¹H NMR (400 MHz, DMSO-d₆) δ 1.46 (6H, s), 3.59 (3H, s), 3.72 (3H, s), 3.91 (3H, s), 4.92 (1H, s), 7.25 (1H, d, J=8.8 Hz), 7.38 (1H, s), 7.45 (1H, dd, J=8.8, 1.7 Hz), 7.55 (1H, s), 7.85 (1H, d, J=1.0 Hz).

Example 43

2-{3-[(1-ethyl-3-methyl-1H-pyrazol-4-yl)amino]-1-methyl-1H-indazol-6-yl}propan-2-ol A mixture of 2-(3-iodo-1-methyl-1H-indazol-6-yl)propan-2-ol (80.5 mg), 1-ethyl-3-methyl-1H-pyrazol-4-amine dihydrochloride (62.4 mg), NaO$^t$Bu (86.7 mg), BrettPhos Pd G3 (15.3 mg), BrettPhos (8.7 mg) and THF (1.5 ml) was stirred under microwave irradiation at 100° C. for 1 hr. The reaction mixture was purified by basic silica gel column chromatography (hexane/ethyl acetate) and silica gel column chromatography (hexane/ethyl acetate), and the fraction was concentrated under reduced pressure. The obtained residue was crystallized from EtOH/water to give the title compound (33.1 mg).

$^1$H NMR (300 MHz, DMSO-d$_6$) δ 1.34 (3H, t, J=7.2 Hz), 1.48 (6H, s), 2.18 (3H, s), 3.79 (3H, s), 4.01 (2H, q, J=7.2 Hz), 5.05 (1H, s), 7.04-7.11 (1H, m), 7.41 (1H, s), 7.73-7.81 (2H, m), 7.91 (1H, s).

Example 44

2-(4-fluoro-3-{[5-methoxy-1-(2-methylpropyl)-1H-pyrazol-4-yl]amino}-1-methyl-1H-indazol-6-yl)propan-2-ol

A) methyl 4-fluoro-1H-indazole-6-carboxylate

A mixture of 6-bromo-4-fluoro-1H-indazole (4 g), PdCl$_2$ (dppf) (0.68 g), triethylamine (7.77 ml) and MeOH (32 ml) was stirred under carbon monoxide pressure (50 psi) at 90° C. for 4 hr. To the reaction mixture was added water, and the resulting solid was collected by filtration, washed with water, and dried under reduced pressure to give the title compound (3.46 g).

MS: [M+H]$^+$ 194.9.

B) 2-(4-fluoro-1H-indazol-6-yl)propan-2-ol

To a mixture of methyl 4-fluoro-1H-indazole-6-carboxylate (1.7 g) and THF (30 ml) was added methylmagnesium bromide (3 mol/l Et$_2$O solution) (15 ml) at 0° C., and the mixture was stirred under nitrogen atmosphere at 30° C. for 1 hr. To the reaction mixture was added saturated aqueous citric acid solution at 0° C., and the mixture was extracted with ethyl acetate. The organic layer was washed with water and saturated brine, dried over anhydrous sodium sulfate, and filtered through Celite, and the filtrate was concentrated under reduced pressure to give the title compound (1.7 g).

MS: [M+H]$^+$ 194.9.

C) 2-(4-fluoro-3-iodo-1H-indazol-6-yl)propan-2-ol

To a mixture of 2-(4-fluoro-1H-indazol-6-yl)propan-2-ol (1.7 g), potassium carbonate (2.43 g) and DMF (30 ml) was added iodine (4.45 g) at 0° C., and the mixture was stirred at room temperature for 2 hr. To the reaction mixture was added a mixture of sodium hydrogen sulfite (2 g) and water (60 ml) at 0° C., water was added again thereto, and the mixture was extracted with a mixture of ethyl acetate and hexane. The organic layer was dried over anhydrous sodium sulfate, and concentrated under reduced pressure to give the title compound (2.8 g).

MS: [M+H]$^+$ 320.8.

D) 2-(4-fluoro-3-iodo-1-methyl-1H-indazol-6-yl)propan-2-ol

To a mixture of 2-(4-fluoro-3-iodo-1H-indazol-6-yl)propan-2-ol (2.8 g), cesium carbonate (4.35 g) and DMF (20 ml) was added methyl iodide (0.83 ml), and the mixture was stirred overnight at room temperature. To the reaction mixture was added water, and the mixture was extracted with a mixture of ethyl acetate and hexane. The organic layer was washed with water and saturated brine, dried over anhydrous sodium sulfate, and concentrated under reduced pressure. The residue was purified by silica gel column chromatography (hexane/ethyl acetate) to give the title compound (0.95 g).

MS: [M+H]$^+$ 334.8.

E) 1-(2-methylpropyl)-4-nitro-1H-pyrazole

To a mixture of 4-nitro-1H-pyrazole (10 g), potassium carbonate (13.6 g) and DMSO (90 ml) was added 1-bromo-2-methylpropane (10.8 ml) at room temperature, and the mixture was stirred under nitrogen atmosphere at 60° C. for 3 hr. To the reaction mixture was added water, and the mixture was extracted with a mixture of ethyl acetate and hexane. The organic layer was washed with water and saturated brine, dried over anhydrous sodium sulfate, and concentrated under reduced pressure. The residue was purified by silica gel column chromatography (hexane/ethyl acetate) to give the title compound (14.6 g).

$^1$H NMR (300 MHz, DMSO-d$_6$) δ 0.85 (6H, d, J=6.8 Hz), 2.15 (1H, m), 4.00 (2H, d, J=7.2 Hz), 8.26 (1H, d, J=0.8 Hz), 8.90 (1H, s).

F) 5-chloro-1-(2-methylpropyl)-4-nitro-1H-pyrazole

To a mixture of 1-(2-methylpropyl)-4-nitro-1H-pyrazole (10 g) and THF (90 ml) was added a solution of lithium (bistrimethylsilyl)amide in THF (1.3 mol/l, 50 ml) while keeping the internal temperature within −75° C. to −70° C., and the mixture was stirred for 30 min. To the reaction mixture was added hexachloroethane (16.8 g) at −78° C., and the mixture was stirred under nitrogen atmosphere at −78° C. for 20 min, and the mixture was stirred at room temperature for 1 hr. To the reaction mixture was added saturated aqueous ammonium chloride solution at 0° C., and the mixture was extracted with a mixture of ethyl acetate and hexane. The organic layer was washed with water and saturated brine, dried over anhydrous sodium sulfate, and concentrated under reduced pressure. The residue was purified by silica gel column chromatography (hexane/ethyl acetate) to give the title compound (11 g).

MS: [M+H]$^+$ 203.9.

G) 5-methoxy-1-(2-methylpropyl)-4-nitro-1H-pyrazole

To a mixture of 60% sodium hydride (280 mg) and DMF (15 ml) was added MeOH (0.26 ml) at 0° C., and the mixture was stirred for 3 min. To the reaction mixture was added a mixture of 5-chloro-1-(2-methylpropyl)-4-nitro-1H-pyrazole (1000 mg) and DMF (5 ml), and the mixture was stirred under nitrogen atmosphere at 0° C. for 3 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (739 mg).
MS: [M+H]$^+$ 199.9.

H) 5-methoxy-1-(2-methylpropyl)-1H-pyrazol-4-amine

A mixture of 5-methoxy-1-(2-methylpropyl)-4-nitro-1H-pyrazole (739 mg), 10% palladium on carbon (70.3 mg) and MeOH (20 ml) was stirred under hydrogen atmosphere at room temperature for 4 hr. The insoluble substance was removed by filtration, and the filtrate was concentrated under reduced pressure. The residue was purified by basic silica gel column chromatography (hexane/ethyl acetate) to give the title compound (500 mg).
MS: [M+H]$^+$ 169.9.

I) 2-(4-fluoro-3-{[5-methoxy-1-(2-methylpropyl)-1H-pyrazol-4-yl]amino}-1-methyl-1H-indazol-6-yl)propan-2-ol A mixture of 2-(4-fluoro-3-iodo-1-methyl-1H-indazol-6-yl)propan-2-ol (100 mg), 5-methoxy-1-(2-methylpropyl)-1H-pyrazol-4-amine (58 mg), NaO$^t$Bu (43.2 mg), BrettPhos Pd G3 (20.5 mg), BrettPhos (12.3 mg) and THF (1.5 ml) was stirred under microwave irradiation at 100° C. for 1 hr. The reaction mixture was purified by basic silica gel column chromatography (hexane/ethyl acetate) and silica gel column chromatography (hexane/ethyl acetate), and the fraction was concentrated under reduced pressure. The obtained residue was purified by HPLC to give the title compound (65.8 mg).
$^1$H NMR (300 MHz, DMSO-d$_6$) δ 0.86 (6H, d, J=6.8 Hz), 1.46 (6H, s), 1.96-2.15 (1H, m), 3.68 (2H, d, J=7.6 Hz), 3.73 (3H, s), 3.92 (3H, s), 5.16 (1H, s), 6.77 (1H, dd, J=12.5, 1.1 Hz), 7.02 (1H, s), 7.21 (1H, s), 7.28 (1H, s).

Example 45

2-{3-[(1-ethyl-3-methyl-1H-pyrazol-4-yl)amino]-4-fluoro-1-methyl-1H-indazol-6-yl}propan-2-ol A mixture of 2-(4-fluoro-3-iodo-1-methyl-1H-indazol-6-yl)propan-2-ol (100 mg), 1-ethyl-3-methyl-1H-pyrazol-4-amine dihydrochloride (65.2 mg), NaO$^t$Bu (101 mg), BrettPhos Pd G3 (27.1 mg), BrettPhos (16.1 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was crystallized from ethyl acetate/hexane to give the title compound (53 mg).
$^1$H NMR (400 MHz, DMSO-d$_6$) δ 1.34 (3H, t, J=7.3 Hz), 1.47 (6H, s), 2.11 (3H, s), 3.79 (3H, s), 4.01 (2H, q, J=7.2 Hz), 5.16 (1H, s), 6.81 (1H, d, J=12.5 Hz), 7.09 (1H, s), 7.23 (1H, s), 7.79 (1H, s).

Example 46

2-{4-fluoro-3-[(3-methoxy-1-methyl-1H-pyrazol-4-yl)amino]-1-methyl-1H-indazol-6-yl}propan-2-ol A mixture of 2-(4-fluoro-3-iodo-1-methyl-1H-indazol-6-yl)propan-2-ol (102 mg), 3-methoxy-1-methyl-1H-pyrazol-4-amine hydrochloride (58 mg), NaO$^t$Bu (64 mg), BrettPhos Pd G3 (20.5 mg), BrettPhos (12.3 mg) and THF (1.5 ml) was stirred under microwave irradiation at 100° C. for 1 hr. The reaction mixture was purified by basic silica gel column chromatography (hexane/ethyl acetate) and silica gel column chromatography (hexane/ethyl acetate), and the fraction was concentrated under reduced pressure. The obtained residue was crystallized from ethyl acetate/heptane to give the title compound (69.9 mg).
$^1$H NMR (300 MHz, DMSO-d$_6$) δ 1.46 (6H, s), 3.67 (3H, s), 3.79 (3H, s), 3.82 (3H, s), 5.18 (1H, s), 6.72 (1H, s), 6.81 (1H, dd, J=12.5, 0.8 Hz), 7.24 (1H, s), 7.73 (1H, s).

Example 47

2-(3-{[5-(1-methoxyethyl)-1-methyl-1H-pyrazol-4-yl]amino}-1-methyl-1H-indazol-6-yl)propan-2-ol A mixture of 2-(3-iodo-1-methyl-1H-indazol-6-yl)propan-2-ol (102 mg), 5-(1-methoxyethyl)-1-methyl-1H-pyrazol-4-amine (55.2 mg), NaO$^t$Bu (47.1 mg), BrettPhos Pd G3 (20.8 mg), BrettPhos (12 mg) and THF (1.5 ml) was stirred under microwave irradiation at 100° C. for 1 hr. The reaction mixture was purified by basic silica gel column chromatography (hexane/ethyl acetate) and silica gel column chromatography (hexane/ethyl acetate) to give the title compound (57.7 mg).
$^1$H NMR (300 MHz, DMSO-d$_6$) δ 1.42-1.50 (9H, m), 3.14 (3H, s), 3.75 (3H, s), 3.84 (3H, s), 4.71 (1H, q, J=6.8 Hz), 5.06 (1H, s), 7.06 (1H, dd, J=8.5, 1.3 Hz), 7.41 (1H, s), 7.52 (1H, s), 7.57-7.64 (2H, m).

Example 48

2-(4-fluoro-3-{[5-(1-methoxyethyl)-1-methyl-1H-pyrazol-4-yl]amino}-1-methyl-1H-indazol-6-yl)propan-2-ol A) 1-(1-methyl-1H-pyrazol-5-yl)ethan-1-ol To a mixture of methylmagnesium bromide (3 mol/l Et$_2$O solution) (15 ml) and THF (50 ml) was added a mixture of 1-methyl-1H-pyrazole-5-carbaldehyde (3 g) and THF (10 ml) at 0° C., and the mixture was stirred under nitrogen atmosphere at room temperature for 1 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure to give the title compound (1.97 g).
MS: [M+H]$^+$ 126.9.

B) 5-(1-methoxyethyl)-1-methyl-1H-pyrazole

To a mixture of 1-(1-methyl-1H-pyrazol-5-yl)ethan-1-ol (1.97 g) and DMF (40 ml) was added 60% sodium hydride (750 mg) at 0° C., and the mixture was stirred for 5 min. To the reaction mixture was added methyl iodide (1.3 ml) at 0° C., and the mixture was stirred overnight at room temperature. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (1.44 g).
MS: [M+H]$^+$ 140.9.

C) 5-(1-methoxyethyl)-1-methyl-4-nitro-1H-pyrazole

To a mixture of 5-(1-methoxyethyl)-1-methyl-1H-pyrazole (1.44 g) and conc. sulfuric acid (10 ml) was added potassium nitrate (1.3 g) at 0° C., and the mixture was stirred under nitrogen atmosphere at room temperature for 10 min, and then stirred overnight at 50° C. To the reaction mixture was added saturated aqueous sodium hydrogencarbonate solution at 0° C., and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (1.16 g).

MS: [M+H]$^+$ 185.9.

D) 5-(1-methoxyethyl)-1-methyl-1H-pyrazol-4-amine

A mixture of 5-(1-methoxyethyl)-1-methyl-4-nitro-1H-pyrazole (1.16 g), 10% palladium on carbon (114 mg) and MeOH (30 ml) was stirred under hydrogen atmosphere at room temperature for 5 hr. The insoluble substance was removed by filtration, and the filtrate was concentrated under reduced pressure. The residue was purified by basic silica gel column chromatography (hexane/ethyl acetate) to give the title compound (0.96 g).

MS: [M+H]$^+$ 155.9.

E) 2-(4-fluoro-3-{[5-(1-methoxyethyl)-1-methyl-1H-pyrazol-4-yl]amino}-1-methyl-1H-indazol-6-yl)propan-2-ol A mixture of 2-(4-fluoro-3-iodo-1-methyl-1H-indazol-6-yl)propan-2-ol (102 mg), 5-(1-methoxyethyl)-1-methyl-1H-pyrazol-4-amine (55.2 mg), NaO$^t$Bu (47.1 mg), BrettPhos Pd G3 (20.8 mg), BrettPhos (12 mg) and THF (1.5 ml) was stirred under microwave irradiation at 100° C. for 1 hr. The reaction mixture was purified by basic silica gel column chromatography (hexane/ethyl acetate) and silica gel column chromatography (hexane/ethyl acetate) to give the title compound (79 mg).

$^1$H NMR (300 MHz, DMSO-d$_6$) δ 1.41-1.48 (9H, m), 3.22 (3H, s), 3.79 (6H, s), 4.68 (1H, q, J=6.8 Hz), 5.18 (1H, s), 6.82 (1H, dd, J=12.5, 0.8 Hz), 7.18 (1H, s), 7.24 (1H, s), 7.65 (1H, s).

Example 49

2-{1-(cyclopropylmethyl)-3-[(3-methoxy-1-methyl-1H-pyrazol-4-yl)amino]-1H-indazol-6-yl}propan-2-ol

A) 2-(1H-indazol-6-yl)propan-2-ol

To a mixture of methyl 1H-indazole-6-carboxylate (6 g) and THF (120 ml) was added methylmagnesium bromide (3 mol/l Et$_2$O solution) (68 ml) at 0° C., and the mixture was stirred under nitrogen atmosphere at 40° C. for 2 hr. To the reaction mixture was added saturated aqueous ammonium chloride solution at 0° C., and the mixture was extracted with ethyl acetate. The organic layer was washed with water and saturated brine, dried over anhydrous sodium sulfate, and concentrated under reduced pressure to give the title compound (5.86 g).

MS: [M+H]$^+$ 176.9.

B) 2-(3-iodo-1H-indazol-6-yl)propan-2-ol

To a mixture of 2-(1H-indazol-6-yl)propan-2-ol (5.86 g), potassium carbonate (9.19 g) and DMF (94 ml) was added iodine (16.88 g) at 0° C., and the mixture was stirred at room temperature until the starting material disappeared. To the reaction mixture was added a mixture of sodium hydrogen sulfite (10.38 g) and water (15 ml). Water was added again thereto, and the mixture was extracted with ethyl acetate. The organic layer was dried over anhydrous magnesium sulfate, and concentrated under reduced pressure to give the title compound (9.15 g).

MS: [M+H]$^+$ 302.8.

C) 2-[1-(cyclopropylmethyl)-3-iodo-1H-indazol-6-yl]propan-2-ol

To a mixture of 2-(3-iodo-1H-indazol-6-yl)propan-2-ol (1.18 g) and DMF (7 ml) was added potassium carbonate (0.81 g), and the mixture was stirred at room temperature for 30 min. To the reaction mixture was added dropwise a mixture of (bromomethyl)cyclopropane (1.71 ml) and DMF (2.2 ml), and the mixture was stirred overnight at 50° C., and then stirred at 80° C. for 1 hr. The reaction mixture was poured into water, and extracted with ethyl acetate. The organic layer was washed with water and saturated brine, dried over anhydrous magnesium sulfate, and concentrated under reduced pressure. The residue was purified by silica gel column chromatography (hexane/ethyl acetate) to give the title compound (0.93 g).

MS: [M+H]$^+$ 356.9.

D) 2-{1-(cyclopropylmethyl)-3-[(3-methoxy-1-methyl-1H-pyrazol-4-yl)amino]-1H-indazol-6-yl}propan-2-ol A mixture of 2-[1-(cyclopropylmethyl)-3-iodo-1H-indazol-6-yl]propan-2-ol (200 mg), 3-methoxy-1-methyl-1H-pyrazol-4-amine hydrochloride (101 mg), NaO$^t$Bu (135 mg), BrettPhos Pd G3 (50.9 mg), BrettPhos (30.1 mg) and THF (3.6 ml) was stirred under microwave irradiation at 100° C. for 1 hr. The reaction mixture was filtered through a pad of basic silica gel, and the filtrate was concentrated under reduced pressure. The residue was purified by silica gel column chromatography (hexane/ethyl acetate), and the fraction was concentrated under reduced pressure. The obtained residue was crystallized from Et$_2$O/hexane to give the title compound (94 mg).

$^1$H NMR (400 MHz, DMSO-d$_6$) δ 0.33-0.49 (4H, m), 1.15-1.29 (1H, m), 1.47 (6H, s), 3.67 (3H, s), 3.85 (3H, s), 4.04 (2H, d, J=6.7 Hz), 5.02 (1H, s), 7.02 (1H, d, J=8.6 Hz), 7.43 (1H, s), 7.82 (1H, d, J=8.6 Hz), 7.85-7.88 (2H, m).

Example 50

2-{3-[(1,3-dimethyl-1H-pyrazol-4-yl)amino]-4-fluoro-1-methyl-1H-indazol-6-yl}propan-2-ol A mixture of 2-(4-fluoro-3-iodo-1-methyl-1H-indazol-6-yl)propan-2-ol (100 mg), 1,3-dimethyl-1H-pyrazol-4-amine (36.6 mg), NaO$^t$Bu (101 mg), BrettPhos Pd G3 (27.1 mg), BrettPhos (16.1 mg) and THF (1.5 ml) was stirred under microwave irradiation at 100° C. for 1 hr. The reaction mixture was purified by basic silica gel column chromatography (ethyl acetate/MeOH) and silica gel column chromatography (ethyl acetate/MeOH), and the fraction was concentrated under reduced pressure. The obtained residue was purified by HPLC to give the title compound (24 mg).

$^1$H NMR (400 MHz, DMSO-d$_6$) δ 1.47 (6H, s), 2.10 (3H, s), 3.73 (3H, s), 3.79 (3H, s), 5.16 (1H, s), 6.81 (1H, d, J=12.5 Hz), 7.11 (1H, s), 7.23 (1H, s), 7.76 (1H, s).

Example 51

2-{3-[(3-ethoxy-1-methyl-1H-pyrazol-4-yl)amino]-1-methyl-1H-indazol-6-yl}propan-2-ol A mixture of 2-(3-iodo-1-methyl-1H-indazol-6-yl)propan-2-ol (80.3 mg), 3-ethoxy-1-methyl-1H-pyrazol-4-amine (47.6 mg), NaO$^t$Bu (75.2 mg), BrettPhos Pd G3 (10.3 mg), BrettPhos (6.8 mg) and THF (2 ml) was stirred under microwave irradiation at 100° C. for 90 min. The reaction mixture was purified by basic silica gel column chromatography (hexane/ethyl acetate and ethyl acetate/MeOH) and silica gel column chromatography (hexane/ethyl acetate) to give the title compound (20.5 mg).

$^1$H NMR (300 MHz, DMSO-d$_6$) δ 1.33 (3H, t, J=7.0 Hz), 1.47 (6H, s), 3.66 (3H, s), 3.78 (3H, s), 4.20 (2H, q, J=6.9 Hz), 5.04 (1H, s), 7.03 (1H, dd, J=8.7, 1.5 Hz), 7.39 (1H, s), 7.75 (1H, s), 7.80-7.86 (2H, m).

Example 52, 53

2-{4-fluoro-1-methyl-3-[(4,5,6,7-tetrahydropyrazolo [1,5-a]pyridin-3-yl)amino]-1H-indazol-6-yl}propan-2-ol and 2-{4-fluoro-1-methyl-3-[(4,5,6,7-tetrahydropyrazolo[1,5-a]pyridin-3-yl)amino]-1H-indazol-6-yl}propan-2-ol hydrochloride A mixture of 2-(4-fluoro-3-iodo-1-methyl-1H-indazol-6-yl)propan-2-ol (60 mg), 4,5,6,7-tetrahydropyrazolo[1,5-a]pyridin-3-amine hydrochloride (34.3 mg), NaO$^t$Bu (43.1 mg), BrettPhos Pd G3 (16.3 mg), BrettPhos (9.6 mg) and THF (1 ml) was stirred under microwave irradiation at 100° C. for 1 hr. The reaction mixture was purified by basic silica gel column chromatography (ethyl acetate/MeOH), and the fraction was concentrated under reduced pressure. The obtained residue was crystallized from EtOH/heptane to give 2-{4-fluoro-1-methyl-3-[(4,5,6,7-tetrahydropyrazolo [1,5-a]pyridin-3-yl)amino]-1H-indazol-6-yl}propan-2-ol (28.5 mg).

$^1$H NMR (400 MHz, DMSO-d$_6$) δ 1.46 (6H, s), 1.70-1.82 (2H, m), 1.89-2.01 (2H, m), 2.64 (2H, t, J=6.3 Hz), 3.75 (3H, s), 4.02 (2H, t, J=6.0 Hz), 5.15 (1H, s), 6.79 (1H, d, J=12.5 Hz), 7.09 (1H, s), 7.21 (1H, s), 7.48 (1H, s).

To the mother liqure after crystallization was added a few drop of 4 mol/l hydrogen chloride ethyl acetate solution, and the resulting solid was collected by filtration, and dried under reduced pressure to give 2-{4-fluoro-1-methyl-3-[(4,5,6,7-tetrahydropyrazolo[1,5-a]pyridin-3-yl)amino]-1H-indazol-6-yl}propan-2-ol hydrochloride (6.2 mg).

$^1$H NMR (400 MHz, DMSO-d$_6$) δ 1.46 (6H, s), 1.71-1.82 (2H, m), 1.90-2.01 (2H, m), 2.66 (2H, t, J=6.2 Hz), 3.75 (3H, s), 4.00-4.07 (2H, m), 6.80 (1H, d, J=12.5 Hz), 6.99-7.44 (2H, m), 7.55 (1H, s).

Example 54

2-{3-[(6,7-dihydro-5H-pyrazolo[5,1-b][1,3]oxazin-3-yl)amino]-4-fluoro-1-methyl-1H-indazol-6-yl}propan-2-ol A mixture of 2-(4-fluoro-3-iodo-1-methyl-1H-indazol-6-yl)propan-2-ol (60 mg), 6,7-dihydro-5H-pyrazolo[5,1-b][1,3]oxazin-3-amine hydrochloride (34.7 mg), NaO$^t$Bu (43.1 mg), BrettPhos Pd G3 (16.3 mg), BrettPhos (9.6 mg) and THF (1 ml) was stirred under microwave irradiation at 100° C. for 1 hr. The reaction mixture was purified by basic silica gel column chromatography (ethyl acetate/MeOH), and the fraction was concentrated under reduced pressure. The obtained residue was crystallized from ethyl acetate/IPE/hexane to give the title compound (14.3 mg).

$^1$H NMR (400 MHz, DMSO-d$_6$) δ 1.46 (6H, s), 2.16 (2H, m), 3.72 (3H, s), 4.07 (2H, t, J=6.2 Hz), 4.21-4.28 (2H, m), 5.15 (1H, s), 6.69 (1H, s), 6.76 (1H, d, J=12.5 Hz), 7.19 (1H, s), 7.35 (1H, s).

Example 55

2-(5-fluoro-3-{[5-methoxy-1-(2-methylpropyl)-1H-pyrazol-4-yl]amino}-1-methyl-1H-indazol-6-yl)propan-2-ol A mixture of 2-(5-fluoro-3-iodo-1-methyl-1H-indazol-6-yl)propan-2-ol (60 mg), 5-methoxy-1-(2-methylpropyl)-1H-pyrazol-4-amine (33.4 mg), NaO$^t$Bu (43.1 mg), BrettPhos Pd G3 (16.3 mg), BrettPhos (9.6 mg) and THF (1.2 ml) was stirred under microwave irradiation at 100° C. for 1 hr. The reaction mixture was purified by silica gel column chromatography (hexane/ethyl acetate) and basic silica gel column chromatography (hexane/ethyl acetate) to give the title compound (26.3 mg).

$^1$H NMR (400 MHz, DMSO-d$_6$) δ 0.86 (6H, d, J=6.6 Hz), 1.51 (6H, s), 2.08 (1H, m), 3.70 (2H, d, J=7.2 Hz), 3.75 (3H, s), 3.90 (3H, s), 5.34 (1H, s), 7.27 (1H, d, J=12.5 Hz), 7.41 (1H, s), 7.48-7.55 (2H, m).

Example 56

2-{3-[(6,7-dihydro-5H-pyrazolo[5,1-b][1,3]oxazin-3-yl)amino]-5-fluoro-1-methyl-1H-indazol-6-yl}propan-2-ol A mixture of 2-(5-fluoro-3-iodo-1-methyl-1H-indazol-6-yl)propan-2-ol (60 mg), 6,7-dihydro-5H-pyrazolo[5,1-b][1,3]oxazin-3-amine hydrochloride (37.8 mg), NaO$^t$Bu (60.4 mg), BrettPhos Pd G3 (16.3 mg), BrettPhos (9.6 mg) and THF (1.2 ml) was stirred under microwave irradiation at 100° C. for 1 hr. The reaction mixture was purified by silica gel column chromatography (ethyl acetate/MeOH), and the fraction was concentrated under reduced pressure. The obtained residue was crystallized from THF/hexane to give the title compound (13.4 mg).

$^1$H NMR (400 MHz, DMSO-d$_6$) δ 1.51 (6H, s), 2.11-2.23 (2H, m), 3.73 (3H, s), 4.09 (2H, t, J=6.1 Hz), 4.27 (2H, t, J=5.0 Hz), 5.33 (1H, s), 7.36-7.45 (2H, m), 7.46-7.52 (2H, m).

Example 57

2-{3-[2-methoxy-3-(1-methyl-1H-pyrazol-4-yl)anilino]-1H-indazol-6-yl}propan-2-ol A) 2-methoxy-3-(1-methyl-1H-pyrazol-4-yl)aniline To a mixture of 3-bromo-2-methoxyaniline (3.03 g), 1-methyl-4-(4,4,5,5-tetramethyl-1,3,2-dioxaborolan-2-yl)-

1H-pyrazole (3.7 g), cesium carbonate (8.13 g), DME (60 ml) and water (20 ml) was added XPhos Pd G3 (0.114 g), and the mixture was stirred under nitrogen atmosphere at 100° C. for 2 hr. To the reaction mixture was added water, and the mixture was extracted with ethyl acetate. The organic layer was washed with water and saturated brine, dried over anhydrous sodium sulfate, and concentrated under reduced pressure. The residue was purified by basic silica gel column chromatography (hexane/ethyl acetate), and the fraction was concentrated under reduced pressure to give the title compound (2.47 g).

MS: [M+H]$^+$ 203.9.

B) methyl 3-[2-methoxy-3-(1-methyl-1H-pyrazol-4-yl)anilino]-1-(oxan-2-yl)-1H-indazole-6-carboxylate A mixture of methyl 3-iodo-1-(oxan-2-yl)-1H-indazole-6-carboxylate (300 mg), 2-methoxy-3-(1-methyl-1H-pyrazol-4-yl)aniline (174 mg), cesium carbonate (506 mg), Pd(OAc)$_2$ (17.4 mg), XANTPHOS (90 mg) and toluene (5 ml) was stirred overnight under nitrogen atmosphere at 80° C. The reaction mixture was purified by silica gel column chromatography (hexane/ethyl acetate) to give the title compound (358 mg).

MS: [M+H]$^+$ 462.1.

C) 2-{3-[2-methoxy-3-(1-methyl-1H-pyrazol-4-yl)anilino]-1-(oxan-2-yl)-1H-indazol-6-yl}propan-2-ol To a mixture of methyl 3-[2-methoxy-3-(1-methyl-1H-pyrazol-4-yl)anilino]-1-(oxan-2-yl)-1H-indazole-6-carboxylate (356 mg) and THF (7 ml) was added methylmagnesium bromide (1 mol/l THF solution) (4.6 ml) at 0° C., and the mixture was stirred under nitrogen atmosphere at 40° C. for 6 hr, and then stirred overnight at room temperature. To the reaction mixture was added saturated aqueous ammonium chloride solution at 0° C., and the mixture was extracted with ethyl acetate. The organic layer was washed with water and saturated brine, dried over anhydrous sodium sulfate, and filtered through a pad of silica gel, and the filtrate was concentrated under reduced pressure to give the title compound (298 mg).

MS: [M+H]$^+$ 462.2.

D) 2-{3-[2-methoxy-3-(1-methyl-1H-pyrazol-4-yl)anilino]-1H-indazol-6-yl}propan-2-ol To a mixture of 2-{3-[2-methoxy-3-(1-methyl-1H-pyrazol-4-yl)anilino]-1-(oxan-2-yl)-1H-indazol-6-yl}propan-2-ol (296 mg), EtOH (2 ml) and THF (3 ml) was added 6 mol/l hydrochloric acid (0.53 ml) at 0° C., and the mixture was stirred at room temperature for 3 hr, and then stirred at 50° C. for 25 min. To the reaction mixture was added saturated aqueous sodium hydrogencarbonate solution, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate), and the fraction was concentrated under reduced pressure. The obtained residue was crystallized from ethyl acetate/IPE to give the title compound (105 mg). 1H NMR (400 MHz, DMSO-d$_6$) δ 1.48 (6H, s), 3.67 (3H, s), 3.91 (3H, s), 5.08 (1H, s), 6.95-7.05 (2H, m), 7.12 (1H, d, J=8.7 Hz), 7.48 (1H, s), 7.71-7.79 (2H, m), 7.83 (1H, s), 7.89 (1H, s), 8.13 (1H, s), 12.07 (1H, s).

Example 58

2-{3-[(3-chloro-1-methyl-1H-pyrazol-4-yl)amino]-1-methyl-1H-indazol-5-yl}propan-2-ol A mixture of 2-(3-iodo-1-methyl-1H-indazol-5-yl)propan-2-ol (100 mg), 3-chloro-1-methyl-1H-pyrazol-4-amine (45.8 mg), NaO$^t$Bu (76 mg), BrettPhos Pd G3 (28.7 mg), BrettPhos (17 mg) and THF (1.8 ml) was stirred under microwave irradiation at 100° C. for 1 hr. The reaction mixture was purified by silica gel column chromatography (hexane/ethyl acetate), and the fraction was concentrated under reduced pressure. The obtained residue was crystallized from ethyl acetate/toluene/hexane to give the title compound (22.4 mg).

$^1$H NMR (400 MHz, DMSO-d$_6$) δ 1.48 (6H, s), 3.74-3.84 (6H, m), 4.96 (1H, s), 7.30 (1H, d, J=8.8 Hz), 7.50 (1H, d, J=9.3 Hz), 8.04-8.11 (2H, m), 8.15 (1H, s).

Example 59

2-[3-(cyclohexylamino)-1-methyl-1H-indazol-5-yl]propan-2-ol

A mixture of 2-(3-iodo-1-methyl-1H-indazol-5-yl)propan-2-ol (100 mg), cyclohexylamine (0.054 ml), CuI (6 mg), [(2,6-dimethylphenyl)amino](oxo)acetic acid (12.2 mg), tripotassium phosphate (134 mg) and DMSO (1.4 ml) was stirred overnight at 90° C. To the reaction mixture were added saturated aqueous ammonium chloride solution and ethyl acetate, and the mixture was stirred at room temperature for 30 min. The organic layer was washed with water and saturated brine, dried over anhydrous sodium sulfate, and concentrated under reduced pressure. The residue was purified by silica gel column chromatography (hexane/ethyl acetate) to give the title compound (79 mg).

$^1$H NMR (400 MHz, DMSO-d$_6$) δ 1.16-1.36 (6H, m), 1.46 (6H, s), 1.68-1.79 (2H, m), 2.00-2.10 (2H, m), 3.17 (1H, d, J=5.3 Hz), 3.68 (3H, s), 4.89 (1H, s), 5.73 (1H, d, J=7.7 Hz), 7.18 (1H, d, J=8.8 Hz), 7.39-7.45 (1H, m), 7.80 (1H, s).

Example 60

2-{3-[(6,6-difluoro-6,7-dihydro-5H-pyrazolo[5,1-b][1,3]oxazin-3-yl)amino]-1-methyl-1H-indazol-5-yl}propan-2-ol A mixture of 2-(3-iodo-1-methyl-1H-indazol-5-yl)propan-2-ol (60 mg), 6,6-difluoro-6,7-dihydro-5H-pyrazolo[5,1-b][1,3]oxazin-3-amine hydrochloride (40.2 mg), NaO$^t$Bu (63.8 mg), BrettPhos Pd G3 (17.2 mg), BrettPhos (10.2 mg) and THF (1.5 ml) was stirred under microwave irradiation at 100° C. for 1 hr. The reaction mixture was purified by silica gel column chromatography (hexane/ethyl acetate and ethyl acetate/MeOH), and the fraction was concentrated under reduced pressure. The obtained residue was crystallized from hexane to give the title compound (27.2 mg).

$^1$H NMR (400 MHz, DMSO-d$_6$) δ 1.46 (6H, s), 3.72 (3H, s), 4.55-4.73 (4H, m), 4.92 (1H, s), 7.25 (1H, d, J=8.8 Hz), 7.47 (1H, d, J=8.8 Hz), 7.70 (2H, d, J=13.4 Hz), 7.87 (1H, s).

Example 61

2-{1-(cyclopropylmethyl)-3-[(1,3-dimethyl-1H-pyrazol-4-yl)amino]-1H-indazol-5-yl}propan-2-ol

A) 2-[1-(cyclopropylmethyl)-3-iodo-1H-indazol-5-yl]propan-2-ol

To a mixture of 2-(3-iodo-1H-indazol-5-yl)propan-2-ol (5 g) and DMF (60 ml) was added cesium carbonate (8.09 g), and the mixture was stirred at 25° C. for 30 min. To the reaction mixture was added dropwise (bromomethyl)cyclopropane (6.7 g), and the mixture was stirred at 25° C. for 16 hr. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (petroleum ether/ethyl acetate) to give the title compound (2.14 g).
MS: [M+H]$^+$ 357.1.

B) 2-{1-(cyclopropylmethyl)-3-[(1,3-dimethyl-1H-pyrazol-4-yl)amino]-1H-indazol-5-yl}propan-2-ol A mixture of 2-[1-(cyclopropylmethyl)-3-iodo-1H-indazol-5-yl]propan-2-ol (100 mg), 1,3-dimethyl-1H-pyrazol-4-amine (37 mg), NaO$^t$Bu (5 mg), BrettPhos Pd G3 (18 mg), BrettPhos (11 mg) and 1,4-dioxane (1.5 ml) was stirred under microwave irradiation at 110° C. for 1 hr. The reaction mixture was filtered, and the filtrate was concentrated under reduced pressure. The obtained residue was purified by HPLC to give the title compound (25 mg).
$^1$H NMR (400 MHz, DMSO-d$_6$) δ 0.30-0.40 (2H, m), 0.41-0.50 (2H, m), 1.10-1.25 (1H, m), 1.48 (6H, s), 2.21 (3H, s), 3.73 (3H, s), 4.04 (2H, d, J=6.8 Hz), 4.98 (1H, brs), 7.33 (1H, d, J=8.8 Hz), 7.44 (1H, d, J=8.8 Hz), 7.88 (1H, s), 7.93 (1H, s), 8.04 (1H, s).

Example 62

2-(1-methyl-3-{[3-methyl-1-(propan-2-yl)-1H-pyrazol-4-yl]amino}-1H-indazol-5-yl)propan-2-ol

A) 3-methyl-4-nitro-1-(propan-2-yl)-1H-pyrazole and 5-methyl-4-nitro-1-(propan-2-yl)-1H-pyrazole A mixture of 3-methyl-4-nitro-1H-pyrazole (200 mg), potassium carbonate (326 mg) and DMF (8 ml) was stirred at 25° C. for 30 min, 2-iodopropane (802 mg) was added dropwise thereto, and the mixture was stirred at 25° C. for 4 hr. To the reaction mixture was added water, and the mixture was extracted with ethyl acetate. The organic layer was washed with water and saturated brine, dried over anhydrous sodium sulfate, and concentrated under reduced pressure to give a mixture (264 mg) of the title compounds.
MS: [M+H]$^+$ 170.0.

B) 3-methyl-1-(propan-2-yl)-1H-pyrazol-4-amine and 5-methyl-1-(propan-2-yl)-1H-pyrazol-4-amine A mixture of a mixture (264 mg) of 3-methyl-4-nitro-1-(propan-2-yl)-1H-pyrazole and 5-methyl-4-nitro-1-(propan-2-yl)-1H-pyrazole, 10% palladium on carbon (27 mg) and MeOH (5 ml) was stirred under hydrogen atmosphere at 25° C. for 8 hr. The insoluble substance was removed by filtration, to the filtrate was added water, and the mixture was extracted with ethyl acetate. The organic layer was washed with saturated brine, dried over anhydrous sodium sulfate, and concentrated under reduced pressure. The obtained residue was purified by silica gel column chromatography (petroleum ether/ethyl acetate) to give a mixture (150 mg) of the title compounds.
MS: [M+H]$^+$ 139.9.

C) 2-(1-methyl-3-{[3-methyl-1-(propan-2-yl)-1H-pyrazol-4-yl]amino}-1H-indazol-5-yl)propan-2-ol A mixture of 2-(3-iodo-1-methyl-1H-indazol-5-yl)propan-2-ol (189 mg), a mixture (100 mg) of 3-methyl-1-(propan-2-yl)-1H-pyrazol-4-amine and 5-methyl-1-(propan-2-yl)-1H-pyrazol-4-amine, NaO$^t$Bu (115 mg), BrettPhos Pd G3 (38 mg), BrettPhos (22 mg) and 1,4-dioxane (1.5 ml) was stirred under microwave irradiation at 110° C. for 1 hr. The reaction mixture was filtered, and the filtrate was concentrated under reduced pressure. The obtained residue was purified by HPLC to give the title compound (28 mg).
$^1$H NMR (400 MHz, DMSO-d$_6$) δ 1.37 (6H, d, J=6.8 Hz), 1.47 (6H, s), 2.19 (3H, s), 3.77 (3H, s), 4.25-4.42 (1H, m), 4.98 (1H, brs), 7.27 (1H, d, J=8.8 Hz), 7.45 (1H, dd, J=8.8, 1.6 Hz), 7.83 (1H, s), 7.94 (1H, s), 8.00 (1H, brs).

Example 63

2-(1-methyl-3-{[5-methyl-1-(propan-2-yl)-1H-pyrazol-4-yl]amino}-1H-indazol-5-yl)propan-2-ol A mixture of 2-(3-iodo-1-methyl-1H-indazol-5-yl)propan-2-ol (189 mg), a mixture (100 mg) of 3-methyl-1-(propan-2-yl)-1H-pyrazol-4-amine and 5-methyl-1-(propan-2-yl)-1H-pyrazol-4-amine, NaO$^t$Bu (115 mg), BrettPhos Pd G3 (38 mg), BrettPhos (22 mg) and 1,4-dioxane (1.5 ml) was stirred under microwave irradiation at 110° C. for 1 hr. The reaction mixture was filtered, and the filtrate was concentrated under reduced pressure. The obtained residue was purified by HPLC to give the title compound (15 mg).
$^1$H NMR (400 MHz, DMSO-d$_6$) δ 1.36 (6H, d, J=6.8 Hz), 1.46 (6H, s), 2.23 (3H, s), 3.73 (3H, s), 4.35-4.57 (1H, m), 4.97 (1H, brs), 7.26 (1H, d, J=8.8 Hz), 7.45 (1H, d, J=8.8 Hz), 7.56-7.65 (2H, m), 7.86 (1H, brs).

Example 64

2-{1-[(2,2-difluorocyclopropyl)methyl]-3-[(1,3-dimethyl-1H-pyrazol-4-yl)amino]-1H-indazol-5-yl}propan-2-ol

A) 2-{1-[(2,2-difluorocyclopropyl)methyl]-3-iodo-1H-indazol-5-yl}propan-2-ol To a mixture of 2-(3-iodo-1H-indazol-5-yl)propan-2-ol (3 g), cesium carbonate (4.85 g) and DMF (50 ml) was added 2-(bromomethyl)-1,1-difluorocyclopropane (2.55 g), and the mixture was stirred at 20° C. for 16 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give the title compound (1.4 g).
MS: [M+H]$^+$ 393.1.

B) 2-{1-[(2,2-difluorocyclopropyl)methyl]-3-[(1,3-dimethyl-1H-pyrazol-4-yl)amino]-1H-indazol-5-yl}propan-2-ol A mixture of 2-{1-[(2,2-difluorocyclopropyl)methyl]-3-iodo-1H-indazol-5-yl}propan-2-ol (95 mg), 1,3-dimethyl-1H-pyrazol-4-amine (32.3 mg), NaO$^t$Bu (46.6 mg), BrettPhos Pd G3 (15 mg), BrettPhos (9.1 mg) and 1,4-dioxane (2 ml) was stirred under microwave irradiation at 110° C. for 1 hr. The reaction mixture was filtered, and the filtrate was concentrated under reduced pressure. The obtained residue was purified by HPLC to give the title compound (43 mg).

$^1$H NMR (400 MHz, CDCl$_3$) δ 1.25-1.33 (1H, m), 1.46-1.55 (1H, m), 1.65 (6H, s), 1.80 (1H, s), 2.03-2.21 (1H, m), 2.31 (3H, s), 3.86 (3H, s), 4.23-4.40 (2H, m), 5.59 (1H, s), 7.24 (1H, d, J=8.8 Hz), 7.52 (1H, dd, J=8.8, 1.6 Hz), 7.66 (1H, s), 7.84 (1H, s).

Example 65

2-{1-cyclobutyl-3-[(1,3-dimethyl-1H-pyrazol-4-yl)amino]-1H-indazol-5-yl}propan-2-ol

A) 2-(1-cyclobutyl-3-iodo-1H-indazol-5-yl)propan-2-ol

To a mixture of 2-(3-iodo-1H-indazol-5-yl)propan-2-ol (5 g), cesium carbonate (8.09 g) and DMF (80 ml) was added bromocyclobutane (3.35 g), and the mixture was stirred at 55° C. for 16 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate), and washed with petroleum ether/ethyl acetate to give the title compound (2.25 g).

MS: [M+H]$^+$ 357.0.

B) 2-{1-cyclobutyl-3-[(1,3-dimethyl-1H-pyrazol-4-yl)amino]-1H-indazol-5-yl}propan-2-ol A mixture of 2-(1-cyclobutyl-3-iodo-1H-indazol-5-yl)propan-2-ol (63 mg), 1,3-dimethyl-1H-pyrazol-4-amine (24 mg), NaO$^t$Bu (34 mg), BrettPhos Pd G3 (11 mg), BrettPhos (6.7 mg) and 1,4-dioxane (2 ml) was stirred under microwave irradiation at 110° C. for 1 hr. The reaction mixture was filtered, and the filtrate was concentrated under reduced pressure. The obtained residue was purified by HPLC to give the title compound (21 mg).

$^1$H NMR (400 MHz, CDCl$_3$) δ 1.63 (6H, s), 1.72 (1H, br s), 1.81-2.03 (2H, m), 2.31 (3H, s), 2.39-2.57 (2H, m), 2.70-2.85 (2H, m), 3.87 (3H, s), 4.82-5.00 (1H, m), 5.62 (1H, br s), 7.27-7.33 (1H, m), 7.42-7.51 (1H, m), 7.59 (1H, s), 7.79-7.91 (1H, m)

Example 66

2-{3-[(1,3-dimethyl-1H-pyrazol-4-yl)amino]-1-(propan-2-yl)-1H-indazol-5-yl}propan-2-ol

A) 2-[3-iodo-1-(propan-2-yl)-1H-indazol-5-yl]propan-2-ol

To a mixture of 2-(3-iodo-1H-indazol-5-yl)propan-2-ol (10.1 g) and DMF (100 ml) was added potassium carbonate (6.96 g), and the mixture was stirred at 25° C. for 30 min. To the reaction mixture was added dropwise 2-iodopropane (17.1 g), and the mixture was stirred at 25° C. for 14 hr. To the reaction mixture were added again 2-iodopropane (4.83 g) and potassium carbonate (5.88 g), and the mixture was stirred at 25° C. for 4 hr. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (petroleum ether/ethyl acetate), and the fraction was concentrated under reduced pressure. The obtained residue was purified by HPLC to give the title compound (4.33 g).

MS: [M+H]$^+$ 345.1.

B) 2-{3-[(1,3-dimethyl-1H-pyrazol-4-yl)amino]-1-(propan-2-yl)-1H-indazol-5-yl}propan-2-ol A mixture of 2-[3-iodo-1-(propan-2-yl)-1H-indazol-5-yl]propan-2-ol (100 mg), 1,3-dimethyl-1H-pyrazol-4-amine (39 mg), NaO$^t$Bu (56 mg), BrettPhos Pd G3 (18 mg), BrettPhos (11 mg) and 1,4-dioxane (4 ml) was stirred under microwave irradiation at 110° C. for 1 hr. The reaction mixture was filtered, and the filtrate was concentrated under reduced pressure. The obtained residue was purified by HPLC to give the title compound (30 mg).

$^1$H NMR (400 MHz, DMSO-d$_6$) δ 1.41 (6H, d, J=6.8 Hz), 1.49 (6H, s), 2.22 (3H, s), 3.75 (3H, s), 4.65-4.75 (1H, m), 4.97 (1H, s), 7.33 (1H, d, J=8.8 Hz), 7.45 (1H, dd, J=8.8 Hz, 1.6 Hz), 7.89 (1H, s), 7.92 (1H, s), 8.03 (1H, d, J=0.8 Hz).

Example 67

2-{1-(cyclopropylmethyl)-3-[(3-methoxy-1-methyl-1H-pyrazol-4-yl)amino]-1H-indazol-5-yl}propan-2-ol A mixture of 2-[1-(cyclopropylmethyl)-3-iodo-1H-indazol-5-yl]propan-2-ol (80 mg), 3-methoxy-1-methyl-1H-pyrazol-4-amine hydrochloride (44 mg), NaO$^t$Bu (43 mg), BrettPhos Pd G3 (14 mg), BrettPhos (8.4 mg) and 1,4-dioxane (4 ml) was stirred under microwave irradiation at 110° C. for 2 hr. The reaction mixture was filtered, and the filtrate was concentrated under reduced pressure. The obtained residue was purified by HPLC to give the title compound (21 mg).

$^1$H NMR (400 MHz, DMSO-d$_6$) δ 0.28-0.46 (4H, m), 1.10-1.25 (1H, m), 1.47 (6H, s), 3.67 (3H, s), 3.85 (3H, s), 4.03 (2H, d, J=6.8 Hz), 4.91 (1H, s), 7.31 (1H, d, J=8.8 Hz), 7.40-7.50 (1H, m), 7.86 (1H, s), 7.97 (1H, s), 8.05 (1H, s).

Example 68

2-{1-cyclobutyl-3-[(3-methoxy-1-methyl-1H-pyrazol-4-yl)amino]-1H-indazol-6-yl}propan-2-ol

A) 2-(1-cyclobutyl-3-iodo-1H-indazol-6-yl)propan-2-ol

To a mixture of bromocyclobutane (6.7 g) and DMF (50 ml) were added cesium carbonate (16.2 g) and 2-(3-iodo-1H-indazol-6-yl)propan-2-ol (6 g) at 85° C., and the mixture was stirred at the same temperature for 16 hr. The reaction mixture was added to water, and the mixture was extracted with ethyl acetate. The organic layer was washed with water and saturated brine, dried over anhydrous sodium sulfate, and concentrated under reduced pressure. The residue was purified by silica gel column chromatography (petroleum ether/ethyl acetate) to give the title compound (3.3 g).

MS: [M+H]$^+$ 357.0.

B) 2-{1-cyclobutyl-3-[(3-methoxy-1-methyl-1H-pyrazol-4-yl)amino]-1H-indazol-6-yl}propan-2-ol A mixture of 2-(1-cyclobutyl-3-iodo-1H-indazol-6-yl) propan-2-ol (100 mg), 3-methoxy-1-methyl-1H-pyrazol-4-amine hydrochloride (55 mg), NaO$^t$Bu (54 mg), BrettPhos Pd G3 (18 mg), BrettPhos (11 mg) and 1,4-dioxane (4 ml) was stirred under microwave irradiation at 110° C. for 1 hr. To the reaction mixture was added water, and the mixture was extracted with ethyl acetate. The organic layer was washed with water and saturated brine, dried over anhydrous sodium sulfate, and concentrated under reduced pressure. The residue was purified by preparative TLC (silica gel, eluted with a mixture of petroleum ether/ethyl acetate) to give the title compound (15 mg).

$^1$H NMR (400 MHz, CDCl$_3$) δ 1.65 (6H, s), 1.75-2.00 (3H, m), 2.38-2.50 (2H, m), 2.70-2.85 (2H, m), 3.78 (3H, s), 4.00 (3H, s), 4.85-5.00 (1H, m), 5.71 (1H, brs), 7.06 (1H, d, J=8.4 Hz), 7.39-7.50 (2H, m), 7.80 (1H, s).

Example 69

2-{3-[2-methoxy-5-(1-methyl-1H-pyrazol-4-yl)anilino]-1H-indazol-6-yl}propan-2-ol A) 2-methoxy-5-(1-methyl-1H-pyrazol-4-yl)aniline To a mixture of 5-chloro-2-methoxyaniline (2 g), 1-methyl-4-(4,4,5,5-tetramethyl-1,3,2-dioxaborolan-2-yl)-1H-pyrazole (2.9 g), cesium carbonate (8.26 g), DME (40 ml) and water (15 ml) was added XPhos Pd G3 (0.2 g), and the mixture was stirred under nitrogen atmosphere at 100° C. for 2 hr. The aqueous layer of the reaction mixture was removed, basic silica gel was added thereto, and the mixture was concentrated under reduced pressure. The obtained residue was purified by basic silica gel column chromatography (ethyl acetate/MeOH), and the fraction was concentrated under reduced pressure. The obtained residue was crystallized from ethyl acetate/hexane to give the title compound (2.41 g).

MS: [M+H]$^+$ 203.9.

B) methyl 3-[2-methoxy-5-(1-methyl-1H-pyrazol-4-yl)anilino]-1-(oxan-2-yl)-1H-indazole-6-carboxylate A mixture of methyl 3-iodo-1-(oxan-2-yl)-1H-indazole-6-carboxylate (300 mg), 2-methoxy-5-(1-methyl-1H-pyrazol-4-yl)aniline (174 mg), cesium carbonate (506 mg), Pd(OAc)$_2$ (17.4 mg), XANTPHOS (90 mg) and toluene (5 ml) was stirred overnight under nitrogen atmosphere at 80° C. The reaction mixture was diluted with ethyl acetate, and filtered through a pad of basic silica gel, and the filtrate was concentrated under reduced pressure. The obtained residue was washed with a mixture of toluene and IPE, and dried under reduced pressure to give the title compound (106 mg).

MS: [M+H]$^+$ 462.2.

C) 2-{3-[2-methoxy-5-(1-methyl-1H-pyrazol-4-yl)anilino]-1H-indazol-6-yl}propan-2-ol To a mixture of methyl 3-[2-methoxy-5-(1-methyl-1H-pyrazol-4-yl)anilino]-1-(oxan-2-yl)-1H-indazole-6-car-boxylate (106 mg) and THF (2 ml) was added methylmagnesium bromide (1 mol/l THF solution) (1.38 ml) at 0° C., and the mixture was stirred under nitrogen atmosphere at 40° C. for 6 hr, and then stirred overnight at room temperature. To the reaction mixture was added saturated aqueous ammonium chloride solution at 0° C., and the mixture was extracted with ethyl acetate. The organic layer was washed with water and saturated brine, dried over anhydrous sodium sulfate, and filtered through a pad of silica gel, and the filtrate was concentrated under reduced pressure. To the obtained residue were added THF (2 ml) and EtOH (2 ml), 6 mol/l hydrochloric acid (0.53 ml) was added thereto at 0° C., and the mixture was stirred at 50° C. for 50 min. To the reaction mixture was added saturated aqueous sodium hydrogencarbonate solution, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate), and the fraction was concentrated under reduced pressure. The obtained residue was crystallized from ethyl acetate/IPE to give the title compound (8.8 mg).

$^1$H NMR (400 MHz, DMSO-d$_6$) δ 1.48 (6H, s), 3.85 (3H, s), 3.91 (3H, s), 5.08 (1H, s), 6.98 (2H, s), 7.12 (1H, d, J=8.4 Hz), 7.47 (1H, s), 7.55 (1H, s), 7.62 (1H, s), 7.77 (1H, d, J=8.6 Hz), 7.88 (1H, s), 8.24 (1H, s), 12.02 (1H, s).

Example 70

2-{1-cyclobutyl-3-[(3-methoxy-1-methyl-1H-pyrazol-4-yl)amino]-1H-indazol-5-yl}propan-2-ol A mixture of 2-(1-cyclobutyl-3-iodo-1H-indazol-5-yl) propan-2-ol (100 mg), 3-methoxy-1-methyl-1H-pyrazol-4-amine hydrochloride (55 mg), NaO$^t$Bu (54 mg), BrettPhos Pd G3 (18 mg), BrettPhos (11 mg) and 1,4-dioxane (2 ml) was stirred under microwave irradiation at 110° C. for 1 hr. The reaction mixture was filtered, and the filtrate was concentrated under reduced pressure. The obtained residue was purified by HPLC to give the title compound (29 mg).

$^1$H NMR (400 MHz, CDCl$_3$) δ 1.64 (6H, s), 1.77 (1H, br s), 1.83-1.99 (2H, m), 2.39-2.49 (2H, m), 2.73-2.86 (2H, m), 3.79 (3H, s), 4.02 (3H, s), 4.84-5.01 (1H, m), 5.80 (1H, s), 7.23-7.26 (1H, m), 7.49 (1H, d, J=8.8 Hz), 7.66 (1H, s), 7.85 (1H, s).

Example 71

2-{3-[(3-methoxy-1-methyl-1H-pyrazol-4-yl)amino]-1-(propan-2-yl)-1H-indazol-5-yl}propan-2-ol A mixture of 2-[3-iodo-1-(propan-2-yl)-1H-indazol-5-yl] propan-2-ol (80 mg), 3-methoxy-1-methyl-1H-pyrazol-4-amine hydrochloride (46 mg), NaO$^t$Bu (45 mg), BrettPhos Pd G3 (15 mg), BrettPhos (8.7 mg) and 1,4-dioxane (2 ml) was stirred under microwave irradiation at 110° C. for 2 hr. The reaction mixture was filtered, and the filtrate was concentrated under reduced pressure. The obtained residue was purified by HPLC to give the title compound (18 mg).

1H NMR (400 MHz, DMSO-d$_6$) δ 1.40 (6H, d, J=6.8 Hz), 1.48 (6H, s), 3.69 (3H, s), 3.87 (3H, s), 4.63-4.75 (1H, m), 4.90 (1H, s), 7.32 (1H, d, J=8.8 Hz), 7.47-7.49 (1H, dd, J=8.8 Hz, 1.6 Hz), 7.87 (1H, s), 8.00 (1H, s), 8.05 (1H, s).

Example 72

Optically Active 2-{1-[(2,2-difluorocyclopropyl) methyl]-3-[(3-methoxy-1-methyl-1H-pyrazol-4-yl) amino]-1H-indazol-5-yl}propan-2-ol (tR1)

A) racemic 2-{1-[(2,2-difluorocyclopropyl)methyl]-3-[(3-methoxy-1-methyl-1H-pyrazol-4-yl)amino]-1H-indazol-5-yl}propan-2-ol A mixture of 2-{1-[(2,2-difluorocyclopropyl)methyl]-3-iodo-1H-indazol-5-yl}propan-2-ol (100 mg), 3-methoxy-1-methyl-1H-pyrazol-4-amine hydrochloride (50 mg), NaO$^t$Bu (49 mg), BrettPhos Pd G3 (16 mg), BrettPhos (9.6 mg) and 1,4-dioxane (2 ml) was stirred under microwave irradiation at 110° C. for 1 hr. The reaction mixture was filtered, and the filtrate was concentrated under reduced pressure. To the reaction mixture was added water, and the mixture was extracted with ethyl acetate. The organic layer was washed with saturated brine, dried over anhydrous sodium sulfate, and concentrated under reduced pressure. The residue was purified by preparative TLC (silica gel, eluted with ethyl acetate) to give the title compound (60 mg).
MS: [M+H]$^+$ 392.1.

B) Optically Active 2-{1-[(2,2-difluorocyclopropyl) methyl]-3-[(3-methoxy-1-methyl-1H-pyrazol-4-yl) amino]-1H-indazol-5-yl}propan-2-ol (tR1)

Racemic 2-{1-[(2,2-difluorocyclopropyl)methyl]-3-[(3-methoxy-1-methyl-1H-pyrazol-4-yl)amino]-1H-indazol-5-yl}propan-2-ol (81 mg) was resolved by chiral SFC (Chiralpak AD-3, mobile phase: 2-propanol/carbon dioxide containing diethylamine), and the fraction with a shorter retention time was concentrated under reduced pressure to give the title compound (10 mg).
$^1$H NMR (400 MHz, CDCl$_3$) δ 1.25-1.30 (1H, m), 1.46-1.53 (1H, m), 1.66 (6H, s), 1.77 (1H, s), 2.07-2.22 (1H, m), 3.77 (3H, s), 4.02 (3H, s), 4.25-4.35 (2H, m), 5.79 (1H, s), 7.23 (1H, d, J=8.8 Hz), 7.53 (1H, dd, J=8.8, 1.6 Hz), 7.70 (1H, s), 7.82 (1H, s).

Example 73

2-(1-methyl-3-{[5-methyl-1-(2-methylpropyl)-1H-pyrazol-4-yl]amino}-1H-indazol-5-yl)propan-2-ol A) 3-methyl-1-(2-methylpropyl)-4-nitro-1H-pyrazole and 5-methyl-1-(2-methylpropyl)-4-nitro-1H-pyrazole To a mixture of 3-methyl-4-nitro-1H-pyrazole (200 mg) and DMF (5 ml) was added cesium carbonate (767 mg), and the mixture was stirred at 25° C. for 30 min. To the reaction mixture was added dropwise 1-iodo-2-methylpropane (867 mg), and the mixture was stirred at 25° C. for 4 hr. To the reaction mixture was added water, and the mixture was extracted with ethyl acetate. The organic layer was washed with water and saturated brine, dried over anhydrous sodium sulfate, and concentrated under reduced pressure to give a mixture (333 mg) of the title compounds.
MS: [M+H]$^+$ 183.9.

B) 3-methyl-1-(2-methylpropyl)-1H-pyrazol-4-amine and 5-methyl-1-(2-methylpropyl)-1H-pyrazol-4-amine A mixture of a mixture (253 mg) of 3-methyl-1-(2-methylpropyl)-1H-pyrazole and 5-methyl-1-(2-methylpropyl)-4-nitro-1H-pyrazole, 10% palladium on carbon (26 mg) and MeOH (5 ml) was stirred under hydrogen atmosphere at 25° C. for 8 hr. To the reaction mixture were added again 10% palladium on carbon (30 mg) and MeOH (3 ml), and the mixture was stirred under hydrogen atmosphere at 25° C. for 4 hr. The insoluble substance was removed by filtration, the filtrate was added to water, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give a mixture (163 mg) of the title compounds.
MS: [M+H]$^+$ 153.9.

C) 2-(1-methyl-3-{[5-methyl-1-(2-methylpropyl)-1H-pyrazol-4-yl]amino}-1H-indazol-5-yl)propan-2-ol A mixture of 2-(3-iodo-1-methyl-1H-indazol-5-yl)propan-2-ol (280 mg), a mixture (163 mg) of 3-methyl-1-(2-methylpropyl)-1H-pyrazol-4-amine and 5-methyl-1-(2-methylpropyl)-1H-pyrazol-4-amine, NaO$^t$Bu (170 mg), BrettPhos Pd G3 (56 mg), BrettPhos (33 mg) and 1,4-dioxane (1.5 ml) was stirred under microwave irradiation at 110° C. for 1 hr. The reaction mixture was filtered, and the filtrate was concentrated under reduced pressure. The obtained residue was purified by HPLC to give the title compound (8.3 mg).
$^1$H NMR (400 MHz, DMSO-d$_6$) δ 0.86 (6H, d, J=6.4 Hz), 1.46 (6H, s), 1.96-2.16 (1H, m), 2.23 (3H, s), 3.73 (3H, s), 3.81 (2H, d, J=7.2 Hz), 4.95 (1H, brs), 7.26 (1H, d, J=9.2 Hz), 7.38-7.51 (1H, m), 7.60-7.68 (2H, m), 7.89 (1H, brs).

Example 74

2-{3-[(1-cyclobutyl-3-methyl-1H-pyrazol-4-yl) amino]-1-methyl-1H-indazol-5-yl}propan-2-ol A) 1-cyclobutyl-3-methyl-4-nitro-1H-pyrazole and 1-cyclobutyl-5-methyl-4-nitro-1H-pyrazole To a mixture of 3-methyl-4-nitro-1H-pyrazole (1 g) and DMF (5 ml) was added cesium carbonate (3.85 g), and the mixture was stirred at 25° C. for 30 min. To the reaction mixture was added dropwise bromocyclobutane (3.19 g), and the mixture was stirred at 25° C. for 12 hr, and then stirred at 50° C. for 5 hr. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (petroleum ether/ethyl acetate) to give a mixture (1.11 g) of the title compounds.
MS: [M+H]$^+$ 182.0.

B) 1-cyclobutyl-3-methyl-1H-pyrazol-4-amine and 1-cyclobutyl-5-methyl-1H-pyrazol-4-amine A mixture of a mixture (1.11 g) of 1-cyclobutyl-3-methyl-4-nitro-1H-pyrazole and 1-cyclobutyl-5-methyl-4-nitro-1H-pyrazole, 10% palladium on carbon (120 mg), conc. hydrochloric acid (0.5 ml) and MeOH (15 ml) was stirred under hydrogen atmosphere at 25° C. for 13 hr. The insoluble substance was removed by filtration, and the filtrate was concentrated under reduced pressure to give a mixture (1.03 g) of the title compounds as a hydrochloride.
MS: [M+H]$^+$ 151.8.

C) 2-{3-[(1-cyclobutyl-3-methyl-1H-pyrazol-4-yl)amino]-1-methyl-1H-indazol-5-yl}propan-2-ol A mixture of 2-(3-iodo-1-methyl-1H-indazol-5-yl)propan-2-ol (702 mg), a hydrochloride (500 mg) of a mixture of 1-cyclobutyl-3-methyl-1H-pyrazol-4-amine and 1-cyclobutyl-5-methyl-1H-pyrazol-4-amine, NaO$^t$Bu (427 mg), BrettPhos Pd G3 (141 mg), BrettPhos (83.4 mg) and 1,4-dioxane (5 ml) was stirred under microwave irradiation at 110° C. for 1 hr. The reaction mixture was filtered, and the filtrate was concentrated under reduced pressure. The obtained residue was purified by HPLC to give the title compound (164 mg).

$^1$H NMR (400 MHz, DMSO-d$_6$) δ 1.48 (6H, s), 1.67-1.80 (2H, m), 2.22 (3H, s), 2.14-2.34 (2H, m), 2.36-2.46 (2H, m), 3.78 (3H, s,), 4.61-4.76 (1H, m), 5.00 (1H, s), 7.28 (1H, d, J=8.8 Hz) 7.46 (1H, dd, J=8.8, 1.6 Hz), 7.89 (1H, s), 7.98 (1H, s), 8.03 (1H, s).

Example 75

2-{3-[(1-cyclobutyl-5-methyl-1H-pyrazol-4-yl)amino]-1-methyl-1H-indazol-5-yl}propan-2-ol A mixture of 2-(3-iodo-1-methyl-1H-indazol-5-yl)propan-2-ol (702 mg), a hydrochloride (500 mg) of a mixture of 1-cyclobutyl-3-methyl-1H-pyrazol-4-amine and 1-cyclobutyl-5-methyl-1H-pyrazol-4-amine, NaO$^t$Bu (427 mg), BrettPhos Pd G3 (141 mg), BrettPhos (83.4 mg) and 1,4-dioxane (5 ml) was stirred under microwave irradiation at 110° C. for 1 hr. The reaction mixture was filtered, and the filtrate was concentrated under reduced pressure. The obtained residue was purified by HPLC to give the title compound (98 mg).

$^1$H NMR (400 MHz, DMSO-d$_6$) δ 1.46 (6H, s), 1.71-1.86 (2H, m), 2.20 (3H, s), 2.33 (2H, s), 2.54-2.63 (2H, m), 3.72 (3H, s), 4.69-4.86 (1H, m), 4.98 (1H, s), 7.26 (1H, d, J=8.8 Hz), 7.45 (1H, d, J=8.8 Hz), 7.60-7.71 (2H, m), 7.89 (1H, s).

Example 76

Optically Active 2-{1-[(2,2-difluorocyclopropyl)methyl]-3-[(1,3-dimethyl-1H-pyrazol-4-yl)amino]-1H-indazol-6-yl}propan-2-ol (tR1)

A) 2-{1-[(2,2-difluorocyclopropyl)methyl]-3-iodo-1H-indazol-6-yl}propan-2-ol To a mixture of 2-(3-iodo-1H-indazol-6-yl)propan-2-ol (4 g) and DMF (40 ml) were added cesium carbonate (6.47 g) and 2-(bromomethyl)-1,1-difluorocyclopropane (3.4 g), and the mixture was stirred at 10° C. for 16 hr. The reaction mixture was added to water, and the mixture was extracted with ethyl acetate. The organic layer was washed with water and saturated brine, dried over anhydrous sodium sulfate, and concentrated under reduced pressure. The residue was purified by silica gel column chromatography (petroleum ether/ethyl acetate) to give the title compound (3.6 g).

MS: [M+H]$^+$ 393.0.

B) racemic 2-{1-[(2,2-difluorocyclopropyl)methyl]-3-[(1,3-dimethyl-1H-pyrazol-4-yl)amino]-1H-indazol-6-yl}propan-2-ol A mixture of 2-{1-[(2,2-difluorocyclopropyl)methyl]-3-iodo-1H-indazol-6-yl}propan-2-ol (200 mg), 1,3-dimethyl-1H-pyrazol-4-amine (68 mg), NaO$^t$Bu (98 mg), BrettPhos Pd G3 (32 mg), BrettPhos (19 mg) and 1,4-dioxane (5 ml) was stirred under microwave irradiation at 110° C. for 1 hr. The reaction mixture was filtered, and the filtrate was concentrated under reduced pressure. The residue was purified by silica gel column chromatography (petroleum ether/ethyl acetate) to give the title compound (51 mg).

MS: [M+H]$^+$ 376.1.

C) Optically Active 2-{1-[(2,2-difluorocyclopropyl)methyl]-3-[(1,3-dimethyl-1H-pyrazol-4-yl)amino]-1H-indazol-6-yl}propan-2-ol (tR1)

Racemic 2-{1-[(2,2-difluorocyclopropyl)methyl]-3-[(1,3-dimethyl-1H-pyrazol-4-yl)amino]-1H-indazol-6-yl}propan-2-ol (66 mg) was resolved by chiral SFC (Chiralpak AD-3, mobile phase: 2-propanol/carbon dioxide containing diethylamine), and the fraction with a shorter retention time was concentrated under reduced pressure to give the title compound (31.5 mg).

$^1$H NMR (400 MHz, CDCl$_3$) δ 1.22-1.35 (1H, m), 1.45-1.55 (1H, m), 1.67 (6H, s), 1.87 (1H, brs), 2.12-2.25 (1H, m), 2.29 (3H, s), 3.87 (3H, s), 4.25-4.40 (2H, m), 5.56 (1H, brs), 7.12 (1H, dd, J=8.8, 1.6 Hz), 7.40 (1H, d, J=8.8 Hz), 7.46 (1H, s), 7.76 (1H, s).

Example 77

Optically Active 2-{1-[(2,2-difluorocyclopropyl)methyl]-3-[(3-methoxy-1-methyl-1H-pyrazol-4-yl)amino]-1H-indazol-6-yl}propan-2-ol (tR1)

A) racemic 2-{1-[(2,2-difluorocyclopropyl)methyl]-3-[(3-methoxy-1-methyl-1H-pyrazol-4-yl)amino]-1H-indazol-6-yl}propan-2-ol A mixture of 2-{1-[(2,2-difluorocyclopropyl)methyl]-3-iodo-1H-indazol-6-yl}propan-2-ol (300 mg), 3-methoxy-1-methyl-1H-pyrazol-4-amine hydrochloride (150 mg), NaO$^t$Bu (147 mg), BrettPhos Pd G3 (48 mg), BrettPhos (29 mg) and 1,4-dioxane (4 ml) was stirred under microwave irradiation at 110° C. for 1 hr. To the reaction mixture were added again NaO$^t$Bu (147 mg), BrettPhos Pd G3 (48 mg) and BrettPhos (29 mg), and the mixture was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give the title compound (139 mg).

MS: [M+H]$^+$ 392.1.

B) Optically Active 2-{1-[(2,2-difluorocyclopropyl)methyl]-3-[(3-methoxy-1-methyl-1H-pyrazol-4-yl)amino]-1H-indazol-6-yl}propan-2-ol (tR1)

Racemic 2-{1-[(2,2-difluorocyclopropyl)methyl]-3-[(3-methoxy-1-methyl-1H-pyrazol-4-yl)amino]-1H-indazol-6-yl}propan-2-ol (139 mg) was resolved by chiral SFC (Chiralpak IC-3, mobile phase: 2-propanol/carbon dioxide containing diethylamine), and the fraction with a shorter retention time was concentrated under reduced pressure to give the title compound (33 mg).

$^1$H NMR (400 MHz, DMSO-d$_6$) δ 1.43-1.50 (7H, m), 1.60-1.71 (1H, m), 2.11-2.23 (1H, m), 3.67 (3H, s), 3.85

(3H, s), 4.18-4.25 (1H, m), 4.27-4.35 (1H, m), 5.06 (1H, s), 7.07 (1H, d, J=8.8 Hz), 7.45 (1H, s), 7.87 (1H, d, J=8.8 Hz), 7.91 (1H, s), 8.03 (1H, s).

Example 78

2-{1-cyclobutyl-3-[(1,3-dimethyl-1H-pyrazol-4-yl)amino]-1H-indazol-6-yl}propan-2-ol A mixture of 2-(1-cyclobutyl-3-iodo-1H-indazol-6-yl)propan-2-ol (100 mg), 1,3-dimethyl-1H-pyrazol-4-amine (37 mg), NaO$^t$Bu (54 mg), BrettPhos Pd G3 (18 mg), BrettPhos (11 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by preparative TLC (silica gel, eluted with ethyl acetate) to give the title compound (19 mg).
$^1$H NMR (400 MHz, CDCl$_3$) δ 1.64 (6H, s), 1.78-2.00 (3H, m), 2.27 (3H, s), 2.37-2.50 (2H, m), 2.67-2.88 (2H, m), 3.85 (3H, s), 4.87-5.02 (1H, m), 5.58 (1H, brs), 7.02 (1H, d, J=8.4 Hz), 7.30 (1H, d, J=8.8 Hz), 7.46 (1H, s), 7.71 (1H, s).

Example 79

Optically Active 2-{1-[(2,2-difluorocyclopropyl)methyl]-3-[(3-methoxy-1-methyl-1H-pyrazol-4-yl)amino]-1H-indazol-5-yl}propan-2-ol (tR2)

Racemic 2-{1-[(2,2-difluorocyclopropyl)methyl]-3-[(3-methoxy-1-methyl-1H-pyrazol-4-yl)amino]-1H-indazol-5-yl}propan-2-ol (81 mg) was resolved by chiral SFC (Chiralpak AD-3, mobile phase: 2-propanol/carbon dioxide containing diethylamine), and the fraction with a longer retention time was concentrated under reduced pressure to give the title compound (13 mg).
$^1$H NMR (400 MHz, CDCl$_3$) δ 1.26-1.30 (1H, m), 1.47-1.53 (1H, m), 1.66 (6H, s), 1.77 (1H, s), 2.04-2.22 (1H, m), 3.77 (3H, s), 4.02 (3H, s), 4.25-4.37 (2H, m), 5.78 (1H, s), 7.23 (1H, d, J=8.8 Hz), 7.53 (1H, dd, J=8.8, 1.2 Hz), 7.70 (1H, s), 7.82 (1H, s).

Example 80

Optically Active 2-{1-[(2,2-difluorocyclopropyl)methyl]-3-[(1,3-dimethyl-1H-pyrazol-4-yl)amino]-1H-indazol-6-yl}propan-2-ol (tR2)

Racemic 2-{1-[(2,2-difluorocyclopropyl)methyl]-3-[(1,3-dimethyl-1H-pyrazol-4-yl)amino]-1H-indazol-6-yl}propan-2-ol (66 mg) was resolved by chiral SFC (Chiralpak AD-3, mobile phase: 2-propanol/carbon dioxide containing diethylamine), and the fraction with a longer retention time was concentrated under reduced pressure to give the title compound (31.4 mg).
$^1$H NMR (400 MHz, CDCl$_3$) δ 1.22-1.35 (1H, m), 1.45-1.55 (1H, m), 1.67 (6H, s), 1.80-1.95 (1H, m), 2.12-2.23 (1H, m), 2.29 (3H, s), 3.87 (3H, s), 4.25-4.40 (2H, m), 5.56 (1H, brs), 7.12 (1H, dd, J=8.4, 1.2 Hz), 7.40 (1H, d, J=8.4 Hz), 7.46 (1H, s), 7.76 (1H, s).

Example 81

Optically Active 2-{1-[(2,2-difluorocyclopropyl)methyl]-3-[(3-methoxy-1-methyl-1H-pyrazol-4-yl)amino]-1H-indazol-6-yl}propan-2-ol (tR2)

Racemic 2-{1-[(2,2-difluorocyclopropyl)methyl]-3-[(3-methoxy-1-methyl-1H-pyrazol-4-yl)amino]-1H-indazol-6-yl}propan-2-ol (139 mg) was resolved by chiral SFC (Chiralpak IC-3, mobile phase: 2-propanol/carbon dioxide containing diethylamine), and the fraction with a longer retention time was concentrated under reduced pressure to give the title compound (36 mg).
$^1$H NMR (400 MHz, DMSO-d$_6$) δ 1.43-1.50 (7H, m), 1.60-1.71 (1H, m), 2.11-2.23 (1H, m), 3.67 (3H, s), 3.85 (3H, s), 4.16-4.25 (1H, m), 4.26-4.35 (1H, m), 5.06 (1H, s), 7.07 (1H, d, J=8.4 Hz), 7.45 (1H, s), 7.87 (1H, d, J=8.4 Hz), 7.91 (1H, s), 8.03 (1H, s).

Example 82

2-(1-cyclobutyl-3-{[3-(methoxymethyl)-1-methyl-1H-pyrazol-4-yl]amino}-1H-indazol-6-yl)propan-2-ol A) methyl 1-methyl-4-nitro-1H-pyrazole-3-carboxylate To a mixture of 1-methyl-4-nitro-1H-pyrazole-3-carboxylic acid (5 g) and MeOH (150 ml) was added conc. sulfuric acid (1.5 ml), and the mixture was stirred at 85° C. for 5 hr. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give the title compound (5.11 g).
$^1$H NMR (400 MHz, CDCl$_3$) δ 3.98 (3H, s), 4.01 (3H, s), 8.16 (1H, s).

B) (1-methyl-4-nitro-1H-pyrazol-3-yl)methanol

To a mixture of methyl 1-methyl-4-nitro-1H-pyrazole-3-carboxylate (5.11 g) and THF (50 ml) was added a solution of diisobutylaluminium hydride in toluene (55.2 ml, 1 mol/l) at −20° C., and the mixture was stirred under nitrogen atmosphere for 30 min. The reaction mixture was added to saturated aqueous citric acid solution, and the mixture was extracted with ethyl acetate. The organic layer was washed with saturated brine, and concentrated under reduced pressure. The residue was purified by silica gel column chromatography (ethyl acetate), and the fraction was concentrated under reduced pressure. To the obtained residue was added ethyl acetate, and the insoluble substance was removed by filtration. The filtrate was washed with saturated aqueous potassium sodium tartrate solution, and the organic layer was concentrated under reduced pressure to give the title compound (1.66 g).
$^1$H NMR (400 MHz, DMSO-d$_6$) δ 3.87 (3H, s), 4.75 (2H, d, J=5.6 Hz), 5.21 (1H, t, J=5.6 Hz), 8.79 (1H, s).

C) 3-(methoxymethyl)-1-methyl-4-nitro-1H-pyrazole

To a mixture of (1-methyl-4-nitro-1H-pyrazol-3-yl)methanol (1.16 g) and THF (10 ml) was added 60% sodium hydride (348 mg) at 0° C., and the mixture was stirred for 30 min. To the reaction mixture was added dimethylsulfuric acid (1.12 g), and the mixture was stirred at 50° C. for 5 hr. The reaction mixture was diluted with water (30 ml), and added to 5% ammonium aqueous solution (50 ml), and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give the title compound.
MS: [M+H]$^+$ 171.7.

D)
3-(methoxymethyl)-1-methyl-1H-pyrazol-4-amine

A mixture of 3-(methoxymethyl)-1-methyl-4-nitro-1H-pyrazole (1.39 g), 10% palladium on carbon (139 mg) and MeOH (14 ml) was stirred under hydrogen atmosphere at 25° C. for 14 hr. The insoluble substance was removed by filtration, and the filtrate was concentrated under reduced pressure to give a mixture (1.11 g) containing the title compound.
$^1$H NMR (400 MHz, DMSO-d$_6$) δ 3.04 (2H, brs), 3.34 (3H, s), 3.72 (3H, s), 4.45 (2H, s), 6.90 (1H, s).

E) 2-(1-cyclobutyl-3-{[3-(methoxymethyl)-1-methyl-1H-pyrazol-4-yl]amino}-1H-indazol-6-yl)propan-2-ol A mixture of 2-(1-cyclobutyl-3-iodo-1H-indazol-6-yl)propan-2-ol (100 mg), 3-(methoxymethyl)-1-methyl-1H-pyrazol-4-amine (48 mg), NaO$^t$Bu (54 mg), BrettPhos Pd G3 (18 mg), BrettPhos (11 mg) and 1,4-dioxane (3 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by preparative TLC (silica gel, eluted with a mixture of petroleum ether/ethyl acetate) to give the title compound (41 mg).
$^1$H NMR (400 MHz, DMSO-d$_6$) δ 1.47 (6H, s), 1.77-1.88 (2H, m), 2.29-2.38 (2H, m), 2.60-2.69 (2H, m), 3.24 (3H, s), 3.82 (3H, s), 4.50 (2H, s), 5.01-5.10 (2H, m), 7.09 (1H, d, J=9.6 Hz), 7.49 (1H, s), 7.81 (1H, d, J=8.4 Hz), 7.98 (1H, s), 8.06 (1H, s).

Example 83

2-(1-[(2,2-difluorocyclopropyl)methyl]-3-{[3-(methoxymethyl)-1-methyl-1H-pyrazol-4-yl]amino}-1H-indazol-6-yl)propan-2-ol A mixture of 2-{1-[(2,2-difluorocyclopropyl)methyl]-3-iodo-1H-indazol-6-yl}propan-2-ol (100 mg), 3-(methoxymethyl)-1-methyl-1H-pyrazol-4-amine (43 mg), NaO$^t$Bu (49 mg), BrettPhos Pd G3 (16 mg), BrettPhos (10 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) and preparative TLC (silica gel, eluted with a mixture of petroleum ether/ethyl acetate) to give the title compound (33 mg).
$^1$H NMR (400 MHz, DMSO-d$_6$) δ 1.41-1.51 (7H, m), 1.59-1.72 (1H, m), 2.14-2.26 (1H, m), 3.25 (3H, s), 3.79 (3H, s), 4.19-4.29 (1H, m), 4.30-4.39 (1H, m), 4.50 (2H, s), 5.08 (1H, s), 7.14 (1H, d, J=8.8 Hz), 7.49 (1H, s), 7.87 (1H, d, J=8.8 Hz), 8.00-8.12 (2H, m).

Example 84

2-[1-(cyclopropylmethyl)-3-{[3-(methoxymethyl)-1-methyl-1H-pyrazol-4-yl]amino}-1H-indazol-6-yl]propan-2-ol A mixture of 2-[1-(cyclopropylmethyl)-3-iodo-1H-indazol-6-yl]propan-2-ol (100 mg), 3-(methoxymethyl)-1-methyl-1H-pyrazol-4-amine (48 mg), NaO$^t$Bu (54 mg), BrettPhos Pd G3 (18 mg), BrettPhos (11 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by preparative TLC (silica gel, eluted with a mixture of petroleum ether/ethyl acetate) to give the title compound (40 mg).
$^1$H NMR (400 MHz, DMSO-d$_6$) δ 0.34-0.50 (4H, m), 1.19-1.28 (1H, m), 1.48 (6H, s), 3.24 (3H, s), 3.80 (3H, s), 4.07 (2H, d, J=6.8 Hz), 4.50 (2H, s), 5.07 (1H, s), 7.09 (1H, dd, J=8.8, 1.2 Hz), 7.46 (1H, s), 7.83 (1H, d, J=8.4 Hz), 7.92 (1H, s), 8.03 (1H, s).

Example 85

2-[3-{[3-(methoxymethyl)-1-methyl-1H-pyrazol-4-yl]amino}-1-(propan-2-yl)-1H-indazol-6-yl]propan-2-ol A) 2-[3-iodo-1-(propan-2-yl)-1H-indazol-6-yl]propan-2-ol To a mixture of 2-(3-iodo-1H-indazol-6-yl)propan-2-ol (500 mg), 2-iodopropane (422 mg) and DMF (5 ml) was added cesium carbonate (809 mg), and the mixture was stirred at 10 to 15° C. for 16 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give the title compound (287 mg).
MS: [M+H]$^+$ 344.9.

B) 2-[3-{[3-(methoxymethyl)-1-methyl-1H-pyrazol-4-yl]amino}-1-(propan-2-yl)-1H-indazol-6-yl]propan-2-ol A mixture of 2-[3-iodo-1-(propan-2-yl)-1H-indazol-6-yl]propan-2-ol (100 mg), 3-(methoxymethyl)-1-methyl-1H-pyrazol-4-amine (49 mg), NaO$^t$Bu (56 mg), BrettPhos Pd G3 (18 mg), BrettPhos (11 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by preparative TLC (silica gel, eluted with a mixture of petroleum ether/ethyl acetate) to give the title compound (65 mg).

¹H NMR (400 MHz, DMSO-d₆) δ 1.43 (6H, d, J=6.4 Hz), 1.48 (6H, s), 3.24 (3H, s), 3.81 (3H, s), 4.50 (2H, s), 4.70-4.81 (1H, m), 5.07 (1H, s), 7.07 (1H, d, J=8.4 Hz), 7.47 (1H, s), 7.81 (1H, d, J=8.4 Hz) 7.93 (1H, s), 8.01 (1H, s).

Example 86

2-[3-{[3-(methoxymethyl)-1-methyl-1H-pyrazol-4-yl]amino}-1-(propan-2-yl)-1H-indazol-5-yl]propan-2-ol A mixture of 2-[3-iodo-1-(propan-2-yl)-1H-indazol-5-yl]propan-2-ol (100 mg), 3-(methoxymethyl)-1-methyl-1H-pyrazol-4-amine (49 mg), NaO$^t$Bu (56 mg), BrettPhos Pd G3 (18 mg), BrettPhos (11 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by HPLC to give the title compound (42 mg).

¹H NMR (400 MHz, DMSO-d₆) δ 1.42 (6H, d, J=6.8 Hz), 1.49 (6H, s), 3.24 (3H, s), 3.81 (3H, s), 4.53 (2H, s), 4.67-4.80 (1H, m), 5.00 (1H, s), 7.34 (1H, d, J=8.8 Hz), 7.44 (1H, dd, J=8.8, 1.6 Hz), 7.98-8.09 (3H, m).

Example 87

2-[1-(cyclopropylmethyl)-3-{[3-(methoxymethyl)-1-methyl-1H-pyrazol-4-yl]amino}-1H-indazol-5-yl]propan-2-ol A mixture of 2-[1-(cyclopropylmethyl)-3-iodo-1H-indazol-5-yl]propan-2-ol (100 mg), 3-(methoxymethyl)-1-methyl-1H-pyrazol-4-amine (48 mg), NaO$^t$Bu (54 mg), BrettPhos Pd G3 (18 mg), BrettPhos (11 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by preparative TLC (silica gel, eluted with ethyl acetate) to give the title compound (42 mg).

¹H NMR (400 MHz, DMSO-d₆) δ 0.33-0.39 (2H, m), 0.41-0.48 (2H, m), 1.19-1.25 (1H, m), 1.49 (6H, s), 3.24 (3H, s), 3.80 (3H, s), 4.06 (2H, d, J=6.8 Hz), 4.52 (2H, s), 5.01 (1H, s), 7.35 (1H, d, J=9.2 Hz), 7.42-7.47 (1H, m), 7.98-8.09 (3H, m).

Example 88

2-(1-cyclobutyl-3-{[3-(methoxymethyl)-1-methyl-1H-pyrazol-4-yl]amino}-1H-indazol-5-yl)propan-2-ol A mixture of 2-(1-cyclobutyl-3-iodo-1H-indazol-5-yl)propan-2-ol (100 mg), 3-(methoxymethyl)-1-methyl-1H-pyrazol-4-amine (48 mg), NaO$^t$Bu (54 mg), BrettPhos Pd G3 (18 mg), BrettPhos (11 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by preparative TLC (silica gel, eluted with ethyl acetate) to give the title compound (49 mg).

¹H NMR (400 MHz, DMSO-d₆) δ 1.48 (6H, s), 1.71-1.91 (2H, m), 2.27-2.41 (2H, m), 2.55-2.71 (2H, m), 3.24 (3H, s), 3.83 (3H, s), 4.54 (2H, s), 4.93-5.10 (2H, m), 7.35 (1H, d, J=8.8 Hz), 7.44 (1H, dd, J=8.8, 1.2 Hz), 8.02-8.14 (3H, m).

Example 89

2-(1-[(2,2-difluorocyclopropyl)methyl]-3-{[3-(methoxymethyl)-1-methyl-1H-pyrazol-4-yl]amino}-1H-indazol-5-yl)propan-2-ol A mixture of 2-{1-[(2,2-difluorocyclopropyl)methyl]-3-iodo-1H-indazol-5-yl}propan-2-ol (100 mg), 3-(methoxymethyl)-1-methyl-1H-pyrazol-4-amine (43 mg), NaO$^t$Bu (49 mg), BrettPhos Pd G3 (16 mg), BrettPhos (10 mg) and 1,4-dioxane (2 ml) was stirred under microwave irradiation at 110° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by HPLC to give the title compound (53 mg).

¹H NMR (400 MHz, DMSO-d₆) δ 1.46-1.52 (7H, s), 1.59-1.69 (1H, m), 2.10-2.25 (1H, m), 3.24 (3H, s), 3.79 (3H, s), 4.19-4.28 (1H, m), 4.29-4.40 (1H, m), 4.53 (2H, s), 5.02 (1H, s), 7.36 (1H, d, J=8.8 Hz), 7.48 (1H, dd, J=8.8, 1.6 Hz), 8.06-8.09 (3H, m).

The compounds of Examples are shown in the following tables. MS in the tables means actual measured value. The compounds of Examples 1 to 89 in the following tables were produced according to the methods described in the above-mentioned Examples, or methods analogous thereto.

TABLE 1-1

| Ex. No. | IUPAC Name | Structure | Additive | MS |
|---|---|---|---|---|
| 1 | 2-{3-[2-methoxy-5-(trifluoromethyl)anilino]-1H-indazol-6-yl}propan-2-ol | 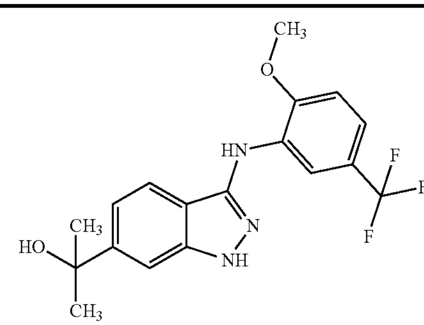 | | 366.1 |

TABLE 1-1-continued

| Ex. No. | IUPAC Name | Structure | Additive | MS |
|---|---|---|---|---|
| 2 | 2-{3-[(2, 3-dihydro-1-benzofuran-7-yl)amino]-1-methyl-1H-indazol-6-yl}propan-2-ol | 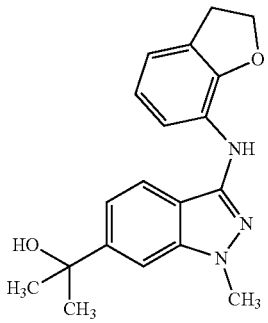 [SMILES: Cn1nc(Nc2cccc3c2OCC3)c2ccc(C(C)(C)O)cc21] | | 324.2 |
| 3 | 2-(3-{[1-(difluoromethyl)-5-methyl-1H-pyrazol-4-yl]amino}-1-methyl-1H-indazol-6-yl)propan-2-ol | 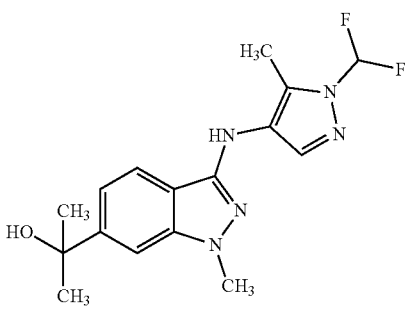 [SMILES: Cc1c(Nc2nn(C)c3cc(C(C)(C)O)ccc23)cnn1C(F)F] | | 336.2 |
| 4 | 2-{3-[(1,4-dimethyl-1H-pyrazol-3-yl)amino]-1-methyl-1H-indazol-6-yl}propan-2-ol | 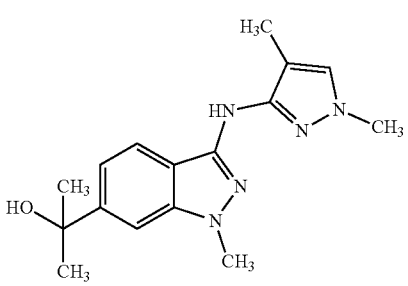 [SMILES: Cc1cn(C)nc1Nc1nn(C)c2cc(C(C)(C)O)ccc12] | | 300.3 |
| 5 | 2-(1-methyl-3-{[1-methyl-3-(trifluoromethyl)-1H-pyrazol-4-yl]amino}-1H-indazol-6-yl)propan-2-ol | 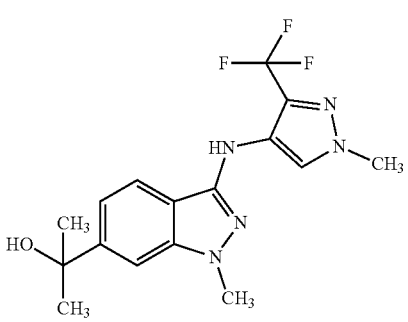 [SMILES: Cn1cc(Nc2nn(C)c3cc(C(C)(C)O)ccc23)c(C(F)(F)F)n1] | | 354.2 |

TABLE 1-2

| 6 | 2-{3-[(5-chloro-1-methyl-1H-pyrazol-4-yl)amino]-1-methyl-1H-indazol-6-yl}propan-2-ol | 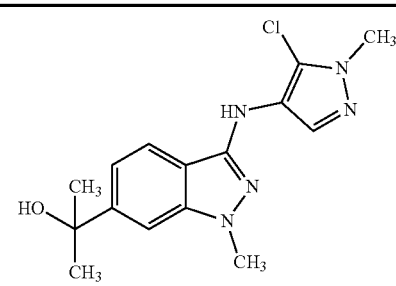 | | 320.2 |

TABLE 1-2-continued
| 7 | 2-{3-[(3-chloro-1-methyl-1H-pyrazol-4-yl)amino]-1-methyl-1H-indazol-6-yl}propan-2-ol | 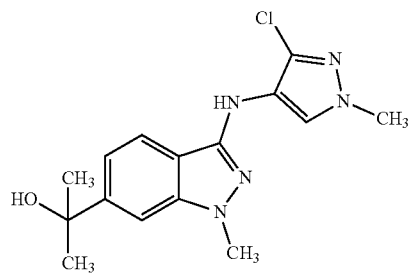 [SMILES: Cn1cc(Nc2nn(C)c3cc(C(C)(C)O)ccc23)c(Cl)n1] | 320.1 |
| 8 | 2-{3-[(1,5-dimethyl-1H-pyrazol-4-yl) amino]-1-methyl-1H-indazol-6-yl}propan-2-ol | 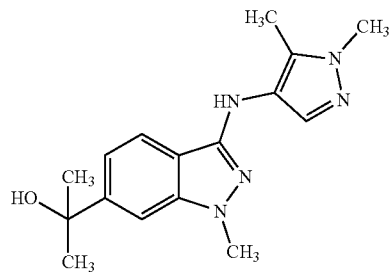 [SMILES: Cc1c(Nc2nn(C)c3cc(C(C)(C)O)ccc23)cnn1C] | 300.3 |
| 9 | 2-(1-methyl-3-{[1-methyl-5-(trifluoromethyl)-1H-pyrazol-4-yl]amino}-1H-indazol-6-yl)propan-2-ol | 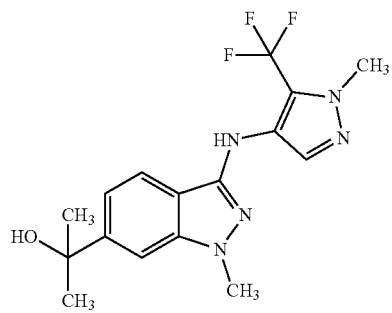 [SMILES: Cn1ncc(Nc2nn(C)c3cc(C(C)(C)O)ccc23)c1C(F)(F)F] | 354.1 |
| 10 | 2-{3-[(3-methoxy-1-methyl-1H-pyrazol-4-yl)amino]-1-methyl-1H-indazol-6-yl}propan-2-ol | 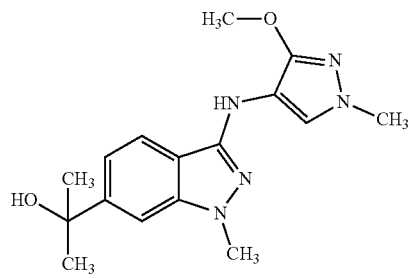 [SMILES: COc1nn(C)cc1Nc1nn(C)c2cc(C(C)(C)O)ccc12] | 316.3 |
TABLE 1-3
| 11 | 2-{3-[(1,3-dimethyl-1H-pyrazol-5-yl)amino]-1-methyl-1H-indazol-6-yl}propan-2-ol | 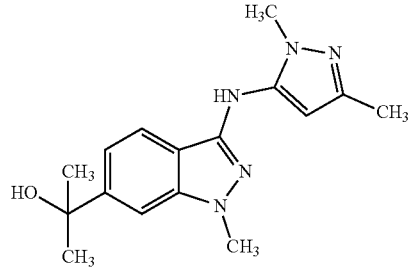 [SMILES: Cc1cc(Nc2nn(C)c3cc(C(C)(C)O)ccc23)n(C)n1] | 300.3 |

TABLE 1-3-continued

| | | | |
|---|---|---|---|
| 12 | 2-{3-[2-methoxy-4-(1-methyl-1H-pyrazol-4-yl)anilino]-1H-indazol-6-yl}propan-2-ol | | 378.3 |
| 13 | 2-(3-{[5-chloro-1-(difluoromethyl)-1H-pyrazol-4-yl]amino}-1-methyl-1H-indazol-6-yl)propan-2-ol | | 356.2 |
| 14 | 2-{3-[(1,5-dimethyl-1H-pyrazol-3-yl)amino]-1-methyl-1H-indazol-6-yl}propan-2-ol | | 300.2 |
| 15 | 2-{3-[(5-methoxy-1-methyl-1H-pyrazol-4-yl)amino]-1-methyl-1H-indazol-6-yl}propan-2-ol | | 316.3 |

TABLE 1-4

| | | | |
|---|---|---|---|
| 16 | 2-{3-[(1,3-dimethyl-1H-pyrazol-4-yl)amino]-1-methyl-1H-indazol-6-yl}propan-2-ol | | 300.3 |

TABLE 1-4-continued

| | | | |
|---|---|---|---|
| 17 | 2-{3-[(4-chloro-1-methyl-1H-pyrazol-3-yl)amino]-1-methyl-1H-indazol-6-yl}propan-2-ol | | 320.2 |
| 18 | 2-{3-[(4-chloro-1,5-dimethyl-1H-pyrazol-3-yl)amino]-1-methyl-1H-indazol-6-yl}propan-2-ol | | 334.2 |
| 19 | 2-{1-methyl-3-[(4,5,6,7-tetrahydropyrazolo[1,5-a]pyridin-3-yl)amino]-1H-indazol-6-yl}propan-2-ol | | 326.3 |
| 20 | 2-{3-[(6,7-dihydro-5H-pyrazolo[5,1-b][1,3]oxazin-3-yl)amino]-1-methyl-1H-indazol-6-yl}propan-2-ol | | 328.3 |

TABLE 1-5

| | | | |
|---|---|---|---|
| 21 | 2-{3-[(1-ethyl-5-methyl-1H-pyrazol-3-yl)amino]-1-methyl-1H-indazol-6-yl}propan-2-ol | | 314.3 |

TABLE 1-5-continued
| | | | |
|---|---|---|---|
| 22 | 2-(1-methyl-3-{[5-methyl-1-(2-methylpropyl)-1H-pyrazol-3-yl]amino}-1H-indazol-6-yl)propan-2-ol | 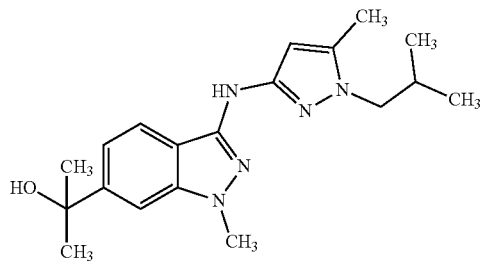 [SMILES: Cc1cc(Nc2nn(C)c3cc(C(C)(C)O)ccc23)nn1CC(C)C] | 342.2 |
| 23 | 2-{3-[(5-ethyl-1-methyl-1H-pyrazol-3-yl)amino]-1-methyl-1H-indazol-6-yl}propan-2-ol | 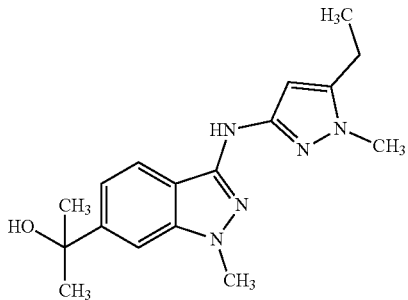 [SMILES: CCc1cc(Nc2nn(C)c3cc(C(C)(C)O)ccc23)nn1C] | 314.3 |
| 24 | 2-(1-methyl-3-{[5-methyl-1-(2,2,2-trifluoroethyl)-1H-pyrazol-3-yl]amino}-1H-indazol-6-yl)propan-2-ol | 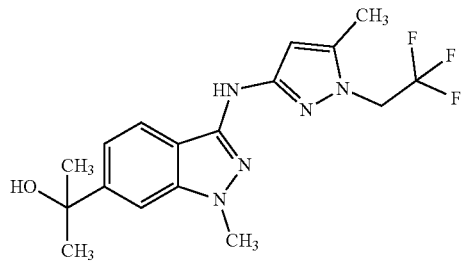 [SMILES: Cc1cc(Nc2nn(C)c3cc(C(C)(C)O)ccc23)nn1CC(F)(F)F] | 368.2 |
| 25 | 2-{3-[(6,6-dimethyl-6,7-dihydro-5H-pyrazolo[5,1-b][1,3]oxazin-3-yl)amino]-1-methyl-1H-indazol-6-yl}propan-2-ol | 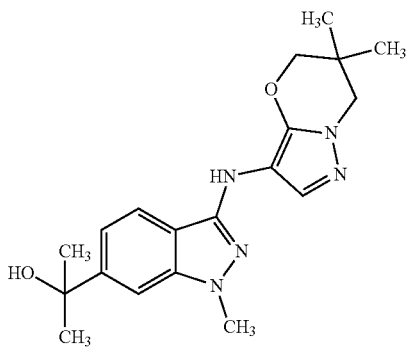 [SMILES: Cn1nc(Nc2cnn3c2OCC(C)(C)C3)c2ccc(C(C)(C)O)cc21] | 356.3 |
TABLE 1-6
| | | | |
|---|---|---|---|
| 26 | 2-{3-[2-fluoro-4-(1-methyl-1H-pyrazol-4-yl)anilino]-1H-indazol-6-yl}propan-2-ol | 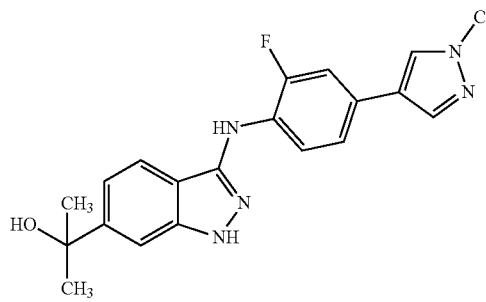 | 366.2 |

TABLE 1-6-continued
| | | | |
|---|---|---|---|
| 27 | 2-{4-fluoro-3-[(5-methoxy-1-methyl-1H-pyrazol-4-yl)amino]-1-methyl-1H-indazol-6-yl}propan-2-ol | 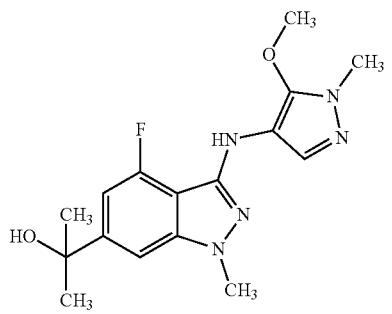 [SMILES: COc1c(Nc2nn(C)c3cc(C(C)(C)O)cc(F)c23)cnn1C] | 334.3 |
| 28 | 2-{7-fluoro-3-[(5-methoxy-1-methyl-1H-pyrazol-4-yl)amino]-1-methyl-1H-indazol-6-yl}propan-2-ol | 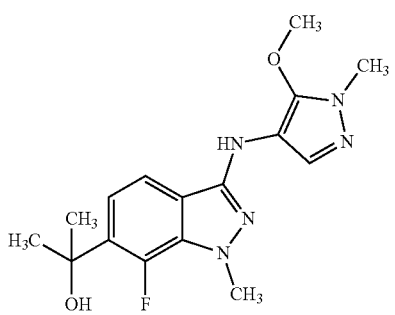 [SMILES: COc1c(Nc2nn(C)c3c(F)c(C(C)(C)O)ccc23)cnn1C] | 334.2 |
| 29 | 2-(3-{[5-(methoxymethyl)-1-methyl-1H-pyrazol-4-yl]amino}-1-methyl-1H-indazol-6-yl)propan-2-ol | 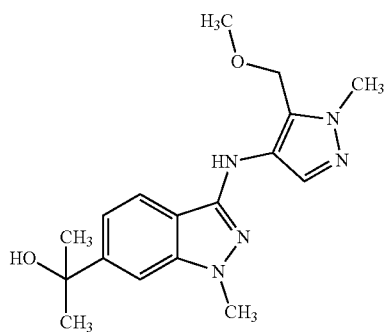 [SMILES: COCc1c(Nc2nn(C)c3cc(C(C)(C)O)ccc23)cnn1C] | 330.3 |
| 30 | 2-{3-[(5-ethoxy-1-methyl-1H-pyrazol-4-yl)amino]-1-methyl-1H-indazol-6-yl}propan-2-ol | 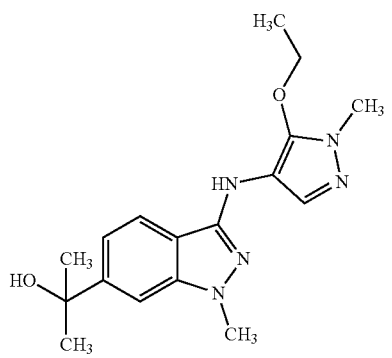 [SMILES: CCOc1c(Nc2nn(C)c3cc(C(C)(C)O)ccc23)cnn1C] | 330.3 |

TABLE 1-7
| 31 | 2-{5-fluoro-3-[(5-methoxy-1-methyl-1H-pyrazol-4-yl)amino]-1-methyl-1H-indazol-6-yl}propan-2-ol | 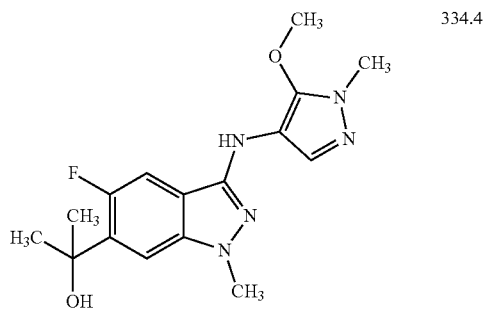 | 334.4 |
| 32 | 2-{3-[(1-ethyl-5-methoxy-1H-pyrazol-4-yl)amino]-1-methyl-1H-indazol-6-yl}propan-2-ol | 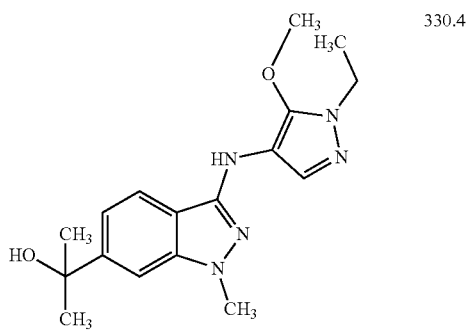 | 330.4 |
| 33 | 2-[1-methyl-3-({1-methyl-5-[(propan-2-yl)oxy]-1H-pyrazol-4-yl}amino)-1H-indazol-6-yl]propan-2-ol | 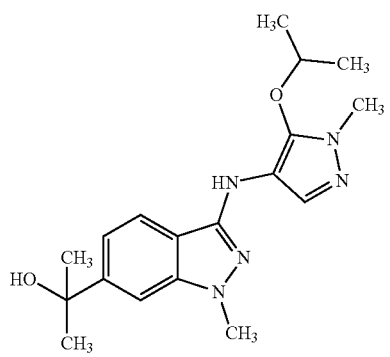 [SMILES: CC(C)Oc1c(Nc2nn(C)c3cc(C(C)(C)O)ccc23)cnn1C] | 344.4 |
| 34 | 2-{1-ethyl-3-[(5-methoxy-1-methyl-1H-pyrazol-4-yl)amino]-1H-indazol-6-yl}propan-2-ol | 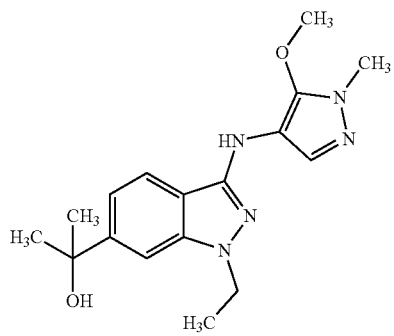 [SMILES: CCn1nc(Nc2cnn(C)c2OC)c2ccc(C(C)(C)O)cc21] | 330.3 |

TABLE 1-7-continued
| 35 | 2-(3-{[5-methoxy-1-(propan-2-yl)-1H-pyrazol-4-yl]amino}-1-methyl-1H-indazol-6-yl)propan-2-ol | 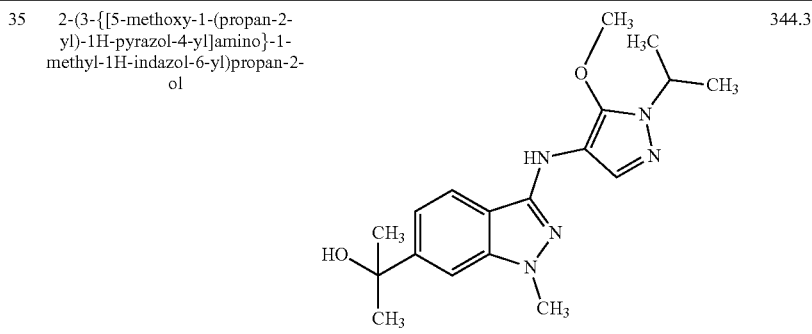 | 344.3 |
TABLE 1-8
| 36 | 2-{1-ethyl-3-[(3-methoxy-1-methyl-1H-pyrazol-4-yl)amino]-1H-indazol-6-yl}propan-2-ol | 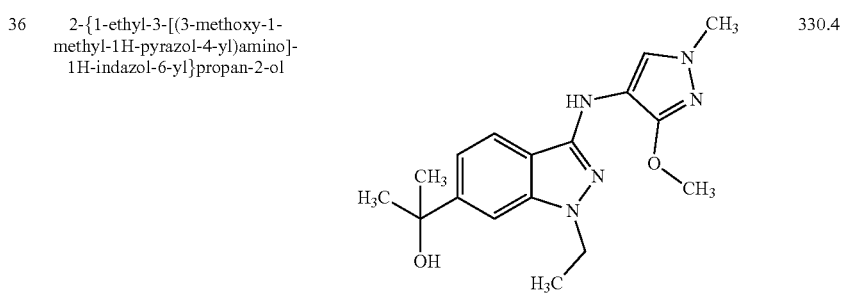 | 330.4 |
| 37 | 2-{3-[(5-methoxy-1-methyl-1H-pyrazol-4-yl)amino]-1-(propan-2-yl)-1H-indazol-6-yl}propan-2-ol | 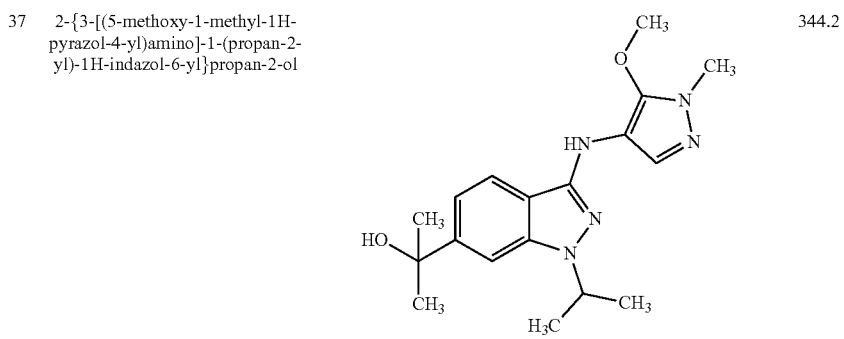 | 344.2 |
| 38 | 2-{1-(cyclopropylmethyl)-3-[(5-methoxy-1-methyl-1H-pyrazol-4-yl)amino]-1H-indazol-6-yl}propan-2-ol | 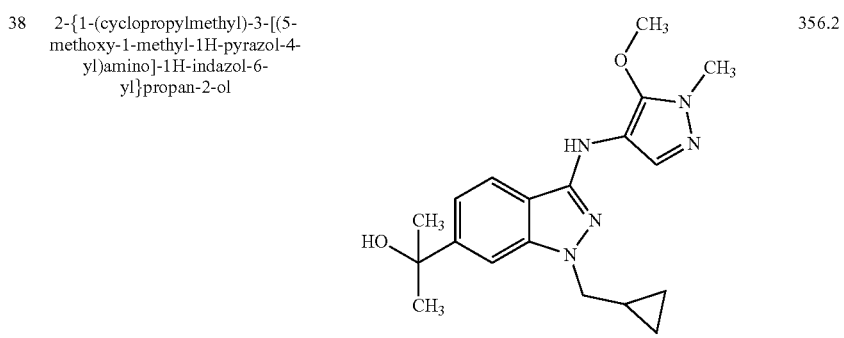 | 356.2 |

TABLE 1-8-continued

| 39 | 2-{3-[(3-methoxy-1-methyl-1H-pyrazol-4-yl)amino]-1-(propan-2-yl)-1H-indazol-6-yl}propan-2-ol | | 344.2 |
| --- | --- | --- | --- |
| 40 | 2-(3-{[5-methoxy-1-(2-methylpropyl)-1H-pyrazol-4-yl]amino}-1-methyl-1H-indazol-6-yl)propan-2-ol | | 358.3 |

TABLE 1-9

| 41 | 2-{3-[(3-methoxy-1-methyl-1H-pyrazol-4-yl)amino]-1-methyl-1H-indazol-5-yl}propan-2-ol | | 316.3 |
| --- | --- | --- | --- |
| 42 | 2-{3-[(5-methoxy-1-methyl-1H-pyrazol-4-yl)amino]-1-methyl-1H-indazol-5-yl}propan-2-ol | | 316.2 |
| 43 | 2-{3-[(1-ethyl-3-methyl-1H-pyrazol-4-yl)amino]-1-methyl-1H-indazol-6-yl}propan-2-ol | | 314.2 |

TABLE 1-9-continued
| 44 | 2-(4-fluoro-3-{[5-methoxy-1-(2-methylpropyl)-1H-pyrazol-4-yl]amino}-1-methyl-1H-indazol-6-yl)propan-2-ol | 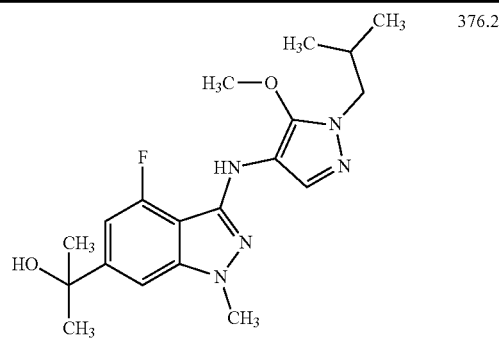 | 376.2 |
| --- | --- | --- | --- |
| 45 | 2-{3-[(1-ethyl-3-methyl-1H-pyrazol-4-yl)amino]-4-fluoro-1-methyl-1H-indazol-6-yl}propan-2-ol | 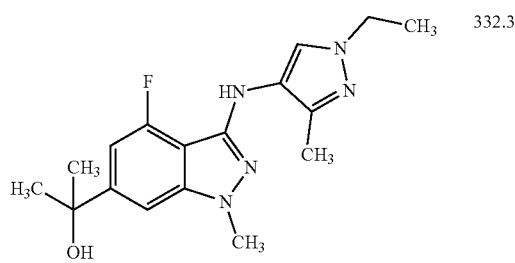 | 332.3 |
TABLE 1-10
| 46 | 2-{4-fluoro-3-[(3-methoxy-1-methyl-1H-pyrazol-4-yl)amino]-1-methyl-1H-indazol-6-yl}propan-2-ol | 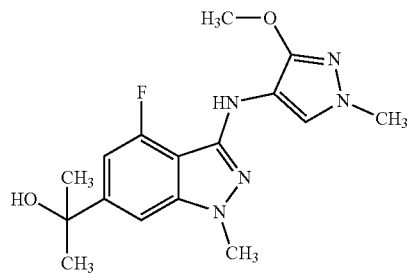 | 334.2 |
| --- | --- | --- | --- |
| 47 | 2-(3-{[5-(1-methoxyethyl)-1-methyl-1H-pyrazol-4-yl]amino}-1-methyl-1H-indazol-6-yl)propan-2-ol | 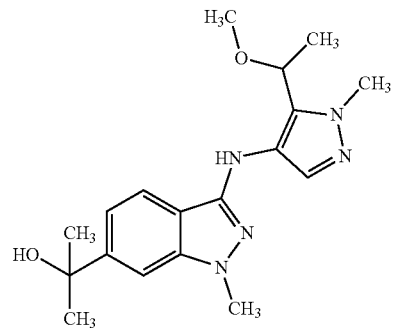 [SMILES: COC(C)c1c(Nc2nn(C)c3cc(C(C)(C)O)ccc23)cnn1C] | 344.2 |

TABLE 1-10-continued
| | | | |
|---|---|---|---|
| 48 | 2-(4-fluoro-3-{[5-(1-methoxyethyl)-1-methyl-1H-pyrazol-4-yl]amino}-1-methyl-1H-indazol-6-yl)propan-2-ol | 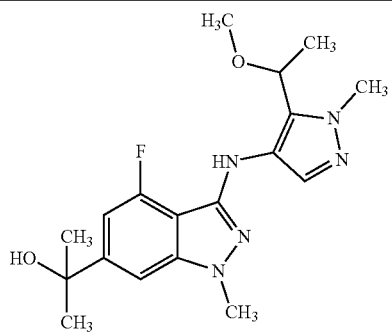 | 362.1 |
| 49 | 2-{1-(cyclopropylmethyl)-3-[(3-methoxy-1-methyl-1H-pyrazol-4-yl)amino]-1H-indazol-6-yl}propan-2-ol | 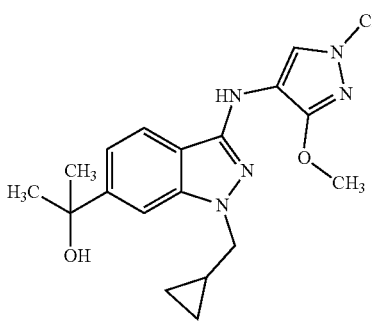 | 356.3 |
| 50 | 2-{3-[(1,3-dimethyl-1H-pyrazol-4-yl)amino]-4-fluoro-1-methyl-1H-indazol-6-yl}propan-2-ol | 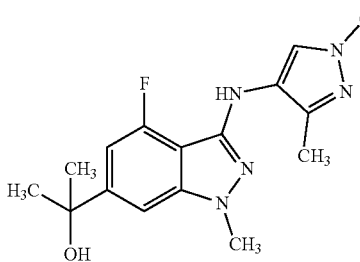 | 318.2 |
TABLE 1-11
| | | | |
|---|---|---|---|
| 51 | 2-{3-[(3-ethoxy-1-methyl-1H-pyrazol-4-yl)amino]-1-methyl-1H-indazol-6-yl}propan-2-ol | 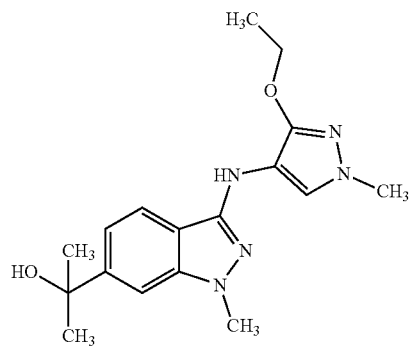 [SMILES: CCOc1nn(C)cc1Nc1nn(C)c2cc(C(C)(C)O)ccc12] | 330.3 |

TABLE 1-11-continued

| | | | | |
|---|---|---|---|---|
| 52 | 2-{4-fluoro-1-methyl-3-[(4,5,6,7-tetrahydropyrazolo[1,5-a]pyridin-3-yl)amino]-1H-indazol-6-yl}propan-2-ol | 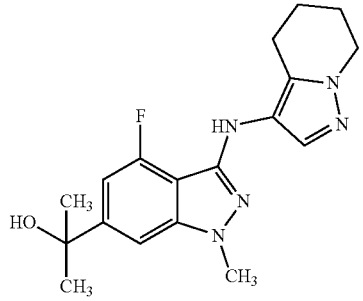 | | 344.2 |
| 53 | 2-{4-fluoro-1-methyl-3-[(4,5,6,7-tetrahydropyrazolo[1,5-a]pyridin-3-yl)amino]-1H-indazol-6-yl}propan-2-ol hydrochloride | 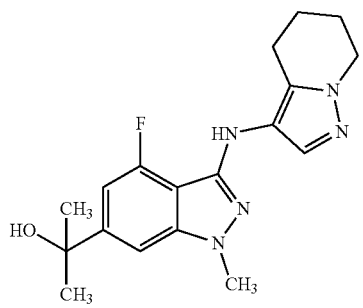 [SMILES: Cn1nc(Nc2cnn3c2CCCC3)c2c(F)cc(C(C)(C)O)cc21] | HCl | 344.2 |
| 54 | 2-{3-[(6,7-dihydro-5H-pyrazolo[5,1-b][1,3]oxazin-3-yl)amino]-4-fluoro-1-methyl-1H-indazol-6-yl}propan-2-ol | 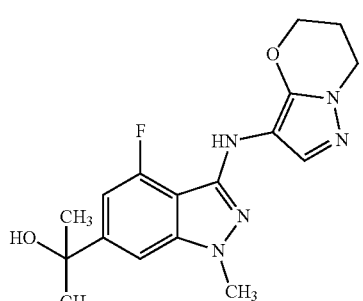 | | 346.3 |
| 55 | 2-(5-fluoro-3-{[5-methoxy-1-(2-methylpropyl)-1H-pyrazol-4-yl]amino}-1-methyl-1H-indazol-6-yl)propan-2-ol | 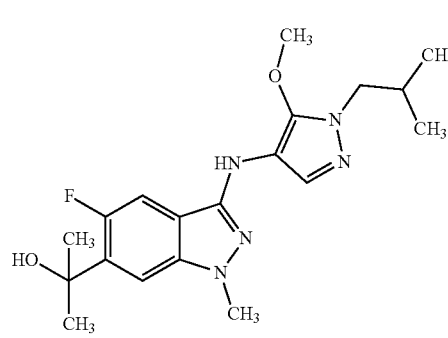 | | 376.2 |

TABLE 1-12

| | | | | |
|---|---|---|---|---|
| 56 | 2-{3-[(6,7-dihydro-5H-pyrazolo[5,1-b][1,3]oxazin-3-yl)amino]-5-fluoro-1-methyl-1H-indazol-6-yl}propan-2-ol | 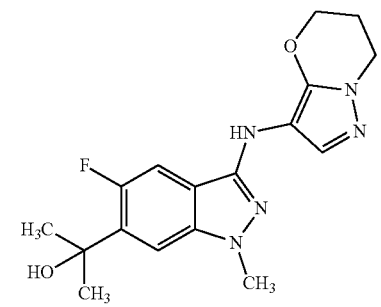 [SMILES: Cn1nc(Nc2cnn3c2OCCC3)c2cc(F)c(C(C)(C)O)cc21] | | 346.2 |

TABLE 1-12-continued
| | | | |
|---|---|---|---|
| 57 | 2-{3-[2-methoxy-3-(1-methyl-1H-pyrazol-4-yl)anilino]-1H-indazol-6-yl}propan-2-ol | 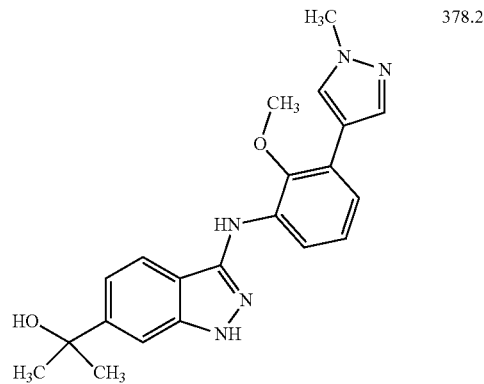 | 378.2 |
| 58 | 2-{3-[(3-chloro-1-methyl-1H-pyrazol-4-yl)amino]-1-methyl-1H-indazol-5-yl}propan-2-ol | 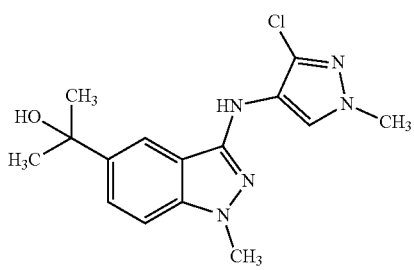 [SMILES: Cn1cc(Nc2nn(C)c3ccc(C(C)(C)O)cc23)c(Cl)n1] | 320.2 |
| 59 | 2-[3-(cyclohexylamino)-1-methyl-1H-indazol-5-yl]propan-2-ol | 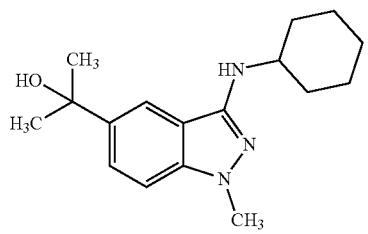 [SMILES: Cn1nc(NC2CCCCC2)c2cc(C(C)(C)O)ccc21] | 288.2 |
| 60 | 2-{3-[(6,6-difluoro-6,7-dihydro-5H-pyrazolo[5,1-b][1,3]oxazin-3-yl)amino]-1-methyl-1H-indazol-5-yl}propan-2-ol | 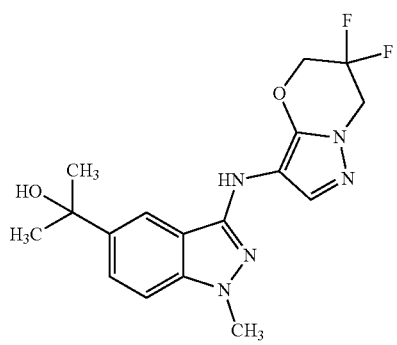 [SMILES: Cn1nc(Nc2cnn3c2OCC(F)(F)C3)c2cc(C(C)(C)O)ccc21] | 364.2 |
TABLE 1-13
| | | | |
|---|---|---|---|
| 61 | 2-{1-(cyclopropylmethyl)-3-[(1,3-dimethyl-1H-pyrazol-4-yl)amino]-1H-indazol-5-yl}propan-2-ol | 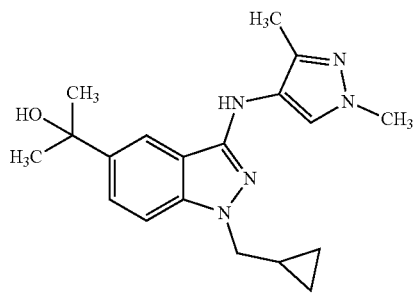 [SMILES: Cc1nn(C)cc1Nc1nn(CC2CC2)c2ccc(C(C)(C)O)cc12] | 340.2 |

TABLE 1-13-continued
| | | | |
|---|---|---|---|
| 62 | 2-(1-methyl-3-{[3-methyl-1-(propan-2-yl)-1H-pyrazol-4-yl]amino}-1H-indazol-5-yl)propan-2-ol | 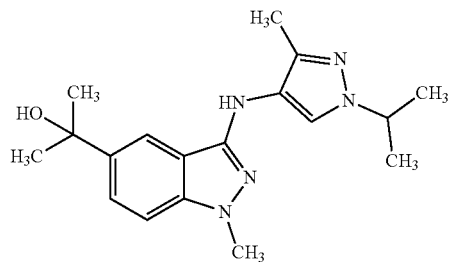 [SMILES: Cc1nn(C(C)C)cc1Nc1nn(C)c2ccc(C(C)(C)O)cc12] | 328.2 |
| 63 | 2-(1-methyl-3-{[5-methyl-1-(propan-2-yl)-1H-pyrazol-4-yl]amino}-1H-indazol-5-yl)propan-2-ol | 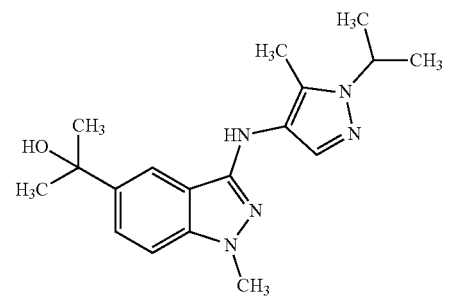 [SMILES: Cc1c(Nc2nn(C)c3ccc(C(C)(C)O)cc23)cnn1C(C)C] | 328.2 |
| 64 | 2-{1-[(2,2-difluorocyclopropyl)methyl]-3-[(1,3-dimethyl-1H-pyrazol-4-yl)amino]-1H-indazol-5-yl}propan-2-ol | 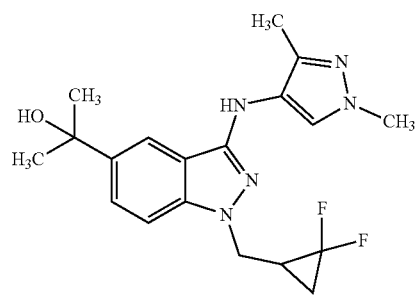 [SMILES: Cc1nn(C)cc1Nc1nn(CC2CC2(F)F)c2ccc(C(C)(C)O)cc12] | 376.2 |
| 65 | 2-{1-cyclobutyl-3-[(1,3-dimethyl-1H-pyrazol-4-yl)amino]-1H-indazol-5-yl}propan-2-ol | 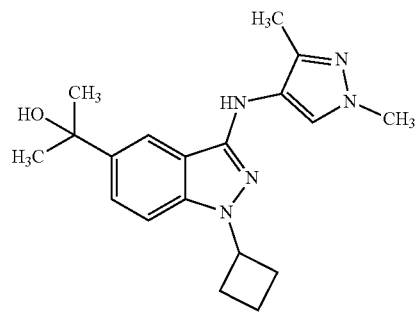 [SMILES: Cc1nn(C)cc1Nc1nn(C2CCC2)c2ccc(C(C)(C)O)cc12] | 340.2 |
TABLE 1-14
| | | | |
|---|---|---|---|
| 66 | 2-{3-[(1,3-dimethyl-1H-pyrazol-4-yl)amino]-1-(propan-2-yl)-1H-indazol-5-yl}propan-2-ol | 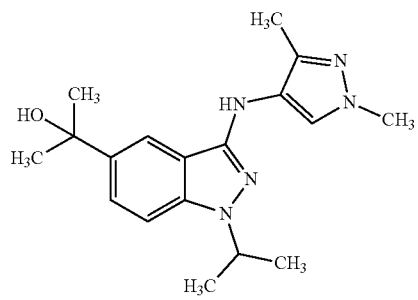 [SMILES: Cc1nn(C)cc1Nc1nn(C(C)C)c2ccc(C(C)(C)O)cc12] | 328.2 |

TABLE 1-14-continued
| 67 | 2-{1-(cyclopropylmethyl)-3-[(3-methoxy-1-methyl-1H-pyrazol-4-yl)amino]-1H-indazol-5-yl}propan-2-ol | 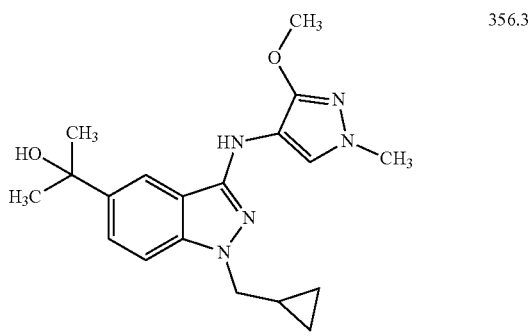 | 356.3 |
| 68 | 2-{1-cyclobutyl-3-[(3-methoxy-1-methyl-1H-pyrazol-4-yl)amino]-1H-indazol-6-yl}propan-2-ol | 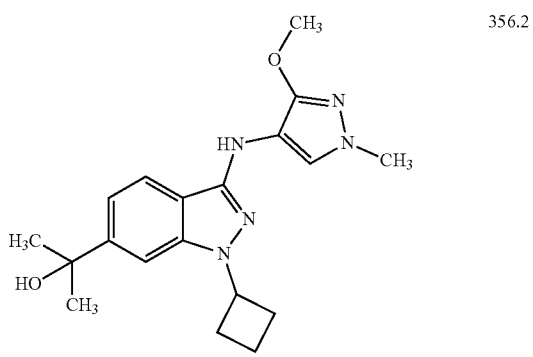 | 356.2 |
| 69 | 2-{3-[2-methoxy-5-(1-methyl-1H-pyrazol-4-yl)anilino]-1H-indazol-6-yl}propan-2-ol | 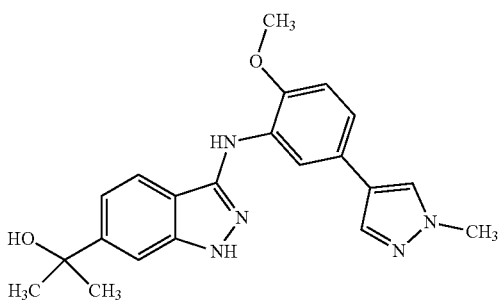 [SMILES: COc1ccc(-c2cnn(C)c2)cc1Nc1n[nH]c2cc(C(C)(C)O)ccc12] | 378.3 |
| 70 | 2-{1-cyclobutyl-3-[(3-methoxy-1-methyl-1H-pyrazol-4-yl)amino]-1H-indazol-5-yl}propan-2-ol | 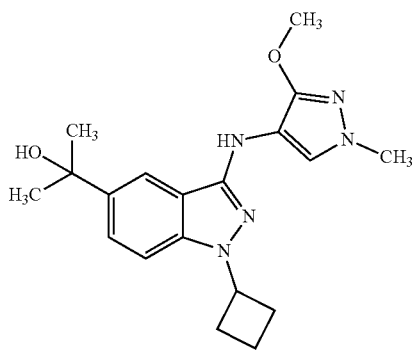 [SMILES: COc1nn(C)cc1Nc1nn(C2CCC2)c2ccc(C(C)(C)O)cc12] | 356.3 |

TABLE 1-15

| | | | |
|---|---|---|---|
| 71 | 2-{3-[(3-methoxy-1-methyl-1H-pyrazol-4-yl)amino]-1-(propan-2-yl)-1H-indazol-5-yl}propan-2-ol | 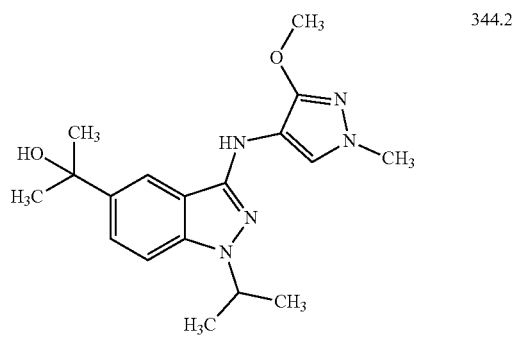 | 344.2 |
| 72 | optically active 2-{1-[(2,2-difluorocyclopropyl)methyl]-3-[(3-methoxy-1-methyl-1H-pyrazol-4-yl)amino]-1H-indazol-5-yl}propan-2-ol (tR1) | 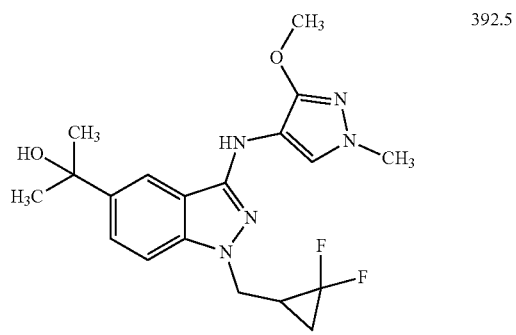 | 392.5 |
| 73 | 2-(1-methyl-3-{[5-methyl-1-(2-methylpropyl)-1H-pyrazol-4-yl]amino}-1H-indazol-5-yl)propan-2-ol | 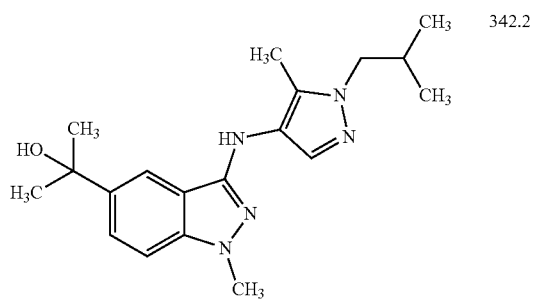 | 342.2 |
| 74 | 2-{3-[(1-cyclobutyl-3-methyl-1H-pyrazol-4-yl)amino]-1-methyl-1H-indazol-5-yl}propan-2-ol | 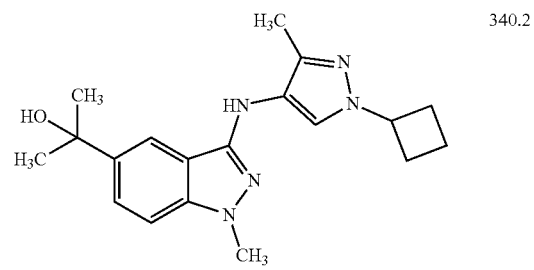 | 340.2 |
| 75 | 2-{3-[(1-cyclobutyl-5-methyl-1H-pyrazol-4-yl)amino]-1-methyl-1H-indazol-5-yl}propan-2-ol | 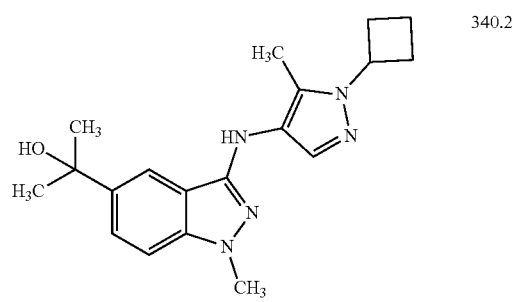 | 340.2 |

TABLE 1-16

| 76 | optically active 2-{1-[(2,2-difluorocyclopropyl)methyl]-3-[(1,3-dimethyl-1H-pyrazol-4-yl)amino]-1H-indazol-6-yl}propan-2-ol (tR1) | 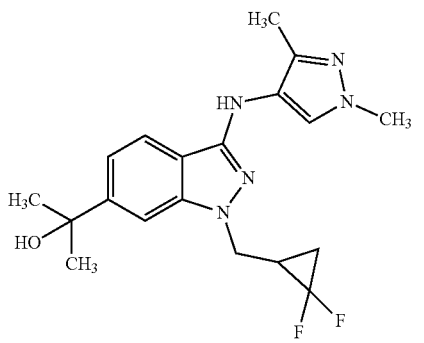 [SMILES: Cc1nn(C)cc1Nc1nn(CC2CC2(F)F)c2cc(C(C)(C)O)ccc12] | 376.2 |
| 77 | optically active 2-{1-[(2,2-difluorocyclopropyl)methyl]-3-[(3-methoxy-1-methyl-1H-pyrazol-4-yl)amino]-1H-indazol-6-yl}propan-2-ol (tR1) | 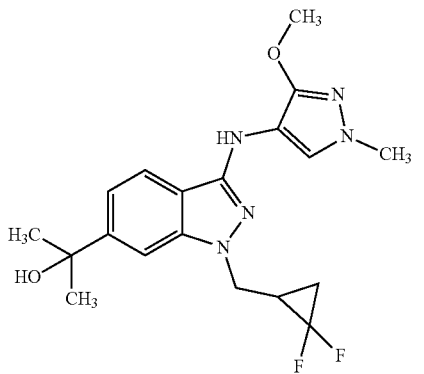 [SMILES: COc1nn(C)cc1Nc1nn(CC2CC2(F)F)c2cc(C(C)(C)O)ccc12] | 392.2 |
| 78 | 2-{1-cyclobutyl-3-[(1,3-dimethyl-1H-pyrazol-4-yl)amino]-1H-indazol-6-yl}propan-2-ol | 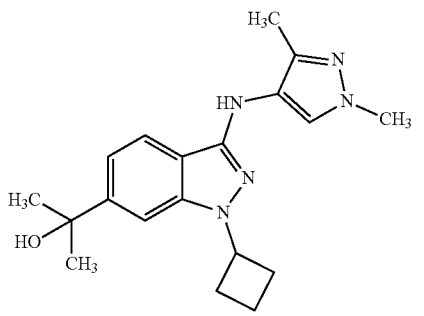 [SMILES: Cc1nn(C)cc1Nc1nn(C2CCC2)c2cc(C(C)(C)O)ccc12] | 340.2 |
| 79 | optically active 2-{1-[(2,2-difluorocyclopropyl)methyl]-3-[(3-methoxy-1-methyl-1H-pyrazol-4-yl)amino]-1H-indazol-5-yl}propan-2-ol (tR2) | 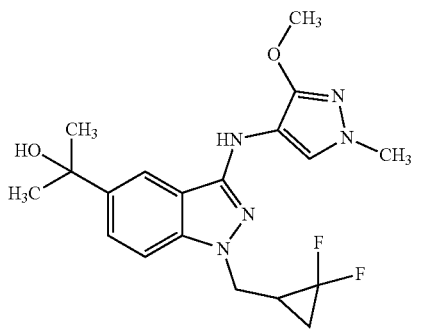 [SMILES: COc1nn(C)cc1Nc1nn(CC2CC2(F)F)c2ccc(C(C)(C)O)cc12] | 392.2 |

TABLE 1-16-continued

| 80 | optically active 2-{1-[(2,2-difluorocyclopropyl)methyl]-3-[(1,3-dimethyl-1H-pyrazol-4-yl)amino]-1H-indazol-6-yl}propan-2-ol (tR2) | | 376.2 |

TABLE 1-17

| 81 | optically active 2-{1-[(2,2-difluorocyclopropyl)methyl]-3-[(3-methoxy-1-methyl-1-pyrazol-4-yl)amino]-1H-indazol-6-yl}propan-2-ol (tR2) | | 392.2 |
| 82 | 2-(1-cyclobutyl-3-{[3-(methoxymethyl)-1-methyl-1H-pyrazol-4-yl]amino}-1H-indazol-6-yl)propan-2-ol | | 370.3 |
| 83 | 2-(1-[(2,2-difluorocyclopropyl)methyl]-3-{[3-(methoxymethyl)-1-methyl-1H-pyrazol-4-yl]amino}-1H-indazol-6-yl)propan-2-ol | | 406.2 |

TABLE 1-17-continued
| 84 | 2-[1-(cyclopropylmethyl)-3-{[3-(methoxymethyl)-1-methyl-1H-pyrazol-4-yl]amino}-1H-indazol-6-yl]propan-2-ol | 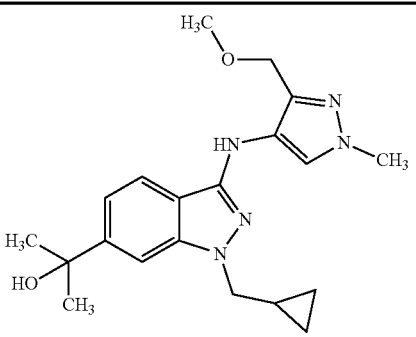 | 370.3 |
| --- | --- | --- | --- |
| 85 | 2-[3-{[3-(methoxymethyl)-1-methyl-1H-pyrazol-4-yl]amino}-1-(propan-2-yl)-1H-indazol-6-yl]propan-2-ol | 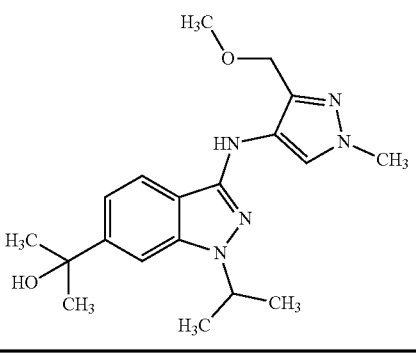 | 358.2 |
TABLE 1-18
| 86 | 2-[3-{[3-(methoxymethyl)-1-methyl-1H-pyrazol-4-yl]amino}-1-(propan-2-yl)-1H-indazol-5-yl]propan-2-ol | 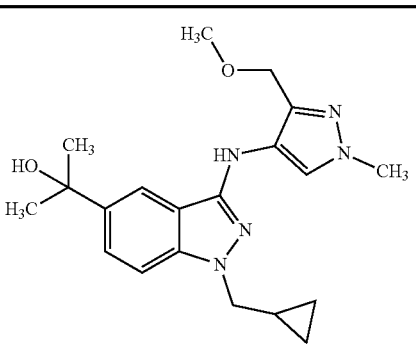 | 358.2 |
| --- | --- | --- | --- |
| 87 | 2-[1-(cyclopropylmethyl)-3-{[3-(methoxymethyl)-1-methyl-1H-pyrazol-4-yl]amino}-1H-indazol-5-yl]propan-2-ol | 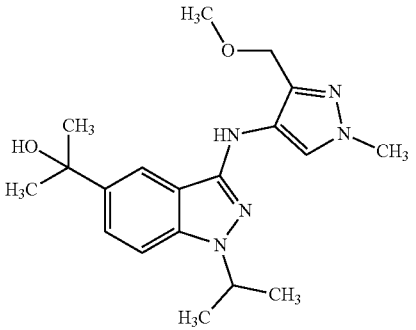 [SMILES: COCc1nn(C)cc1Nc1nn(C(C)C)c2ccc(C(C)(C)O)cc12] | 370.2 |

TABLE 1-18-continued

| 88 | 2-(1-cyclobutyl-3-{[3-(methoxymethyl)-1-methyl-1H-pyrazol-4-yl]amino}-1H-indazol-5-yl)propan-2-ol | 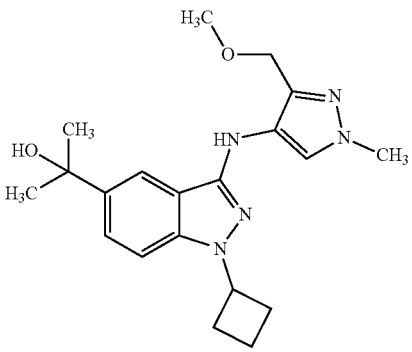 [SMILES: COCc1nn(C)cc1Nc1nn(C2CCC2)c2ccc(C(C)(C)O)cc12] | 370.3 |
| --- | --- | --- | --- |
| 89 | 2-(1-[(2,2-difluorocyclopropyl)methyl]-3-{[3-(methoxymethyl)-1-methyl-1H-pyrazol-4-yl]amino}-1H-indazol-5-yl)propan-2-ol | 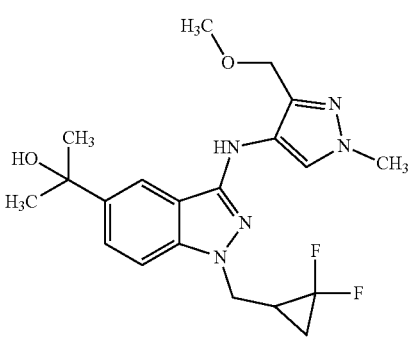 [SMILES: COCc1nn(C)cc1Nc1nn(CC2CC2(F)F)c2ccc(C(C)(C)O)cc12] | 406.2 |

Experimental Example 1

ALS is a typical motor neuron disease caused by motor neuron degeneration, of which 5-10% is hereditary and familial. Among the iPS cell clones described in Non-Patent Document 11, using the clone ALS1 established from a familial ALS patient having the SOD1 gene mutation L144FVX, the effects of the compounds according to the present disclosure was examined. Specifically, the denaturation-suppressing effect on the familial ALS cell model was analyzed using the stable line of ALS1 into which the tetracycline-induced Lhx3, Ngn2 and Isl1 genes were introduced (hereinafter, simply referred to as ALS1 cells). ALS1 cells are an ALS cell model that rapidly differentiates into motor neurons (within about 7 days) by adding tetracycline or a derivative thereof to the medium, and spontaneously induces degeneration after differentiation (Non-Patent Document 11). Therefore, in ALS1 cells, remarkable neurodegeneration and cell death are observed from about 7 days to 14 days after the induction of differentiation into motor neurons (that is, the induction of expression of the Lhx3, Ngn2 and Isl1 genes) (Non-Patent Document 11).

ALS1 cells were cultured on feeder cells (mitomycin-treated SNL cells) in an iPS cell maintenance medium consisting of Primate ES Cell medium (ReproCell, RCHEMD001A), 4 ng/ml hbFGF (Wako, 060-04543), 50 μg/ml G418 (Nacalai, 09380-86) and Penicillin-Streptomycin (Thermo Fisher Scientific, 15140-122).

The method for seeding ALS1 cells on an assay plate is as follows.

Assay medium consisting of DMEM/F-12 (1:1) (Thermo Fisher Scientific, 11330-057), N2 supplement (Thermo Fisher Scientific, 17502-048), Penicillin-Streptomycin (Thermo Fisher Scientific, 15140-122), 10 ng/ml recombinant human BDNF (PeproTech, 450-02), 10 ng/ml recombinant human GDNF (PeproTech, 450-10), 10 ng/ml recombinant human NT-3 (PeproTech, 450-03), 1 μM retinoic acid (Sigma, R2625), 1 μg/ml Doxycycline (Clontech, 631311), 1 μM SAG (Enzo life sciences, ALX-270-426-M001) and 10 μM Y-27632 (Wako, 253-00513) was used, and a 384-well plate was coated with 20-fold diluted matrigel.

Next, ALS1 cells were suspended in the assay medium, and was seeded on the matrigel-coated assay plate at 1×10$^4$ cells per well.

The method for counting the motor neurons differentiated from ALS1 cells is as follows.

For the ALS1 cells seeded on the assay plate according to the method described in the previous section, the assay medium containing no Y-27632 was added to the plate 4 days after seeding, and the cells were cultured until 6 days after seeding, fixed with PFA (Wako, 163-20145), and immunostained with (III-tubulin. After cell fixation, membrane permeation treatment and blocking, a primary antibody solution prepared by diluting anti-III-tubulin antibody (R&D, MAB1195) 10,000 times was added to the plate, and the plate was left stand at room temperature for 3.5 hours. After washing and removing the primary antibody, a secondary antibody solution prepared by diluting Alexa Fluor 488 goat anti-mouse IgG (H+L) (Molecular Probes, A11029) 1,000 times with the same solution as for the primary antibody was added to the plate, and the plate was left stand at room temperature for 1 hour. Finally, after washing and removing the secondary antibody, D-PBS (-) was dispensed to the plate. Most of the III-tubulin-positive cells obtained by this method (that is, differentiation induction by the induction of expression of the Lhx3, Ngn2, and Isl1 genes) are motor neurons.

By measuring the above plates with a high content analyzer, the number of the (III-tubulin-positive cells per well (that is, the number of the living motor neurons) was counted. The high-content analyzer used was Opera Phenix from PerkinElmer.

The method for detecting the activity of the test compound is as follows.

From 6 days to 14 days after the start of the culture, the cells were cultured in an assay medium (without retinoic acid, Doxycycline, SAG and Y-27632) containing a predetermined concentration of the test compound. The cells were immunostained according to the method described in the previous section 6 days and 14 days after the start of the culture, and the number of the living motor neurons (βIII-tubulin positive cells) was counted. In motor neurons differentiated from ALS1 cells, most of the motor neurons that started degeneration have a marked atrophy or fragmentation of the cell body by 14 days. Therefore, by counting the number of the cells (more specifically, the number of the cell bodies) that were βIII-tubulin positive after 14 days, the number of the living motor neurons can be evaluated. As a negative control, cells cultured in an assay medium added with DMSO instead of the test compound were used.

The degree to which the test compound suppressed the decrease in the number of the motor neurons in the negative control is defined as the motor neuron degeneration inhibitory activity of the test compound, which was calculated by the following formula.

Motor neuron degeneration inhibitory activity of the test compound=$((X-C)/(T-C))\times100$ X: Number of the motor neurons in the test compound group 14 days after the start of the culture,
C: Number of the motor neurons in the DMSO group 14 days after the start of the culture,
T: Number of the motor neurons 6 days after the start of the culture The concentration of the test compound added to the assay plate was 0.03, 0.1, 0.3, 1, 3 and 10 μmol/l as 6 points. The concentration range of the test compound showing activity of 40% or more is shown in the following Table 2.

TABLE 2-1

| Example No. | concentration range of test compound showing activity of 40% or more |
|---|---|
| 1 | 0.3-3 μM |
| 2 | 0.3-10 μM |
| 3 | 0.3-10 μM |
| 4 | 3-10 μM |
| 5 | 0.3-10 μM |
| 6 | 1-10 μM |
| 7 | 0.3-10 μM |
| 8 | 1-10 μM |
| 9 | 0.3-10 μM |
| 10 | 1-10 μM |
| 11 | 3-10 μM |
| 12 | 0.3-10 μM |
| 13 | 0.3-10 μM |
| 14 | 3-10 μM |
| 15 | 3-10 μM |
| 16 | 1-10 μM |
| 17 | 3-10 μM |
| 18 | 3-10 μM |
| 19 | 0.3-10 μM |
| 20 | 1-10 μM |
| 21 | 3-10 μM |
| 22 | 1-10 μM |
| 23 | 1-10 μM |
| 24 | 3-10 μM |
| 25 | 3-10 μM |
| 26 | 0.3-10 μM |
| 27 | 3-10 μM |
| 28 | 1-10 μM |
| 29 | 1-10 μM |
| 30 | 1-10 μM |
| 31 | 1-10 μM |

TABLE 2-1-continued

| Example No. | concentration range of test compound showing activity of 40% or more |
|---|---|
| 32 | 1-10 μM |
| 33 | 1-10 μM |
| 34 | 1-10 μM |
| 35 | 0.3-10 μM |
| 36 | 0.3-10 μM |
| 37 | 1-10 μM |
| 38 | 1-10 μM |
| 39 | 0.3-10 μM |
| 40 | 0.3-10 μM |
| 41 | 1-10 μM |
| 42 | 3-10 μM |
| 43 | 0.3-10 μM |
| 44 | 0.3-10 μM |
| 45 | 1-10 μM |
| 46 | 1-10 μM |
| 47 | 1-10 μM |
| 48 | 3-10 μM |
| 49 | 0.3-10 μM |
| 50 | 1-10 μM |
| 51 | 0.3-10 μM |
| 52 | 0.3-10 μM |
| 53 | 0.3-10 μM |
| 54 | 3-10 μM |
| 55 | 0.3-10 μM |
| 56 | 0.3-10 μM |
| 57 | 1-10 μM |
| 58 | 1-10 μM |
| 59 | 0.3-10 μM |
| 60 | 1-10 μM |
| 61 | 0.3-10 μM |
| 62 | 0.3-10 μM |
| 63 | 0.3-10 μM |
| 64 | 0.3-10 μM |
| 65 | 0.3-10 μM |
| 66 | 0.3-10 μM |
| 67 | 0.3-10 μM |
| 68 | 0.3-10 μM |
| 69 | 0.3-10 μM |
| 70 | 0.1-10 μM |
| 71 | 0.3-10 μM |
| 72 | 0.3-10 μM |
| 73 | 0.3-10 μM |
| 74 | 0.3-10 μM |
| 75 | 0.3-10 μM |
| 76 | 0.3-10 μM |
| 77 | 0.3-10 μM |
| 78 | 0.3-10 μM |
| 79 | 0.3-10 μM |
| 80 | 0.3-10 μM |
| 81 | 0.3-10 μM |
| 82 | 0.3-10 μM |
| 83 | 1-10 μM |
| 84 | 1-10 μM |
| 85 | 1-10 μM |
| 86 | 1-10 μM |
| 87 | 1-10 μM |
| 88 | 0.3-10 μM |
| 89 | 1-10 μM |

Experimental Example 2

The effects of the compounds according to the present disclosure were evaluated according to the literature (M. G. Cotticelli et al, J Pharmacol Exp Ther 2019, 369, 47-54.).

Skin fibroblasts derived from FA patients (Coriell Institute for Medical Research, GM4078) were cultured in a culture medium consisting of DMEM (Thermo Fisher Scientific, 11995-065), 10% fetal bovine serum (Thermo Fisher Scientific, 26140-087), 1% GlutaMAX supplement (Thermo Fisher Scientific, 35050-061) and 1% Penicillin-Streptomycin solution (FUJIFILM Wako Pure Chemical Corporation, 168-23191).

For assay, the fibroblasts in the above culture medium were seeded in a 384-well plate at 1,500 cells per well, and the test compound and 3 μmol/l (final concentration) RSL3 were added to the plate the day after seeding. The concentration of the test compound added to the assay plate was 0.01, 0.1, 1 and 10 μmol/l as 4 points, and DMSO was added as a negative control for the test compound and RSL3. Twenty-four hours after the addition of RSL3/the test compound, CellTiter-Glo Luminescent Cell Viability Assay solution (Promega, G7573) was added to the plate to lyse the cells, and ATP was measured as an index of cell viability by detecting chemiluminescence with a plate reader.

The degree to which the test compound suppressed the decrease in ATP with the addition of RSL3/without the addition of the test compound was defined as the RSL3-induced cell death inhibitory activity of the test compound, which was calculated by the following formula.

RSL3-induced cell death inhibitory activity of the test compound=$((X-C)/(T-C))\times 100$ X: ATP in the RSL3 addition/the test compound addition group,
C: ATP in the RSL3 addition/the test compound non-addition group,
T: ATP in the RSL3 non-addition/the test compound non-addition group The RSL3-induced cell death inhibitory activity at each concentration is shown in Table 3.

TABLE 3

| Example No. | RSL3-induced cell death inhibitory activity (%) at each compound concentration (μmol/l) | | | |
|---|---|---|---|---|
| | 0.01 | 0.1 | 1 | 10 |
| 2 | 4.7 | 71.7 | 95.4 | 83.5 |
| 5 | 27.8 | 53.9 | 84.5 | 82.7 |
| 9 | 30.0 | 61.8 | 96.1 | 84.6 |
| 12 | 33.2 | 57.8 | 79.9 | 85.9 |
| 19 | 11.1 | 32.1 | 58.9 | 78.9 |
| 36 | 14.0 | 28.5 | 55.8 | 86.0 |
| 39 | 58.0 | 66.4 | 83.0 | 93.2 |
| 40 | 40.7 | 63.0 | 98.1 | 94.9 |
| 41 | 21.3 | 40.8 | 58.1 | 71.7 |
| 44 | 38.3 | 61.3 | 78.4 | 95.0 |
| 49 | 37.8 | 64.9 | 96.5 | 93.0 |
| 56 | 47.4 | 69.3 | 94.2 | 90.3 |
| 59 | 48.0 | 65.9 | 93.3 | 95.9 |
| 68 | 49.5 | 66.1 | 95.5 | 93.7 |
| 70 | 12.1 | 86.1 | 89.2 | 82.2 |
| 77 | 17.7 | 46.4 | 76.2 | 77.1 |
| 82 | 1.9 | 41.6 | 64.0 | 73.8 |
| 84 | 12.4 | 47.5 | 75.7 | 73.8 |
| 85 | 11.4 | 43.2 | 68.4 | 72.6 |
| 88 | 13.6 | 61.2 | 73.0 | 72.7 |

Formulation Examples

Medicaments containing the compound of the present invention as an active ingredient can be produced, for example, by the following formulations.

1. Capsule

| (1) compound obtained in Example 1 | 10 mg |
|---|---|
| (2) lactose | 90 mg |
| (3) microcrystalline cellulose | 70 mg |
| (4) magnesium stearate capsule | 10 mg |
| 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

2. Tablet

| (1) compound obtained in Example 1 | 10 mg |
|---|---|
| (2) lactose | 35 mg |
| (3) cornstarch | 150 mg |
| (4) microcrystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

INDUSTRIAL APPLICABILITY

According to the present invention, a compound having an excellent cell degeneration inhibitory action, particularly a motor neuron degeneration inhibitory action, which is useful as an agent for the prophylaxis or treatment of motor neuron diseases (e.g., amyotrophic lateral sclerosis, progressive bulbar paralysis, progressive muscular atrophy, primary lateral sclerosis, progressive pseudobulbar paralysis, spinal muscular atrophy, Parkinson's disease, Lewy body dementia, multiple-system atrophy, Friedreich's ataxia) and the like, can be provided.

This application is based on patent application No. 2019-191533 filed on Oct. 18, 2019 in Japan, the contents of which are encompassed in full herein.

The invention claimed is:
1. A compound represented by the formula

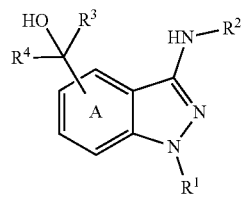

(I)

wherein
$R^1$ is a hydrogen atom, an optionally substituted $C_{1-6}$ alkyl group, or an optionally substituted $C_{3-6}$ cycloalkyl group;
$R^2$ is an optionally substituted $C_{1-6}$ alkyl group, or an optionally substituted cyclic group;
$R^3$ is an optionally substituted $C_{1-6}$ alkyl group;
$R^4$ is an optionally substituted $C_{1-6}$ alkyl group; and
Ring A is an optionally further substituted benzene ring, or a salt thereof.

2. The compound or salt according to claim 1, wherein $R^1$ is
(1) a hydrogen atom,
(2) a $C_{1-6}$ alkyl group optionally substituted by 1 to 3 of optionally halogenated $C_{3-6}$ cycloalkyl groups, or
(3) a $C_{3-6}$ cycloalkyl group;

$R^2$ is
(1) a $C_{3-6}$ cycloalkyl group,
(2) a $C_{6-10}$ aryl group optionally substituted by 1 to 3 substituents selected from
   (a) a halogen atom,
   (b) an optionally halogenated $C_{1-6}$ alkyl group,
   (c) a $C_{1-6}$ alkoxy group, and
   (d) a 5- or 6-membered monocyclic aromatic heterocyclic group optionally substituted by 1 to 3 $C_{1-6}$ alkyl groups,
(3) a 5- or 6-membered monocyclic aromatic heterocyclic group optionally substituted by 1 to 3 substituents selected from
   (a) a halogen atom,
   (b) a $C_{1-6}$ alkyl group optionally substituted by 1 to 3 substituents selected from
      (i) a halogen atom, and
      (ii) a $C_{1-6}$ alkoxy group,
   (c) a $C_{3-6}$ cycloalkyl group, and
   (d) a $C_{1-6}$ alkoxy group, or
(4) a 9- to 14-membered fused polycyclic non-aromatic heterocyclic group optionally substituted by 1 to 3 substituents selected from
   (a) a halogen atom, and
   (b) a $C_{1-6}$ alkyl group;
$R^3$ is an unsubstituted $C_{1-6}$ alkyl group;
$R^4$ is an unsubstituted $C_{1-6}$ alkyl group; and
Ring A is a benzene ring optionally further substituted by halogen atom(s).

3. The compound or salt according to claim 1, wherein $R^1$ is
(1) a hydrogen atom,
(2) a $C_{1-6}$ alkyl group optionally substituted by 1 to 3 $C_{3-6}$ cycloalkyl groups, or
(3) a $C_{3-6}$ cycloalkyl group;
$R^2$ is
(1) a $C_{6-10}$ aryl group optionally substituted by 1 to 3 substituents selected from
   (a) a $C_{1-6}$ alkoxy group, and
   (b) a 5- or 6-membered monocyclic aromatic heterocyclic group optionally substituted by 1 to 3 $C_{1-6}$ alkyl groups, or
(2) a 5- or 6-membered monocyclic aromatic heterocyclic group optionally substituted by 1 to 3 substituents selected from
   (a) a $C_{1-6}$ alkyl group optionally substituted by 1 to 3 $C_{1-6}$ alkoxy groups, and
   (b) a $C_{1-6}$ alkoxy group;
$R^3$ is an unsubstituted $C_{1-6}$ alkyl group;
$R^4$ is an unsubstituted $C_{1-6}$ alkyl group; and
Ring A is a benzene ring having no additional substituent other than formula: —C(OH) $R^3R^4$ wherein $R^3$ and $R^4$ are as defined above.

4. A medicament comprising the compound or salt according to claim 1.

5. The medicament according to claim 4, which is a motor neuron degeneration inhibitor.

6. The medicament according to claim 4, which is an agent for the prophylaxis or treatment of motor neuron disease.

7. The medicament according to claim 6, wherein the motor neuron disease is amyotrophic lateral sclerosis or Friedreich's ataxia.

8. The compound or salt according to claim 1 for use in the prophylaxis or treatment of motor neuron disease.

9. The compound or salt according to claim 8, wherein the motor neuron disease is amyotrophic lateral sclerosis or Friedreich's ataxia.

10. A method for inhibiting motor neuron degeneration in a mammal, which comprises administering an effective amount of the compound or salt according to claim 1 to the mammal.

11. A method for preventing or treating a motor neuron disease in a mammal, which comprises administering an effective amount of the compound or salt according to claim 1 to the mammal.

12. The method according to claim 11, wherein the motor neuron disease is amyotrophic lateral sclerosis or Friedreich's ataxia.

13. 2-{3-[(3-Methoxy-1-methyl-1H-pyrazol-4-yl)amino]-1-methyl-1H-indazol-5-yl}propan-2-ol or a salt thereof.

14. 2-{1-(Cyclopropylmethyl)-3-[(3-methoxy-1-methyl-1H-pyrazol-4-yl) amino]-1H-indazol-6-yl}propan-2-ol or a salt thereof.

15. 2-{3-[2-Methoxy-4-(1-methyl-1H-pyrazol-4-yl)anilino]-1H-indazol-6-yl}propan-2-ol or a salt thereof.

* * * * *